United States Patent
de Laszlo et al.

(10) Patent No.: US 6,403,584 B1
(45) Date of Patent: Jun. 11, 2002

(54) SUBSTITUTED NIPECOTYL DERIVATIVES AS INHIBITORS OF CELL ADHESION

(75) Inventors: Stephen E. de Laszlo, Rumson; Clare E. Gutteridge; William K. Hagmann, both of Westfield; Theodore M. Kamenecka, North Brunswick, all of NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/882,319

(22) Filed: Jun. 15, 2001

Related U.S. Application Data

(60) Provisional application No. 60/213,155, filed on Jun. 22, 2000.

(51) Int. Cl.[7] .................... C07D 211/12; C07D 207/06; A61K 31/4462; A61K 31/40; A61P 43/00
(52) U.S. Cl. .................... 514/237.2; 514/423; 514/183; 514/217.11; 514/327; 540/482; 540/604; 546/221; 548/537; 544/129
(58) Field of Search .................... 514/423, 327, 514/217.11, 183; 540/482, 604; 546/221; 548/537

(56) References Cited

U.S. PATENT DOCUMENTS 5,721,250 A * 2/1998 Morriello et al. ............ 514/318
5,948,792 A * 9/1999 Tsuchiya et al. ............ 514/317

* cited by examiner

Primary Examiner—Floyd D. Higel
Assistant Examiner—Andrea Small
(74) Attorney, Agent, or Firm—Mollie M. Yang; David L. Rose

(57) ABSTRACT

Compounds of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of AIDS-related dementia, allergic conjunctivitis, allergic rhinitis, Alzheimer's disease, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, multiple myeloma, myocarditis, organ transplantation, psoriasis, pulmonary fibrosis, restenosis, retinitis, rheumatoid arthritis, septic arthritis, stroke, tumor metastasis, uveititis, and type I diabetes.

26 Claims, No Drawings

SUBSTITUTED NIPECOTYL DERIVATIVES AS INHIBITORS OF CELL ADHESION

This application claims priority under U.S. provisional application 60/213,155 filed on Jun. 22, 2000, which is hereby incorporated by reference in its entirety.

SUMMARY OF THE INVENTION

The compounds of the present invention are antagonists of the VLA-4 integrin ("very late antigen-4"; CD49d/CD29; or $\alpha_4\beta_1$), the $\alpha 4\beta 7$ integrin (LPAM-1 and $\alpha_4\beta_p$), and/or the $\alpha 9\beta 1$ integrin, thereby blocking the binding of VLA-4 to its various ligands, such as VCAM-1 and regions of fibronectin, $\alpha 4\beta 7$ to its various ligands, such as MadCAM-1, VCAM-1 and fibronectin, and/or $\alpha 9\beta 1$ to its various ligands, such as tenascin, osteopontin and VCAM-1. Thus, these antagonists are useful in inhibiting cell adhesion processes including cell activation, migration, proliferation and differentiation. These antagonists are useful in the treatment, prevention and suppression of diseases mediated by VLA-4-, $\alpha 4\beta 7$ -, and/or $\alpha 9\beta 1$ -binding and cell adhesion and activation, such as AIDS-related dementia, allergic conjunctivitis, allergic rhinitis, Alzheimer's disease, aortic stenosis, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, myocarditis, organ transplantation, psoriasis, restenosis, retinitis, rheumatoid arthritis, septic arthritis, stroke, tumor metastasis, type I diabetes, and vascular occlusion following angioplasty.

BACKGROUND OF THE INVENTION

The present invention relates to susbstituted cyclic amine derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, NY, 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of these cell types (see M. E. Hemler, "VLA Proteins in the Integrin Family: Structures, Functions, and Their Role on Leukocytes." *Ann. Rev. Immunol.* 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to proinflammatory cytokines (See A. J. H. Gearing and W. Newman, "Circulating adhesion molecules in disease.", *Immunol. Today*, 14, 506 (1993). The CS-1 domain is a 25 amino acid sequence that arises by alternative splicing within a region of fibronectin. (For a review, see R. O. Hynes "Fibronectins.", Springer-Velag, NY, 1990.) A role for VLA-4/CS-1 interactions in inflammatory conditions has been proposed (see M. J. Elices, "The integrin $\alpha_4\beta_1$ (VLA-4) as a therapeutic target" in *Cell Adhesion and Human Disease*, Ciba Found. Symp., John Wiley & Sons, NY, 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., *Proc. Natl. Acad. Sci. USA*, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., *Nature*, 363, 461 (1993); A. Hamann et al., *J. Immunol.*, 152, 3282 (1994)). MadCAM-1 can be induced in vitro by proinflammatory stimuli (See E. E. Sikorski et al. *J. Immunol.*, 151, 5239 (1993)). MadCAM-1 is selectively expressed at sites of lymphocyte extravasation and specifically binds to the integrin, $\alpha_4\beta_7$.

The $\alpha 9\beta 1$ integrin is found on airway smooth muscle cells, non-intestinal epithelial cells (see Palmer et al., *J. Cell Biol.*, 123, 1289 (1993)), and neutrophils, and, less so, on hepatocytes and basal keratinocytes (see Yokosaki et al., *J. Biol. Chem.*, 269,24144 (1994)). Neutrophils, in particular, are intimately involved in acute inflammatory repsonses. Attenuation of neutrophil involvement and/or activation would have the effect of lessening the inflammation. Thus, inhibition of $\alpha 9\beta 1$ binding to its respective ligands would be expected to have a positive effect in the treatment of acute inflammatory conditions.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." *Nature*, 356, 63 (1993) and E. Keszthelyi et al., "Evidence for a prolonged role of $\alpha_4$ integrin throughout active experimental allergic encephalomyelitis." *Neurology*, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." *J. Clin.*

*Invest.* 93, 776 (1993) and A. A. Y. Milne and P. P. Piper, "Role of VLA-4 integrin in leucocyte recruitment and bronchial hyperresponsiveness in the gunea-pig." *Eur. J. Pharmacol.*, 282, 243 (1995)); iii) adjuvant-induced arthritis in rats as a model of inflammatory arthritis (see C. Barbadillo et al., "Anti-VLA-4 mAb prevents adjuvant arthritis in Lewis rats." *Arthr. Rheuma.* (Suppl.), 36 95 (1993) and D. Seiffge, "Protective effects of monoclonal antibody to VLA-4 on leukocyte adhesion and course of disease in adjuvant arthritis in rats." *J. Rheumatol.*, 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", *J. Clin. Invest.*, 93, 1700 (1994), A. Jakubowski et al., "Vascular cell adhesion molecule-Ig fusion protein selectively targets activated α4-integrin receptors in vivo: Inhibition of autoimmune diabetes in an adoptive transfer model in nonobese diabetic mice." *J. Immunol.*, 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Tranplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts."*J. Clin Invest.*, 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin α-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of α4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996; xii) inhibition of TH2 T-cell cytokine production including IL-4 and IL-5 by VLA-4 antibodies which would attenuate allergic responses (J. Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas, including multiple myeloma; inflammatory lung disorders; acute respiratory distress syndrome (ARDS); pulmonary fibrosis; atherosclerotic plaque formation; restenosis; uveitis; and circulatory shock (for examples, see A. A. Postigo et al., "The $\alpha_4\beta_1$/VCAM-1 adhesion pathway in physiology and disease.",*Res. Immunol.*, 144, 723 (1994) and J. -X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren®, Athena Neurosciences/Elan) against VLA-4 in clinical development for the treatment of multiple sclerosis and Crohn's disease and a humanized monoclonal antibody (ACT-1®/LDP-02 Millenium/Genentech) against $\alpha_4\beta_7$ in clinical development for the treatment of inflammatory bowel disease. Several classes of antagonists of VLA-4 and α4β7 have been described (D. Y. Jackson et al., "Potent α4β1 peptide antagonists as potential anti-inflammatory agents",*J. Med. Chem.*, 40, 3359 (1997); H. N. Shroff et al., "Small peptide inhibitors of α4β7 mediated MadCAM-1 adhesion to lymphocytes", *Bioorg. Med. Chem. Lett.*, 6, 2495 (1996); K. C. Lin et al., "Selective, tight-binding inhibitors of integrin α4β1 that inhibit allergic airway responses",*J. Med. Chem.*, 42, 920 (1999); S. P. Adams and R. R. Lobb,"Inhibitors of Integrin Alpha 4 Beta 1 (VLA-4)." in Ann. Repts. in Medicinal Chemistry, Vol. 34, A. M. Doherty, Ed.; Acad. Press, NY, 1999, p. 179; U.S. Pat. No. 5,510,332, WO97/03094, WO97/02289, WO96/40781, WO96/22966, WO96/20216, WO96/01644, WO96/06108, WO95/15973, WO99/67230, WO00/00477, and WO00/01690). There are reports of nonpeptidyl inhibitors of the ligands for $\alpha_4$-integrins (WO99/36393, WO98/58902, WO96/31206); A. J. Soures et al., *Bioorg. Med. Chem. Lett.*, 8, 2297 (1998). There still remains a need for low molecular weight, specific inhibitors of VLA-4 and α4β7 -dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and α4β7 binding and cell adhesion and activation.

DETAILED DESCRIPTION OF THE INVENTION

The present invention provides novel compounds of formula I:

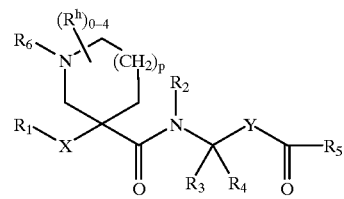

or a pharmaceutically acceptable salt thereof wherein:

X is

1) —S—,

2) —S(O)m—,

Y is
- 1) a bond, or
- 2) —C($R^7$)($R^8$)— m is an integer from 1 to 2;
n is an integer from 1 to 10;
p is a number chosen from 0, 1, 2, or 3;
$R^1$ is
- 1) hydrogen, provided X is S,
- 2) $C_{1-10}$alkyl,
- 3) $C_{2-10}$alkenyl,
- 4) $C_{2-10}$alkynyl,
- 5) Cy, or
- 9) —$NR^dR^e$,
  wherein alkyl, alkenyl and alkynyl are optionally substituted with one to four substituents selected from $R^a$, and Cy is optionally substituted with one to four substituents independently selected from $R^b$;

$R^2$ is
- 1) hydrogen,
- 2) $C_{1-10}$alkyl,
- 3) $C_{2-10}$alkenyl, and
- 4) $C_{2-10}$alkynyl,
  wherein alkyl, alkenyl and alkynyl are optionally substituted with one to four substituents independently selected from $R^a$;

$R^3$ is
- 1) $C_{1-10}$alkyl,
- 2) $Ar^1$,
- 3) $Ar^1$—$C_{1-10}$alkyl,
- 4) $Ar^1$—$Ar^2$,
- 5) $Ar^1$—$Ar^2$—$C_{1-10}$alkyl,
  wherein the alkyl group is optionally substituted with one to four substituents selected from $R^a$, and $Ar^1$ and $Ar^2$ are optionally substituted with one to four substituents independently selected from $R^b$, $R^4$ is
- 1) hydrogen,
- 2) $C_{1-10}$alkyl,
- 3) $C_{2-10}$alkenyl,
- 4) $C_{2-10}$alkynyl,
  wherein alkyl, alkenyl and alkynyl are optionally substituted with one to four substituents independently selected from $R^a$;

$R^5$ is
- 1) hydroxy,
- 2) $C_{1-10}$alkoxy,
- 3) $C_{2-10}$alkenyloxy,
- 4) $C_{2-10}$alkynyloxy,
- 5) Cy—O—,
- 6) Cy—$C_{1-10}$alkoxy,
- 7) amino,
- 8) $C_{1-10}$alkylamino,
- 9) di($C_{1-10}$alkyl)amino,
- 10) Cy—$C_{1-10}$alkylamino,
  wherein alkyl, alkenyl and alkynyl are optionally substituted with one to four substituents selected from $R^a$, and Cy is optionally substituted with one to four substituents independently selected from $R^b$;

$R^6$ is
- 1) hydrogen,
- 2) $C_{1-10}$ alkyl,
- 3) $C_{2-10}$ alkenyl,
- 4) $C_{2-10}$ alkynyl,
- 5) Cy
- 6) —$S(O)_mR^d$,
- 7) —$S(O)_mNR^dR^e$,
- 8) —$C(O)R^d$,
- 9) —$CO_2R^d$,
- 10) —$CO_2(CR^fR^g)_nCONR^dR^e$, or
- 11) —$C(O)NR^dR^e$,
  wherein alkyl, alkenyl and alkynyl are optionally substituted with one to four substituents independently selected from $R^a$, and Cy is optionally substituted with one to four substituents indepdently selected from $R^b$; or $R^6$ and an Rh attached to the carbon atom adjacent to the ring nitrogen together complete a 4–8 membered ring optionally containing one other heteroatom chosen from nitrogen, oxygen and sulfur;

$R^7$ is
- 1) hydrogen,
- 2) $C_{1-10}$ alkyl,
- 3) $C_{2-10}$ alkenyl,
- 4) $C_{2-10}$ alkynyl,
- 5) $Ar^1$,
- 6) $Ar^1$—$C_{1-10}$alkyl,
- 7) —$OR^d$,
- 8) —$O(cR^fR^g)_nNR^dR^e$,
- 9) —$OC(O)R^d$,
- 10) —$OC(O)NR^dR^e$,
- 11) halogen,
- 12) —$SR^d$,
- 13) —$S(O)_mR^d$,
- 14) —$S(O)_2OR^d$,
- 15) —$S(O)_mNR^dR^e$,
- 16) —$NO_2$,
- 17) —$NR^dR^e$,
- 18) —$NR^dC(O)R^e$,
- 19) —$NR^dS(O)_mR^e$,
- 20) —$NR^dC(O)OR^e$, or
- 21) —$NR^dC(O)NR^dR^e$,
  wherein alkyl, alkenyl, alkynyl and $Ar^1$ are optionally substituted with one to four substituents selected from a group independently selected from $R^c$;

$R^8$ is
- 1) hydrogen,
- 2) $C_{1-10}$ alkyl,
- 3) $C_{2-10}$ alkenyl,
- 4) $C_{2-10}$ alkynyl,
- 5) Cy, or
- 6) $Ar^1$—$C_{1-10}$alkyl,
  wherein alkyl, alkenyl, alkynyl, Cy and $Ar^1$ are optionally substituted with one to four substituents selected from a group independently selected from $R^c$;

$R^a$ is
- 1) halogen,
- 2) —$OR^d$,
- 3) —$OC(O)R^d$,
- 4) —$OC(O)NR^dR^e$,
- 5) —$O(CR^fR^g)_nNR^dR^e$,
- 6) —$SR^d$,
- 7) —$S(O)_mR^d$,
- 8) —$S(O)_2OR^d$,
- 9) —$S(O)_mNR^dR^e$,
- 10) —$NR^dR^e$,
- 11) —$NR^dC(O)R^e$,
- 12) —$NR^dC(O)OR^e$,
- 13) —$NR^dC(O)NR^dR^e$,
- 14) —$C(O)R^d$, 15) —CO$_2$R$^d$,
16) —C(O)NR$^d$R$^e$,
17) —CO$_2$(CR$^f$R$^g$)$_n$CONR$^d$R$^e$,
18) —CN,
19) —CR$^d$(N—OR$^e$),
20) —NO$_2$,
21) CF$_3$,
22) —OCF$_3$, or
23) Cy optionally substituted with one to four substituents independently selected from R$^c$;

R$^b$ is
1) a group selected from R$^a$,
2) C$_{1-10}$ alkyl,
3) C$_{2-10}$ alkenyl,
4) C$_{2-10}$ alkynyl, or
8) Ar$^1$—C$_{1-10}$alkyl,
   wherein alkyl, alkenyl, alkynyl and Ar$^1$ are optionally substituted with one to four substituents selected from a group independently selected from R$^c$;

R$^c$ is
1) halogen,
2) amino,
3) C$_{1-4}$alkylamino,
4) di(C$_{1-4}$alkyl)amino
5) carboxy,
6) cyano,
7) C$_{1-4}$alkyl,
8) arylC$_{1-4}$alkyl,
9) Ar$^1$,
10) hydroxy,
11) C$_{1-4}$alkoxy,
12) aryloxy, or
13) CF$_3$;

R$^d$ and R$^e$ are independently selected from hydrogen, C$_{1-10}$alkyl, C$_{2-10}$alkenyl, C$_{2-10}$alkynyl, Cy and Cy C$_{1-10}$alkyl, wherein alkyl, alkenyl, alkynyl and Cy are optionally substituted with one to four substituents independently selected from R$^c$; or R$^d$ and R$^e$ together with the atoms to which they are attached form a heterocyclic ring of 4 to 7 members containing 0–2 additional heteroatoms independently selected from oxygen, sulfur and nitrogen;

R$^f$ and R$^g$ are independently selected from hydrogen, C$_{1-10}$alkyl, Cy and Cy—C$_{1-10}$alkyl; or R$^f$ and R$^g$ together with the carbon to which they are attached form a ring of 4 to 7 members containing 0–2 heteroatoms independently selected from oxygen, sulfur and nitrogen;

R$^h$ is
1) a group selected from R$^a$,
2) C$_{1-10}$ alkyl,
3) C$_{2-10}$ alkenyl,
4) C$_{2-10}$ alkynyl,
5) Cy,
6) oxo,
   wherein alkyl, alkenyl, alkynyl, and Cy are optionally substituted with one to four substituents selected from a group independently selected from R$^c$; or two R$^h$ groups attached to adjacent ring atoms together complete 4–8 membered aromatic or non-aromatic ring containing 0–2 heteroatom selected from oxygen, sulfur and nitrogen; or two R$^h$ groups attached to the same ring atom together complete a 4–8 membered ring containing 0–2 heteroatom selected from oxygen, sulfur and nitrogen;

with the proviso that when R$^h$ is chosen from
1) —OR$^d$,
2) —OC(O)R$^d$,
3) —OC(O)NR$^d$R$^e$,
4) —O(CR$^f$R$^g$)$_n$NR$^d$R$^e$,
5) —SR$^d$,
6) —S(O)$_m$R$^d$,
7) —S(O)$_2$OR$^d$,
8) —S(O)$_m$NR$^d$R$^e$,
9) —NR$^d$R$^e$,
10) —NR$^d$C(O)R$^e$,
11) —NR$^d$C(O)OR$^e$,
12) —NR$^d$C(O)NR$^d$R$^e$, or
13) —NO$_2$,
14) halogen,
15) —CN, and
16) —CR$^d$(N—OR$^e$),
   it is not attached to an atom adjacent to the ring nitrogen;

Cy is cycloalkyl, heterocyclyl, aryl or heteroaryl;

Ar$^1$ and Ar$^2$ are independently selected from aryl and heteroaryl.

In one subset of compounds of formula I, X is S or SO$_2$. In one preferred embodiment X is S. In another preferred embodiment X is SO$_2$.

In another subset of compounds of formula I, Y is a bond.

In another subset of compounds of formula I, R$^1$ is C$_{1-10}$ alkyl optionally substituted with one to four substituents selected from R$^a$, or Cy optionally substituted with one to four substituents selected from R$^b$. In one preferred embodiment R$^1$ is C$_{1-5}$alkyl optionally substituted with one to two substituents selected from R$^a$; more prefereably R$^1$ is C$_{1-5}$alkyl optionally substituted with a group selected from NR$^d$R$^e$, NO$_2$, phenyl, hydroxy and 1-imidazolyl. In another preferred embodiment R$^1$ is aryl or heteroaryl each optionally substituted with one to two substituents selected from R$^b$; more preferably R$^1$ is phenyl optionally substituted with one or two substituents selected from halogen and NR$^d$R$^e$. Examples of R$^1$ include phenyl, 4-bromophenyl, 3-bromophenyl, 2-bromophenyl, 4-(benzylamino)phenyl, 3-(benzylamino)phenyl, 4-(1-pyrrolidinyl)phenyl, 3-(1-pyrrolidinyl)-phenyl, benzyl, 1-methyl-4-imidazolyl, 1-methyl-5-imidazolyl, methyl, 2-(1-piperidinyl)ethyl, 2-(4-morpholinyl)ethyl, 2-(3-(dimethylamino)propylamino) ethyl, 3-nitropropyl, 2-(1-imidazolyl)ethyl, and 2-hydroxyethyl.

In another subset of compounds of formula I, R$^2$ and R$^4$ are each hydrogen.

In another subset of compounds of formula I, R$^3$ is Ar$^1$—C$_{1-3}$alkyl or Ar$^1$—Ar$^2$—C$_{1-3}$alkyl; more preferably, R$^3$ is Ar$^1$—CH$_2$ or Ar$^1$—Ar$^2$—CH$_2$; Ar$^1$ and Ar$^2$ are each optionally substituted with one to four groups independently selected from Rb. Even more preferred R$^3$ is optionally substituted benzyl or optionally substituted Ar$^2$-benzyl, where Ar$^2$ is optionally substituted phenyl, or optionally substituted 5- or 6-membered heteroaryl. Even more preferred R$^3$ is benzyl, benzyl substituted with a group selected from hydroxy, C$_{1-5}$alkoxy, NHC(O)R$^e$, OC(O)NR$^d$R$^e$, and C(O)NR$^d$R$^e$, or 4-(Ar$^2$)-benzyl wherein Ar$^2$ is phenyl substituted with one to two groups selected from C$_{1-5}$alkyl, hydroxy, C$_{1-5}$alkoxy and NR$^d$R$^e$, or Ar2 is 2-ethyl-4-thiazolyl. Most preferably, R$^4$ is 4-(2',6'-dimethoxyphenyl)benzyl. Examples of R$^3$ inlude 4-(2'-methoxyphenyl)benzyl, 4-(2',6'-dimethoxyphenyl)benzyl, 4-(2'-cyanophenyl) benzyl, 4-(2'-cyano-6'-methoxyphenyl)benzyl, 4-(2'-hydroxy-6'-methoxyphenyl)benzyl, 4-(2'-dimethylamino-6'-methoxyphenyl)benzyl, 4-(2'-ethyl-6'-methoxyphenyl)

benzyl,benzyl, 4-hydroxybenzyl, 4-(2,6-dichlorobenzoylamino)benzyl, 4-(1-pyrrolidincarbonyloxy)benzyl, 4-(1-piperazinecarbonyl)benzyl, 4-(2-ethyl-4-thiazolyl)benzyl, 2-hydroxy-4-(2',6'-dimethoxyphenyl)benzyl and 2-nitro-4-(2',6'-dimethoxyphenyl)benzyl.

In another subset of compounds of formula I, $R^5$ is OH.

In another subset of compounds of formula I, $R^6$ is H or $C_{1-5}$alkyl. Preferably $R^6$ is hydrogen.

A preferred embodiment of formula I provides compounds of formula Ia:

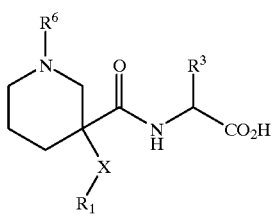

Ia wherein
X is
  1) S or
  2) $SO_2$;
$R^1$ is
  1) $C_{1-5}$alkyl optionally substituted with one to two substituents selected from $R^a$;
  2) aryl or heteroaryl each optionally substituted with one to two substituents selected from $R^b$;
$R^3$ is
  1) $Ar^1$—$C_{1-3}$alkyl, or
  2) $Ar^1$—$Ar^2$—$C_{1-3}$alkyl;
$R^6$ is
  1) hydrogen or
  2) $C_{1-5}$alkyl;
$R^a$, $R^b$, $Ar^1$ and $Ar^2$ are as defined above for formula I.

A more preferred embodiment of formula I provides compounds of formula Ib:

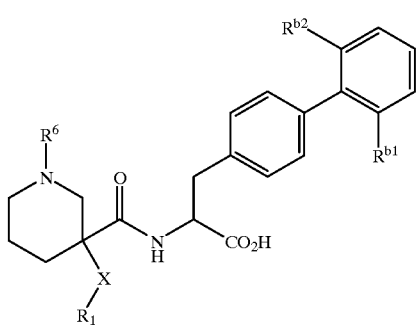

Ib wherein
X is
  1) S or
  2) $SO_2$;
$R^1$ is
  1) $C_{1-5}$alkyl optionally substituted with a group selected from $NR^dR^e$, $NO_2$, phenyl, hydroxy and 1-imidazolyl;
  2) phenyl optionally substituted with one or two substituents selected from halogen and $NR^dR^e$;

$R^6$ is
  1) hydrogen or
  2) $C_{1-5}$alkyl;
$R^{b1}$ and $R^{b2}$ are independently selected from
  1) hydrogen,
  2) $C_{1-5}$alkyl,
  3) hydroxy,
  4) $C_{1-5}$alkoxy and
  5) $NR^dR^e$;
$R^d$ and $R^e$ are as defined above for formula I.

A more preferred embodiment of formula I provides compounds of formula Ic:

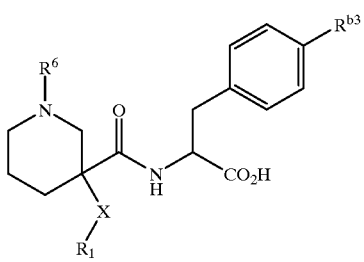

Ic wherein
X is
  1) S or
  2) $SO_2$;
$R^1$ is
  1) $C_{1-5}$alkyl optionally substituted with a group selected from $NR^dR^e$, $NO_2$, phenyl, hydroxy and 1-imidazolyl;
  2) phenyl optionally substituted with one or two substituents selected from halogen and $NR^dR^e$;
$R^6$ is
  1) hydrogen or
  2) $C_{1-5}$alkyl;
$R^{b3}$ is
  1) hydrogen,
  2) hydroxy,
  3) $C_{1-5}$alkoxy,
  4) $NHC(O)R^e$,
  5) $OC(O)NR^dR^e$, or
  6) $C(O)NR^dR^e$,
$R^d$ and $R^e$ are as defined above for formula I.

Examples of compounds of the present invention include:

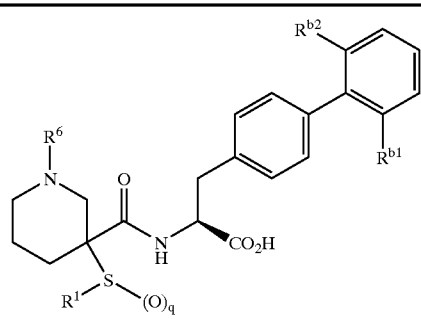

| Ex. | q | $R^1$ | $R^6$ | $R^{b1}/R^{b2}$ |
|---|---|---|---|---|
| 1/2 | 0 | Ph | H | H/OCH$_3$ |
| 3/4 | 0 | Ph | H | OCH$_3$/OCH$_3$ |
| 5/6 | 2 | Ph | H | H/OCH$_3$ |

-continued

| | | | | |
|---|---|---|---|---|
| 7/8 | 2 | Ph | CH₃ | H/OCH₃ |
| 9/10 | 2 | Ph | H | OCH₃/OCH₃ |
| 20/21 | 2 | 4-Br-Ph | H | OCH₃/OCH₃ |
| 22/23 | 2 | 3-Br-Ph | H | OCH₃/OCH₃ |
| 24/25 | 2 | 2-Br-Ph | H | OCH₃/OCH₃ |
| 26/27 | 2 | 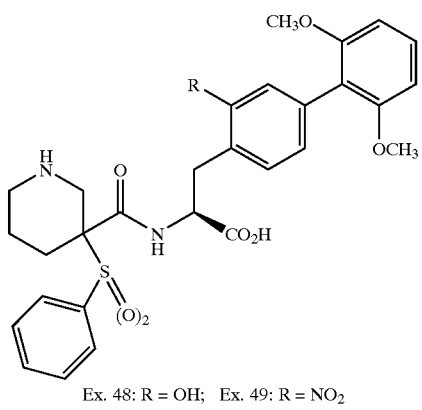 | H | OCH₃/OCH₃ |
| 28 | 2 | 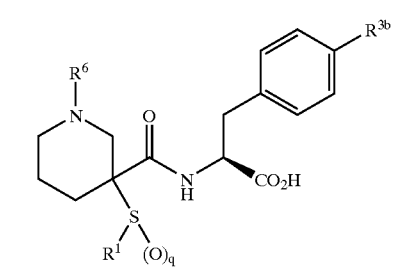 | H | OCH₃/OCH₃ |
| 29 | 2 | CH₃ | H | OCH₃/OCH₃ |
| 30/31 | 2 | 4-(PhCH₂NH)Ph | H | OCH₃/OCH₃ |
| 32/33 | 2 | 3-(PhCH₂NH)Ph | H | OCH₃/OCH₃ |
| 34/35 | 2 | 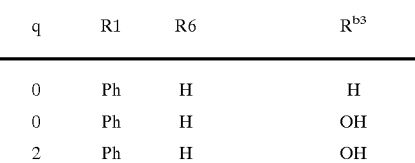 | H | OCH₃/OCH₃ |
| 36/37 | 2 | 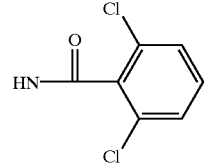 | H | OCH₃/OCH₃ |
| 38 | 2 | 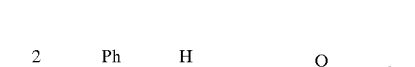 | H | OCH₃/OCH₃ |
| 39 | 2 |  | H | OCH₃/OCH₃ |
| 40 | 2 | (CH₃)₂N(CH₂)₃NH(CH₂)₂ | H | OCH₃/OCH₃ |
| 41 | 2 | NO₂(CH₂)₃ | H | OCH₃/OCH₃ |
| 42 | 2 |  | H | OCH₃/OCH₃ |
| 43 | 2 | HOCH₂CH₂ | H | OCH₃/OCH₃ |
| 44 | 2 | Ph | H | H/CN |
| 50/51 | 2 | Ph | H | OCH₃/CN |
| 52 | 1 | Ph | H | OCH₃/OCH₃ |
| 53 | 2 | Ph | H | OCH₃/N(CH₃)₂ |
| 54 | 2 | Ph | H | OCH₃/OH |
| 55 | 2 | Ph | H | OCH₃/CH₂CH₃ |
| 56 | 2 | PhCH₂ | H | OCH₃/OCH₃ |

-continued

Ex. 48: R = OH;   Ex. 49: R = NO₂

| Ex | q | R1 | R6 | R^{b3} |
|---|---|---|---|---|
| 14/15 | 0 | Ph | H | H |
| 16/17 | 0 | Ph | H | OH |
| 18/19 | 2 | Ph | H | OH |
| 45 | 2 | Ph | H | 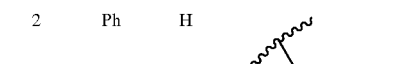 |
| 46/47 | 2 | Ph | H |  |
| 57/58 | 2 | Ph | H |  |
| 59/60 | 2 | Ph | H |  |

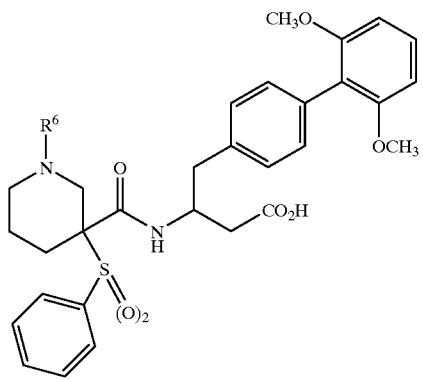

Ex. 11/12: $R^6$ = t-BOC;  Ex. 13: $R^6$ = H

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha 4\beta 7$ integrin makes them useful for preventing or reversing the symptoms, disorders or diseases induced by the binding of VLA-4 and or $\alpha 4\beta 7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha 4\beta 7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, and (19) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |

| -continued | |
|---|---|
| Magnesium Stearate | 1.5 |
| | 600 |

| Aerosol | Per canister |
|---|---|
| Compound of Formula I | 24 mg |
| Lecithin, NF Lq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib and rofecoxib; (h) inhibitors of phosphodiesterase type IV (PDE-IV) such as Ariflo and roflumilast; (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, rosiglitazone, MCC-555, BRL49653 and the like); (l) preparations of interferon beta (interferon beta-1a, interferon beta-1b); (m) anticholinergic agents such as muscarinic antagonists (ipratropium bromide and tiotropium bromide) and selective muscarinic M3 receptor antagonists such as those described in U.S. Pat. No. 5,948,792; (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In the first method (Scheme 1), a resin-based synthetic strategy is outlined where the resin employed is represented by the ball (○). An N-FMOC-protected amino acid derivative A (FMOC=fluorenyl-methoxycarbonyl) is loaded onto an appropriate hydroxyl-containing resin (the choice of resin being dependent on type of linker used, in this case Wang resin was utilized) using 1-ethyl-3-(3'-dimethylaminopropyl)carbodiimide (EDC) and 1-hydroxybenzotriazole (HOBt) in a solvent such as methylene chloride ($CH_2Cl_2$) and tetrahydrofuran (THF) or dimethylformamide (DMF) to give B. The FMOC protecting group is removed with piperidine in DMF to yield free amine C. A nipecotic acid derivative D is then coupled to the amine using a reagent such as 2-(1H-benzotriazole-1-yl)-1,1,3,3-tetramethyluronium hexafluorophosphate (HBTu) in the presence of HOBt and diisopropyl ethyl amine (DIEA) or any of the other well known amide coupling reagents under appropriate conditions: EDC, DCC or BOP (benzotriazole-1-yl-oxy-tris-(dimethylamino)-phosphoniumhexafluorophosphate) to give E. The final product is removed from the resin with strong acid (in this instance, trifluoroacetic acid (TFA in the presence of 5% water) to yield compounds of the present invention F.

Scheme 1

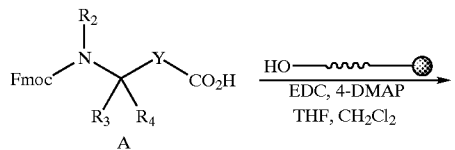

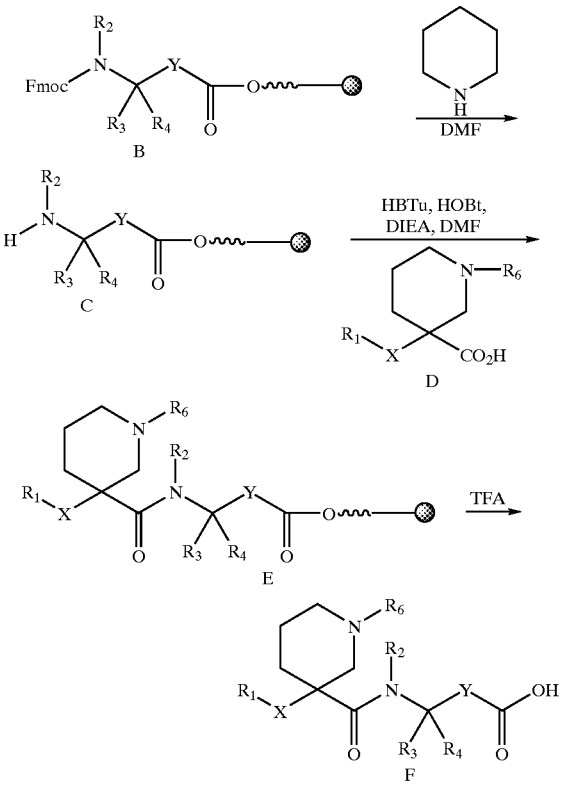

In the second method (Scheme 2), standard solution phase synthetic methodology is outlined. Many amino acid derivatives are commercially available as the tert-butyl or methyl esters and may be used directly in the synthesis outlined below. Amino acid tert-butyl esters B may be prepared from amino acids C directly by treament with isobutylene and sulfuric acid in diglyme or dioxane. Alternatively, N-Boc-protected amino acid derivative A (Boc=tert-butyloxycarbonyl) is treated with tert-butyl 2,2,2-trichloroacetimidate in the presence of boron trifluoride etherate ($BF_3$-$Et_2O$) followed by treatment with strong acid (HCl in ethyl acetate or sulfuric acid in tert-butyl acetate) to remove the t-BOC group to yield tert-butyl ester B which is subsequently coupled to carboxylic acid D in the presence of EDC, HOBt, and DIEA in methylene chloride to yield amide E. The ester is then hydrolysed (in the case of tert-butyl ester with 50% TFA in methylene chloride and for the methyl ester by treatment with 1N sodium hydroxide solution in methanol or dioxane) to provide compounds of the present invention F.

Scheme 2

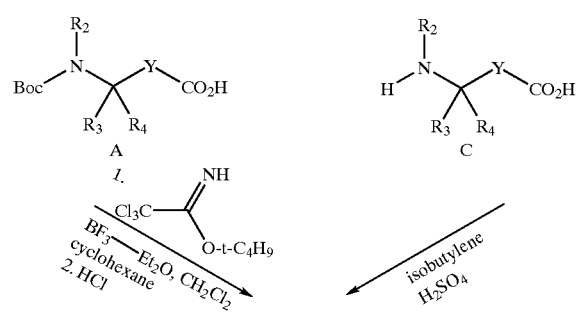

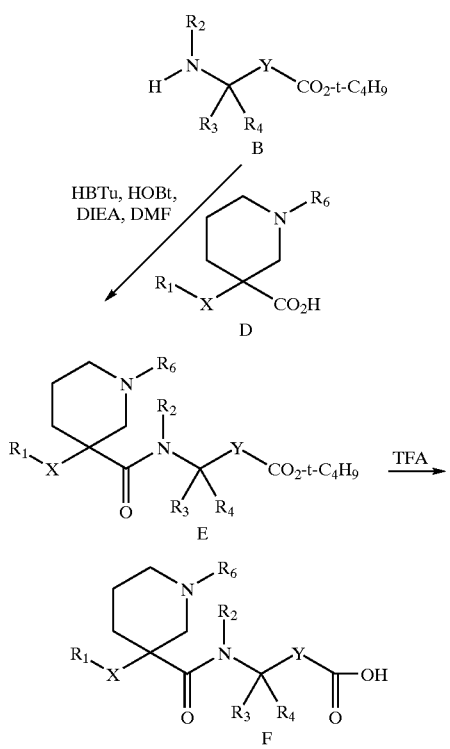

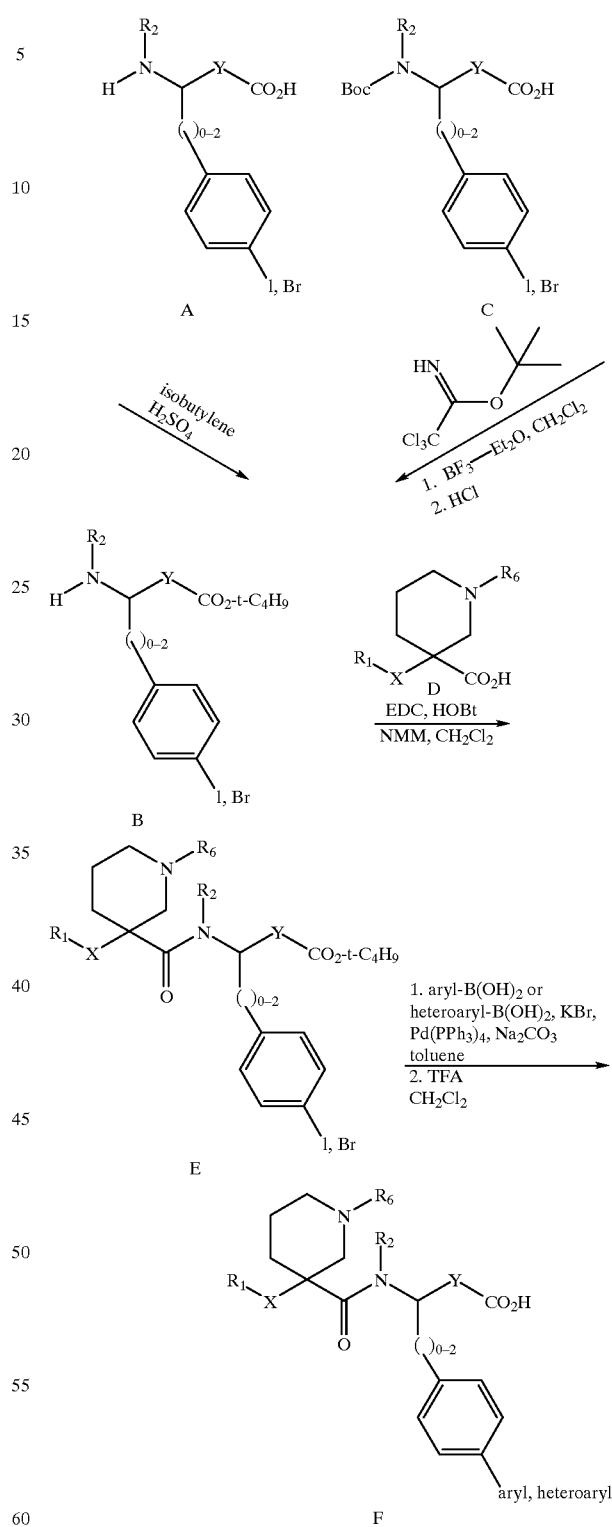

Scheme 3

Note: Methyl or ethyl esters may be used in place of t-butyl esters. E to F by treatment with 1 equiv. NaOH or KOH.

In a third method (Scheme 3), a late stage intermediate aryl bromide or iodide is coupled to an appropriately substituted aryl or heteroaryl boronic acid to give a subset of compounds of the present invention ($R_3$ =biaryl-substituted-alkyl or heteroaryl-aryl-substituted-alkyl, $R_2$ =hydrogen). For example, 4-iodo or 4-bromo-phenyl-derivative A is converted to the tert-butyl ester B by treatment with isobutylene and sulfuric acid. Alternatively the N-Boc-4-iodo- or 4-bromo-phenyl-derivative C is reacted with tert-butyl 2,2,2-trichloroacetimidate in the presence of boron trifluoride etherate in methylene chloride-cyclohexane followed by treatment with strong acid (HCl in ethyl acetate or sulfuric acid in tert-butyl acetate) to remove the t-BOC group to yield tert-butyl ester B which is subsequently coupled with D in the presence of (for example) EDC, HOBt and NMM to yield amide E. Substituted aryl or heteroaryl boronic acids are coupled to E in the presence of a palladium(0) reagent, such as tetrakis(triphenylphosphine)palladium under Suzuki conditions (N. Miyaura et al., *Synth. Commun.*, 1981, 11, 513–519), followed by removal of the tert-butyl ester using a strong acid (TFA) to yield the desired product F. If the aryl or heteroaryl boronic acid is not commercially available, but the corresponding bromide or iodide is, then the bromide or iodide can be converted into the desired boronic acid by treatment with an alkyllithium reagent in tetrahydrofuran at low temperature followed by addition of trimethyl or triisopropyl borate. Hydrolysis to the boronic acid can be effected by treatment of the intermediate with aqueous base and then acid.

Alternatively, the aryl coupling reaction may be performed by application of Stile-type carbon-carbon bond forming conditions (Scheme 4). (A. M. Echavarren and J. K. Stille, *J. Am. Chem. Soc.* 1987, 109, 5478–5486). The aryl bromide or iodide intermediate A is converted into its trialkyltin derivative B using hexamethylditin $(((CH_3)_3Sn)_2)$ in the presence of a palladium(0) catalyst and lithium chloride and then reacted with an appropriately substituted aryl or heteroaryl bromide, iodide, or triflate in the presence of a palladium reagent, such as tetrakis(triphenylphosphine)palladium(0) or tris(dibenzylideneacetone)dipalladium(0), in a suitable solvent, such as toluene, dioxane, DMF, or 1-methyl-2-pyrrolidinone, followed by the removal of the tert-butyl ester using strong acid (TFA) to yield the desired product C. Biphenyl amino acids suitable for attachment to resin (Scheme 1, A) may be prepared by this route as well. Superior coupling conversions and rates may be elicited by application of the method of Farina (*J. Org. Chem.* 5434, 1993)

aliphatic iodo intermediate A in carbon-carbon bond formation using zinc/copper couple and palladium(II) (M. J. Dunn et al., *SYNLETT* 1993, 499–500).

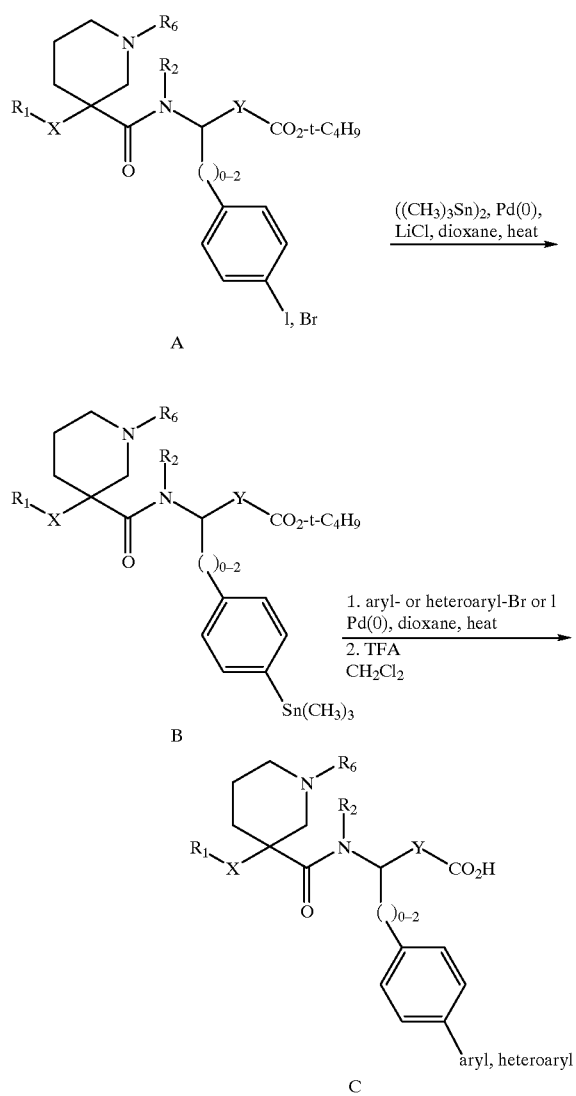

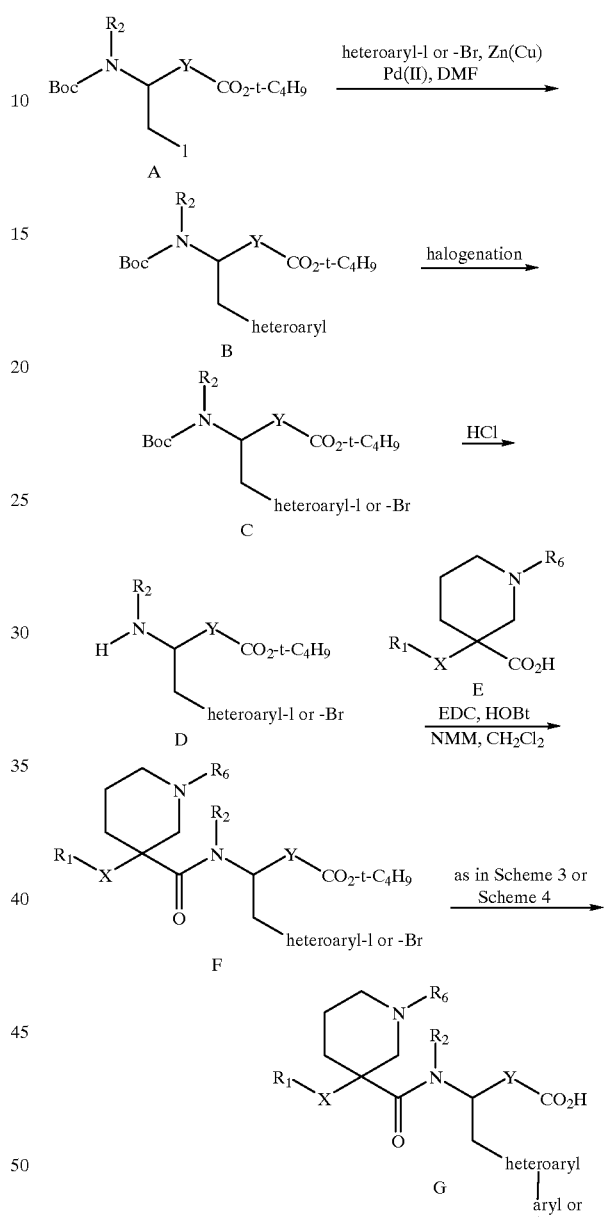

Compounds wherein the proximal ring is heteroaryl (G) may be prepared (Scheme 5) in a similar fashion starting from the appropriate heteroaryl bromide or iodide C using Suzuki-type conditions as depicted in Scheme 3 or from the corresponding heteroaryl trimethyltin using Stille-type conditions as depicted in Scheme 4. The requisite heteroaryl halides C may be prepared via conventional electrophilic halogenation of the N-Boc-heteroaryl-alanine tert-butyl ester intermediate B. B may be prepared from the known 3-Substituted nipecotic acid derivatives may be prepared first by treatment of a nipecotic acid ester A with strong base such as sodium hexamethyldisilazide ($Na^+$ $((CH_3)_3Si)_2N^-$) or lithium diisopropylamide (LDA) followed by addition of an appropriate thiolating agent to yield B or D (Scheme 6). Deprotection of the ester would follow as described: TFA for a tert-butyl ester or hydroxide treatment for methyl or ethyl ester to yield C. To prepare the sulfone, treatment of C with a peracid would yield E. Alternatively, A could be treated with a sulfonylating agent such as a sulfonylfluoride followed by ester hydrolysis to yield E.

Scheme 6

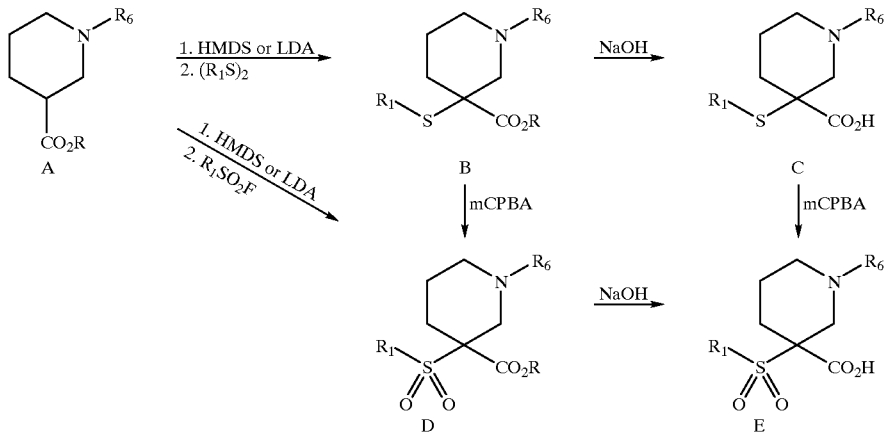

Abbreviations
Ac$_2$O: acetic anhydride
BF$_3$—Et$_2$O: borontrifluoride etherate
Bn: benzyl
BOC: tert-butyloxycarbonyl
BOC—ON 2-(tert-butoxycarbonyloxyimino)-2-phenylacetonitrile
BOP: benzotriazol-1-yloxy-tris (dimethylamino)-phosphonium hexafluorophosphate
t-Bu$_3$P: tri-tert-butylphosphine
CBZ: benzyloxycarbonyl
CH$_2$Cl$_2$: methylene chloride
CH$_3$CN: acetonitrile
CH$_3$NO$_2$: nitromethane
CsOH: cesium hydroxide
Cy$_3$P: tricyclohexylphosphine
DIBAL-H: diisobutylaluminum hydride
DBU: 1,8-diazobicyclo[5.4.0]undec-7-ene
DCC: dicyclohexylcarbodiimide
DEA: N,N-diisopropylethylamine
DMAP: 4-(dimethylamino)pyridine
DMF: dimethylformamide
DMSO: dimethylsulfoxide
EDC: 1-(ethyl)-3-(3-dimethylaminopropyl)-carbodiimide hydrochloride
Et: ethyl
EtOAC: ethyl acetate
EtOH: ethanol
FMOC: 9-fluorenylmethoxylcarbonyl
H$_2$SO$_4$: sulfuric acid
HATU: O-(7-azabenzotriazol-1-yl)-1,1,3,3-tetramethyluronium hexafluorophosphate
HBTU: O-(benzotriazole-1-yl)-1,1,3,3-tetramethyluronium hexafluorophosphate
HCl: hydrochloric acid
HOAt: 1-hydroxy-7-azabenzotriazole
HOBt: 1-hydroxybenzotriazole
HPLC: high pressure liquid chromatography
K$_2$CO$_3$: potassium carbonate
KF: potassium fluoride
KI: potassium iodide
LDA: lithium diisopropylamide
m-CPBA: meta-chloroperbenzoic acid
Me: methyl
MeOH: methanol
MgSO$_4$: magnesium sulfate
mmol: millimole
MPLC: medium pressure liquid chromatography
MsCl: methanesulfonyl chloride
NaHCO$_3$: sodium bicarbonate
NaOH: sodium hydroxide
NBS: N-bromosuccinimide
Pd$_2$dba$_3$: tris(di benzylideneacetone) dipalladium(0)
Ph: phenyl
Ph$_3$P: triphenylphosphine
PyBOP: (benzotriazol-1-yloxy)tripyrrolidinophosphonium hexafluorophosphate
TBAF: tetrabutylammonium fluoride
TBSCl: tert-butyldimethylsilyl chloride
TEA: triethylamine
TFA: trifluoroacetic acid
THF: tetrahydrofuran
TLC: thin layer chromatography
TMSCHN$_2$: trimethylsilyldiazomethane

REFERENCE EXAMPLE 1

(L)-4-(2'-Cyanophenyl)phenylalanine, methyl ester hydrochloride.

Step A (L)-4-Iodophenylalanine, methyl ester hydrochloride.

Thionyl chloride (3.6 mL, 50 mmol) was slowly added dropwise to a stirred flask containing methanol (6 mL) at 0° C. After the addition, solid N-BOC-(L)-4-iodophenylalanine (3.9 gm, 10 mmol) was added followed by more methanol (10 mL). The mixture was refluxed for 1.5 hr and then cooled to room temperature. The solution was taken to dryness by rotoevaporation and ether (20 mL) and heptane (5 mL) were added. The suspension was again taken to dryness by rotoevaporation and used in the subsequent reaction.

Step B

N-BOC-(L)-4-1odophenylalanine, methyl ester.

The product from Step A (10 mmol) was suspended in THF (20 mL) and methylene chloride (10 mL) at room temperature and triethylamine (2.1 mL, 11 mmol) was added. BOC-ON (2.7 gm, 11 mmo) was added and the solution stirred at room temperature for 5.5 hr. The solution was poured into a mixture of water (100 mL) and EtOAc (100 mL) and separated. The aqueous portion was extracted with EtOAc (2×50 mL). The combined organic extracts were washed successively with 5% citric acid (50 mL), saturated sodium bicarbonate solution (50 mL), and brine (50 mL) and dried over anhydrous magnesium sulfate. The mixture was filtered and concentrated to an oily residue which was dissolved in ether (50 mL) and placed in a freezer overnight. As no crystals precipitated, the solution was azeotroped with hexanes (2×50 mL) and the residue purified by flash column chromatography on silica gel eluted with 10% EtOAc in hexanes. Concentration of the chromatography fractions yielded N-BOC-(L)-4-iodophenylalanine, methyl ester (3.1 gm).

Step C

N-BOC-(L)-4-(Trimethylstannyl)phenylalanine, methyl ester.

To a degassed solution of N-BOC-(L)-4-iodophenylalanine, methyl ester (3.1 gm, 7.6 mmol), hexamethylditin (2.2 mL, 11.4 mmol), lithium chloride (0.5 gm, 11.4 mmol), and triphenylphosphine (40 mg, 0.2 mmol) in dioxane was added tetrakis(triphenylphosphine)palladium (II) (0.44 gm, 0.4 mmol). The solution was heated to 95° C. overnight under a dry nitrogen atmosphere. The solution was cooled to room temperature and diluted with EtOAc (100 mL) and successively washed with saturated sodium bicarbonate solution and saturated brine. The solution was dried over anhydrous magnesium sulfate, filtered, and concentrated with dry silica gel. The dry powder was placed on a silica gel column and the product purifed by flash column chromatography eluted with 10% EtOAc in hexanes to yield N-BOC-(L)-4-(trimethyl-stannyl)phenylalanine, methyl ester (1.5 gm).

Step D

N-BOC-(L)-4-(2'—Cyanophenyl)phenylalanine, methyl ester.

To a degassed solution of N-BOC-(L)-4-(trimethylstannyl)phenylalanine, methyl ester (1.4 gm, 3.2 mmol) and 2-bromobenzonitrile (1.2 gm, 6.3 mmol) in DMF (8 mL) was added bis(triphenylphosphine)palladium(II) chloride (224 mg, 0.32 mmol). The stirred mixture was placed into a preheated oil bath (90° C.) and stirred for 3.5 hr. Heating was stopped and the solution allowed to cool. The solvent was removed by rotoevaporation and the residue dissolved in methylene chloride. The product was purifed on silica gel using a Biotage flash column chromatography apparatus eluted with 15% EtOAc in hexanes to yield N-BOC-(L)-4-(2'-cyanophenyl)phenylalanine, methyl ester (0.5 gm).

Step E (L)-4-(2'-Cyanophenyl)phenylalanine, methyl ester hydrochloride.

Acetyl chloride (2 mL) was slowly added to a suspension of N-BOC-(L)-4-(2'-cyanophenyl)phenylalanine, methyl ester (0.5 gm, 1.3 mmol) in methanol (10 mL). The solution was stirred overnight at room temperature. The solvent was removed by rotoevaporation to yield (L)-4-(2'-cyanophenyl) phenylalanine, methyl ester hydrochloride (0.75 gm).

REFERENCE EXAMPLE 2

(L)-4-(2'-Cyanophenyl)phenylalanine, Tert-butyl Ester Hydrochloride

Step A

N-BOC-(L)-4-lodophenylalanine, tert-butyl ester.

To a suspension of N-BOC-(L)-4-iodophenylalanine (BACHEM, 5.0 gm, 12.8 mmol) in methylene chloride (35 mL) and cyclohexane (70 mL) was added tert-butyl-2,2,2-trichloroacetimidate (2.93 gm, 13.4 mmol) followed by boron trifluoride (0.24 mL). The suspension was stirred at room temperature for 2 hr after which starting material still remained. Additional tert-butyl-2,2,2-trichloroacetimidate (2.93 gm, 13.4 mmol) and boron trifluoride (0.24 mL) were added and the reaction mixture stirred at room temperature for four days. A third addition of tert-butyl-2,2,2-trichloroacetimidate (2.93 gm, 13.4 mmol) and boron trifluoride (0.24 mL) were added and the reaction mixture stirred at room temperature for 3 hr. The mixture was filtered through a Celite filter pad which was subsequently washed with fresh methylene chloride:cyclohexane (1:1, 2×25 mL). The solvent was removed by rotoevaporation and the residue purified by flash column chromatography on silica gel eluted with 10% ether in hexane to yield N-BOC-(L)-4-iodophenylalanine, tert-butyl ester as a white crystalline solide (3.3 gm).

Step B (L)-4-(2'-Cyanophenyl)phenylalanine, tert-butyl ester hydrochloride.

N-BOC-(L)-4-iodophenylalanine, tert-butyl ester was converted to the title compound by the procedures described in Reference Example 1, Steps C through E.

REFERENCE EXAMPLE 3

(L)-4-(2'-Methoxyphenyl)phenylalanine, Tert-butyl Ester

Step A

N-(BOC)-(L)-4-(2'-Methoxyphenyl)phenylalanine, tert-butyl ester.

N-BOC-(L)-4-iodophenylalanine, tert-butyl ester (7.97 g (0.018 mol) was dissolved in 2:1 toluene:ethanol (160 mL). To this solution was added 2-methoxyphenylboronic acid (2.99 g, 20 mmol), tetrakistriphenylphosphine palladium(0) (0.69 g, 0.60 mmol) and a 2.0 M aqueous solution of sodium carbonate (22.7 mL, 0.45 mol). The reaction mixture was degassed three times and then heated at 90° C. for 90 minutes at which time the reaction mixture turned black. The mixture was diluted with ethyl acetate (300 mL), washed with water (3×150 mL) and brine (2×100 mL), and dried over anhydrous $MgSO_4$. The mixture was filtered and concentrated in vacuo. The residue was purified by flash column chromatography on silica gel eluted with 10% EtOAc in hexanes to give 6.89 g (88% yield) of N-(BOC)-(L)-4-(2'-methoxyphenyl)phenylalanine, tert-butyl ester as a white solid.

300 MHz $^1$H NMR ($CDCl_3$): δ 1.45 (s, 18H); 3.10 (d, 2H); 3.80 (s, 3H); 4.5 (dd, 2H); 5.1 bd, 1H); 7.0 (m, 2H); 7.22 (d, 2H); 7.30 (d, 2H); 7.49 (d, 2H); 7.62 (d, 2H).

Step B (L)-4-(2'-Methoxyphenyl)phenylalanine, tert-butyl ester HCl.

N-(BOC)-(L)-4-(2'-methoxyphenyl)phenylalanine, tert-butyl ester (8.64 g, 20 mmol) was dissolved in tert-butyl acetate (150 mL) and concentrated sulfuric acid (9.8 g, 100 mmol) was added thereto. The reaction mixture was stirred for 3 hours at room temperature and then diluted with ethyl acetate (150 mL). Addition of 1N NaOH was continued until the solution was basic. The aqueous phase was extracted with EtOAc (4×100 mL) and the combined organic phases were dried over anhydrous $MgSO_4$, filtered and concentrated in vacuo. The residue was dissolved in 100 mL of ether and treated with anhydrous HCl gas with cooling to give a white solid. The solid was recovered by filtration to give 5.8 g of (L)-4-(2'-methoxyphenyl)phenylalanine, tert-butyl ester hydrochloride. 400 MHz $^1$H-NMR ($CD_3OD$): 1.42 (s, 9H); 3.20 (d, 2H); 3.79 (s, 3H); 4.20 (t, 1H); 7.00 (t, 1H); 7.06 (d, 1H); 7.25 (dd, 1H); 7.32 (m, 3H); 7.50 (d, 2H).

REFERENCE EXAMPLE 4

(L)-4-[2',6'-(Dimethoxyphenyl)]phenylalanine, Tert-butyl Ester Hydrochloride

Step A

N-(BOC)-4-[(Trifluoromethylsulfonyl)oxy]-(L)-phenylalanine, tert-butyl ester.

To a solution of of N-(BOC)-(L)-tyrosine, tert-butyl ester (18.5 g, 55 mmol) in 150 mL of dry methylene chloride was added pyridine (17.4 g, 220 mmol) followed at 0° C. by the dropwise addition of of neat triflic anhydride (18.6 g,66 mmol). The reaction mixture was stirred at 0° C. and monitored by TLC. After 4 hours, the mixture was diluted with 200 mL of methylene chloride, and washed successively with 1N HCl (3×100 mL), saturated sodium bicarbonate (2×100 mL) and brine (1×50 mL). The solution was dried over anhydrous $MgSO_4$, filtered and concentrated in vacuo to give N-(BOC)-4-[(trifluoromethylsulfonyl)oxy]-(L)-phenyl-alanine, tert-butyl ester as an oil which was used without further purification.

Step B

N-(BOC)-(L)-4-[2',6'-(Dimethoxyphenyl)]phenylalanine, tert-butyl ester, hydrochloride.

N-(BOC)-4-[(trifluoromethylsulfonyl)oxy]-(L)-phenylalanine, tert-butyl ester (Step A) was dissolved in a mixture of 125 mL of toluene and 61 mL of ethanol. To this solution was added 2,6-dimethoxyboronic acid (11.3 g, 62 mmol) and palladium tetrakistriphenylphosphine (2.5 g). The solution was treated with potassium carbonate (18.3 g, 133 mmol) dissolved in 30 mL of water. The mixture was heated to reflux over 4 hours, cooled to room temperature, and then diluted with 200 mL of ethyl acetate. The solution was washed with water (3×75 mL) and brine (1×75 mL), dried over anhydrous $MgSO_4$, filtered and concentrated in vacuo. The residue was purified by flash column chromatography on silica gel eluted with a gradient of 5–20% EtOAc in hexanes to provide 14.7 g of N-(BOC)-(L)-4-[2',6'-(dimethoxyphenyl)]phenylalanine, tert-butyl ester, hydrochloride as a white solid.

Step C (L)-4-(2',6'-(Dimethoxyphenyl)-phenylalanine, tert-butyl ester hydrochloride.

N-(BOC)-(L)4-(2',6'-(dimethoxyphenyl)-phenylalanine, tert-butyl ester, hydrochloride (Step B) was dissolved in 350 mL of tert-butyl acetate at 0° C. and was treated with 8.3 mL of concentrated sulfuric acid. The cold bath was removed and after one hour TLC indicated only starting material was present. The reaction mixture was cooled in an ice bath once more and treated with 3.4 mL of concentrated sulfuric acid. The reaction was monitored by TLC. After consumption of the starting material the reaction mixture was diluted with 300 mL of ethyl acetate and was washed with 3×100 mL of 1N NaOH followed by brine (1×100 mL). The solution was dried over anhydrous $MgSO_4$, filtered and concentrated in vacuo to provide 8.9 g of (L)-4-[2',6'-(dimethoxyphenyl)]phenylalanine, tert-butyl ester hydrochloride.

500 MHz $^1$H NMR ($CD_3OD$): δ 1.45 (s, 9H), 3.20 (d, 2H); 3.69 (s, 6H); 4.20 (t, 1H); 6.72 (d, 2H), 7.15 (m. 5H).

REFERENCE EXAMPLE 5

3(R)-Amino-3-(4-biphenyl)propionic Acid, Methyl Ester

Step A

N-(BOC)-(S)-4-Hydroxyphenylglycine.

To a solution of (S)-(4-hydroxyphenyl)glycine (Sigma Chemical, 6.5 g, 39 mmol) in dioxane/water (1:1, 120 mL) was added triethylamine (5.9 g, 8.2 mL, 58 mmol) and [2-(tert-butoxycarbonyloxyimino)-2-phenylacetonitrile] (BOC-ON; 11 g, 45 mmol). After stirring overnight at room temperature, 300 mL of brine was added to the solution and the mixture was extracted with ether (3×100 mL). The aqueous layer was acidified with HCl (pH=2) and extracted with 3×100 mL of ethyl acetate. The ethyl acetate layer was dried over anhydrous $MgSO_4$, filtered and the solvent removed under reduced pressure. The residue was purified by flash column chromatography eluted with a gradient of 2–5% methanol in methylene chloride to yiled 12 g of crude N-(BOC)-(S)-4-hydroxyphenylglycine. An impurity was removed following esterification of the product in the next step.

400 MHz $^1$H NMR ($CDCl_3$): δ 1.37 (s, 9H), 5.1 (1H, br s), 6.7 (d, 2H, J=8 Hz), 7.15 (d, 2H, J=8 Hz).

Step B

N-(BOC)-(S)-4-hydroxyphenylglycine, methyl ester.

In a 50 mL round bottomed flask was added a 1:1 mixture of benzene:methanol and N-(BOC)-(S)-4-hydroxyphenylglycine (2.8 g, 11 mmol). The solution was cooled to 0° C. and a 2 M solution of trimethylsilyldiazomethane (Aldrich Chemical Co.) in hexane was added with vigorous stirring until a slight yellow color persisted. The solvents were removed under reduced pressure and the crude product was purified by flash column chromatography (20% EtOAc in hexanes) to give N-(BOC)-(S)-4-hydroxyphenylglycine, methyl ester (2.05 g, 7.3 mmol) (66% yield).

300 MHz $^1$H NMR ($CDCl_3$): δ 1.43 (s, 9H), 3.71 (s, 3H), 5.22 (br d, 1H), 5.57 (1H, br d), 5.80 (br s, 1H), (6.7 (d, 2H, J=8 Hz), 7.17 (d, 2H, J=8 Hz).

Step C

N-(BOC)-(S)-4-[(Trifluoromethylsulfonyl)oxy]phenylglycine. methyl ester.

To a 25 mL round bottom flask fitted with a stir bar and septum was added N-(BOC)-(S)-4-hydroxyphenylglycine, methyl ester (1.9 g, 6.8 mmol) and pyridine (2.8 mL, 33 mmol) in 12 mL methylene chloride. The flask was purged with $N_2$, cooled to 0° and trifluoromethanesulfonic anhydride (1.38 mL, 7.8 mmol) was added dropwise over several minutes, keeping the temperature at or below 4° C. The solution was stirred for 1 h, then at room temperature for 4 h. The mixture was diluted with 20 mL of methylene chloride, washed with 20 mL of 0.5 N NaOH, 1×20 mL of water and 2×20 mL of 10% citric acid. The organic layer was dried over anhydrous $MgSO_4$, filtered, and the solvents removed by evaporation in vacuo. The residue was purified by flash column chromatography on silica gel eluted with 25% methylene chloride in hexane to give 2.3 g of N-(BOC)-(S)-4-[(trifluoromethylsulfonyl)oxy]phenylglycine, methyl ester. (81% yield).

300 MHz $^1$H NMR ($CDCl_3$): δ 1.43 (s, 9H), 3.74 (s, 3H), 5.35 (1H, br d), 5.68 (br s, 1H), 7.27 (d, 2H, J=8 Hz), 7.47 (d, 2H, J=8 Hz).

Step D

N-(BOC)-(S)-(4-Biphenyl)glycine.

To a 25 mL round bottom flask fitted with a stir bar and septum was added N-(BOC)-(S)-4-[(trifluoromethylsulfonyl)oxy]phenylglycine, methyl ester (690 mg, 1.67 mmol), anhydrous potassium carbonate (348 mg, 2.6 mmol) and benzene-boronic acid (411 mg, 3.4 mmol) in 15 mL of toluene and 3 mL of ethanol. The mixture was degassed under nitrogen with three freeze-thaw cycles and tetrakis(triphenylphosphine) palladium (94 mg, 0.085 mmol) was added to the reaction mixture and the mixture was heated between 75–90° C. for 4 h. The solvent was removed under reduced pressure and the residue purified by flash column chromatography on silica gel eluted with 15% EtOAc in hexane to give 600 mg of N-(BOC)-(S)-(4-biphenyl)glycine, methyl ester.

300 MHz $^1$H NMR (CDCl$_3$): δ 1.44 (s, 9H), 3.75 (s, 3H), 5.37 (1H, br d), 5.62 (br s, 1H), 7.36 (m, 1H), 7.45 (m, 4H), 7.57 (m, 4H).

The ester was hydrolyzed with 1.2 eq of KOH in 10 mL of 4:1 ethanol:water (2 h). The solution was acidified with 2 N HCl (pH=2). Solvent was removed in vacuo and the free acid was extracted with methylene chloride to provide 430 mg of N-(BOC)-(S)-(4-biphenyl)glycine (66% yield).

Step E 3-(BOC)amino-1-diazo-3-(4-biphenyl)propan-2-one.

To a 25 mL round bottom flask fitted with a stir bar and septum was added N-(BOC)-(S)-4-biphenylglycine (430 mg, 1.31 mmol) in 10 mL of 2:1 methylene chloride: ether. The mixture was cooled to 0° C. and N-methylmorpholine (159 μl, 1.44 mmol) was added, followed by dropwise addition of isobutyl chloroformate (179 μL, 1.38 mmol). The mixture was stirred for 1 h at 0° C., then diazomethane in ether (excess, prepared from Diazald® by literature procedure) was added dropwise to the reaction mixture. The mixture was stirred for 1 hr then quenched with saturated sodium bicarbonate. The mixture was extracted with ethyl acetate (2×5 mL), washed with brine then dried over anhydrous MgSO$_4$. The mixture was filtered, the solvent removed under reduced pressure and the product isolated by flash column hromatography on silica gel eluted with 15% EtOAc in hexane to give 280 mg (0.78 mmol) of 3-(BOC)amino-1-diazo-3-(4-biphenyl)propan-2-one (58% yield).

300 MHz $^1$H NMR (CDCl$_3$): δ 1.42 (s, 9H), 5.22 (bs, 1H), 5.29 (s, 1H), 5.9 (br s, 1H), 7.35–7.5 (m, 5H), 7.52–7.62 (m, 4H).

Step F

3(R)-Amino-3-(4-biphenyl)propionic acid, methyl ester

To a 25 mL round bottom flask fitted with a stir bar and septum was added 3-(BOC)amino-1-diazo-3-(4-biphenyl) propan-2-one (280 mg, 0.76 mmol), with 5 mL each of methanol and dioxane. The flask was cooled to 0° C. and 0.15 eq (34 mg, 0.038 mmol) of silver benzoate in 500 μl of triethylamine was added dropwise to the reaction mixture and the mixture allowed to stir at 25° C. for 1 h. The reaction mixture was treated with 10% NH$_4$OH in saturated NH$_4$Cl (10 mL), then extracted with ether (3×10 mL), and the organic layer dried over anahydrous MgSO$_4$. After removal of solvents by evaporation in vacuo, the reside was purified by flash column chromatography on silica gel, eluted with 15% EtOAc in hexane. The 260 mg of product (98% yield) was dissolved in 10 mL of 1 N HCl in ethyl acetate. After stirring for 2 h at room temperature, 180 mg of 3(R)-amino-(4-biphenyl)propionic acid, methyl ester hydrochloride, was obtained by filitration.

300 MHz $^1$H NMR (CD$_3$OD): δ 2.90 (dd, 1H, J=18 Hz, J=6 Hz), 3.02 (dd, 1H, J=18 Hz, J=6 Hz), 3.66 (s, 3H), 5.9 (br s, 1H), 7.33–7.5 (m, 5H), 7.55–7.6 (m, 4H).

The following 3(R)-amino-propionic acid derivatives were prepared by the procedures described in Refemece Example 5 substituting the appropriate arylboronic acid analog for benzeneboronic acid:

REFERENCE EXAMPLE 6

3(R)-amino-3-(4-(2'-methoxyphenyl)phenyl) propionic Acid, Methyl Ester

REFERENCE EXAMPLE 7

3(R)-amino-3-(4-(2',6'-dimethoxyphenyl)phenyl) propionic Acid, Methyl Ester

REFERENCE EXAMPLE 8

(L)-4-(2'-Methoxy-6'-cyano-phenyl)phenylalanine, Tert-butyl Ester

Step A

N-(CBZ)-4-(trifluoromethylsulfonyloxy)-(L)-phenylalanine, tert-butyl ester.

To a solution of 15.15 g (4.1 mmol) N-(CBZ)-(L)-tyrosine, tert-butyl ester in 150 mL of dry methylene chloride at 0° C. was added 12.9 g (164 mmol) of pyridine followed by the dropwise addition of 12.68 g (4.5 mmol) of trifluoromethylsulfonyl chloride. The reaction mixture was stirred at room temperature for 4 hours at which time TLC (25% EtOAc in hexanes) indicated complete consumption of starting material. The reaction mixture was shaken with 1N HCl (3×100 mL), saturated NaHCO$_3$ solution (2×50 mL), and brine (1×50 mL). The organic phase was dried over anhydrous MgSO$_4$, filtered and concentrated in vacuo to give N-(CBZ)-4-(trifluoromethylsulfonyloxy)-(L)-phenylalanine, tert-butyl ester.

400 MHz $^1$H NMR (CDCl$_3$): δ 1.39 (s, 9H); 3.10 (d, 2H); 4.52 (m, 1H); 5.10 (dd, 2H); 7.18 and 7.25 (dd, 2H); 7.30 (m, 5H).

Step B

2-Methoxy-6-(methoxymethyloxy)-phenylboronic acid.

To a solution of 12.0 g (100 mmol) of 3-methoxyphenol in 100 mL of methylene chloride at 0° C. was added 29.5 g (229 mmol) of diisopropylethylamine followed by dropwise addition of 10 g of chloromethyl methyl ether. The reaction mixture was stirred at room temperature overnight, washed with 1N HCl (3×75 mL), 1N NaOH (3×75 mL) and brine and was dried over anhydrous MgSO4. The mixture was filtered and concentrated in vacuo to give 3-methoxymethyloxy-anisole. 6.0 g (36 mmol) of 3-methoxymethyloxy-anisole was dissolved in 100 mL dry THF and was cooled to −78° C. To the solution was added dropwise 20 mL (50 mmol) of 2.5M n-butyl lithium in hexanes. The solution was stirred at −78° C. for 1 hour, the ice bath was removed and the solution stirred at room temperature for a further 1 hour. The reaction mixture was cooled to −78° C. and treated with 5.56 g (54 mmol) of trimethyl orthoborate. The solution was stirred for 1 hour and then allowed to warm to room temperature over 1 hour. The solution was treated with 30 mL of saturated NH$_4$Cl solution and 100 mL of ethyl acetate with stirring. The pH was immediately adjusted to 5.0 by addition of aliquots of 5% citric acid solution. The aqueous phase was promptly extracted with ethyl acetate (3×50 mL). The combined ethyl acetate phases were extracted with 1N NaOH solution (3×50 mL). The combined basic extracts were acidified with rapid stirring by dropwise addition of concentrated hydrochloric acid to pH 5.0. The mixture was extracted by ethyl acetate (3×75 mL). The combined EtOAc phases were dried over anhydrous MgSO$_4$, filtered and concentrated in vacuo to give 2-methoxy-6-(methoxymethyloxy)phenylboronic acid.

Step

C N-(CBZ)-(L)-4-(2'-Methoxy-6'-methoxymethyloxy-phenyl)-phenylalanine, tert-butyl ester.

To a solution of 7.5 g (15 mmol) of N-(CBZ)-4-(trifluoromethylsulfonyloxy)-(L)-phenylalanine, tert-butyl ester in 75 mL of toluene was added 6.35 g (29 mmol) of 2-methoxy-6-(methoxymethyloxy)-phenylboronic acid followed by 25 mL of ethanol, 25 mL of water, 12 g (87 mmol) of potassium carbonate and 1 g of tetrakistriphenylphosphine palladium (0). The reaction mixture was degassed and then heated at 90° C. for 8 hours. The mixture was cooled to room temperature and was diluted with 150 mL of ethyl acetate and was washed with water (3×75 mL). The organic phase was dried over anhdyrous MgSO$_4$, filtered and concentrated in vacuo. The residue was purified by flash column chromatography on silica gel eluted with a gradient of 25–35% EtOAc in hexanes to give N-(CBZ)-(L)-4-[(2'-methoxy-6'-methoxymethyloxy)phenyl]phenylalanine, tert-butyl ester.

$^1$H-NMR (400 MHz, CDCl$_3$): 1.41 (s, 9H); 3.1 and 3.2 (AB ddd, 2h); 3.31 (s, 3H); 3.72 (s, 3H); 4.60 (m, 1H); 5.03 (s, 2H); 5.15 9s, 2H); 5.40 (bd, 1H); 6.70 (d, 1H); 6.89 (d, 1H); 7.20–7.40 (m, 10H).

Step D

N-(CBZ)-(L)-4-[(2'-Methoxy-6'-hydroxy)phenyl]phenylalanine, tert-butyl ester.

N-(CBZ)-(L)-4-[(2'-methoxy-6'-methoxymethyloxy)phenyl]phenylalanine, tert-butyl ester (3.30 g, 6.4 mmol) was dissolved in 25 mL of tert-butyl alcohol. Pyridinium tosylate (320 mg, 1.3 mmol) was added and the mixture was heated at 85° C. for 12 hours. The reaction mixture was heated for 12 hours, then concentrated in vacuo. The residue was dissolved in 100 mL of ethyl acetate and washed with 1N HCl (3×20 mL), saturated sodium bicarbonate (3×20 mL) and brine (1×20 mL). The solution was dried over anhydrous MgSO$_4$, filtered and concentrated in vacuo. The residue was purified by flash column chromatography on silica gel eluted with 25% EtOAc in hexanes to give N-(CBZ)-(L)-4-[(2'-methoxy-6'-hydroxy-phenyl]phenylalanine, tert-butyl ester.

$^1$H-NMR (400 MHz, CDCl$_3$) δ 1.42 (s, 9H); 3.15 (d, 2H); 3.72 (s, 3H); 4.58 (m, 1h); 5.13 (s, 2H); 5.35 (d, 1H); 6.55 (d, 1H); 6.68 (d, 1H); 7.21 (t, 1H); 7.25–7.40 (9H).

Step E

N-(CBZ)-(L)-4-(2'-methoxy-6'-trifluoromethylsulfonyloxy-phenyl)-phenylalanine, tert-butyl ester.

N-(CBZ)- (L)-4-[(2'-methoxy)-6'-hydroxy)phenyl] phenylalanine, tert-butyl ester (1.51 g, 3.2 mmol) was dissolved in 20 mL of methylene chloride and treated with 0.75 g (9.6 mmol) of pyridine. The solution was cooled to 0° C. and treated with 1.01 g (3.6 mmol) trifluoromethylsulfonic acid anhydride. The reaction mixture was stirred at 0° C. over three days. The solution was diluted with methylene chloride, washed with 1N HCl (3×15 mL), sodium bicarbonate solution (2×15mL) and dried over anhydrous MgSO$_4$, filtered and concentrated in vacuo. The residue was purified by flash column chromatography on silica gel eluted with 20% EtOAc in hexanes to provide N-(CBZ)-(L)-4-[(2'-methoxy-6'-trifluoromethylsulfonyloxy)phenyl] phenylalanine, tert-butyl ester.

-$^1$H-NMR (400 MHz, CDCl$_3$): 1.45 (s, 9H); 3.16 (d, 2H); 3.78 (s, 3H); 4.60 (m, 1H); 5.13 (s, 2H); 5.27 (d, 1H); 6.99 (d, 1H); 7.02 (d, 1H); 7.25 (m, 4H); 7.31–7.40 (m, 6H).

Step F

N-(CBZ)-(L)-4-[(2'-methoxy-6'-cyano)phenyl]phenylalanine, tert-butyl ester.

To a solution of 0.96 g (1.6 mmol) of N-(CBZ)-(L)-4-[(2'-methoxy-6'-trifluomethylsulfonyloxy)phenyl] phenylalanine, tert-butyl ester in 10 mL of DMF was added 0.37 g (3.1 mmol) of zinc cyanide and 92 mg (0.08 mmol) tetrakistriphenyl-phosphine palladium (0). The reaction mixture was degassed and heated at 90° C. for 2 hours. The mixture was diluted with 100 mL of ethyl acetate and was washed with 1N HCl (3×20 mL), saturated sodium bicarbonate solution (2×25 mL) and was dried over anhydrous MgSO$_4$, filtered and concentrated in vacuo. The residue was purified by flash column chromatography on silica gel eluted with a gradient of 15–30% EtOAc in hexanes to give N-(CBZ)-(L)-4-[(2'-methoxy-6'-cyano)phenyl] phenylalanine, tert-butyl ester as an oil. NMR (400 MHz, CDCl$_3$): 1.40 (s, 9H); 3.25 (m, 2H); 3.79 (s, 3H); 4.60 (m, 1H); 5.15 (s, 2H); 5.38 (d, 1H); 7.19 (d, 1H); 7.28–7.40 (m, 11H).

Step G (L)-4-[(2'-methoxy-6'-cyano)phenyl]phenylalanine, tert-butyl ester.

A solution of 0.34 g (0.73 mmol) of N-(CBZ)-(L)-4-[(2'-methoxy-6'-cyano)phenyl]phenylalanine, tert-butyl ester in 5 mL of ethanol was treated with 0.043 g (0.7 mmol) of acetic acid and 25 mg of palladium hydroxide. The mixture was stirred under an atmosphere of hydrogen gas and carefully monitored by TLC for consumption of starting material at which time (2 hours) the mixture was filtered through celite and concentrated in vacuo. The residue was dissolved in 20 mL of ethyl acetate and was washed with 1N NaOH solution (3×5 mL) and was dried over anhydrous MgSO$_4$, filtered and concentrated in vacuo to provide (L)-4-[(2'-methoxy-6'-cyano)phenyl]phenylalanine, tert-butyl ester.

$^1$H-NMR (400 MHz, CDCl$_3$): 1.43 (s, 9H); 1.70 (bs, 2H); 2.93 (dd, 1H); 3.09 (dd, 1H); 3.68 (t, 1H); 3.79 (s, 3H); 7.19 (d, 1H); 7.30–7.40 (m, 6H).

REFERENCE EXAMPLE 9

(L)-4-[(2'-methoxy-6'-ethyl)phenyl]phenylalanine, tert-butyl ester

Step A

N-(CBZ)-(L)-4-[(2'-methoxy-6'-ethenyl)phenyl] phenylalanine, tert-butyl ester.

To a solution of 0.32 g (0.52 mmol) of N-(CBZ)-(L)-4-[(2'-methoxy-6'-trifluomethylsulfonyloxy)phenyl] phenylalanine, tert-butyl ester (Reference Example 8, Step E) in 5 mL of dry DMF was added 0.33 g (1.05 mmol) vinyl tributyltin, 36 mg (0.05 mmol) bis-triphenylphosphine palladium dichloride, 0.22 g (5.2 mmol) lithium chloride and 0.082 g (0.3 mmol) of triphenyl phosphine. The mixture was degassed and heated at 90° C. After 2 hours 330 mg of vinyltributyl tin was added and the solution was heated overnight. The reaction mixture was cooled and then diluted with ethyl acetate (50 mL) and was washed with saturated KF solution (2×10 mL), water (2×20 mL) and brine (1×10 mL) and was dried over anhydrous MgSO4. The mixture was filtered and concentrated in vacuo. The residue was purified by flash column chromatography on silica gel eluted with 15% EtOAc in hexanes to give N-(CBZ)-(L)-4-[(2'-methoxy-6'-ethenyl)phenyl]phenylalanine, tert-butyl ester.

$^1$H-NMR (400 MHz, CDCl$_3$):1.43 (s, 9H); 3.15 (m, 2H); 3.72 (s, 3H); 4.61 (m, 1H); 5.12 (d, 1H); 5.15 (s, 2H); 5.42 (d, 1H); 5.65 (d, 1H); 6.42 (dd, 1H); 6.92 (dd, 1H); 7.18–7.41 (m, 11H).

Step B (L)-4-[(2'-methoxy-6'-ethyl)phenyl]phenylalanine, tert-butyl ester.

A solution of 71 mg of N-(CBZ)-(L)-4-[(2'-methoxy-6'-ethenyl)-phenyl]phenylalanine, tert-butyl ester in 5 mL of ethanol and several drops of acetic acid was hydrogenolyzed under atmospheric pressure in the presence of 20% Pd(OH)$_2$ overnight. The reaction mixture was filtered through celite and was concentrated in vacuo. The residue was dissolved in EtOAc and was washed with saturated NaHCO$_3$ and dried over anhydrous MgSO4, filtered and concentrated in vacuo to give (L)-4-[(2'-methoxy-6'-ethyl)phenyl]phenylalanine, tert-butyl ester.

$^1$H-NMR (400 MHz, CDCl$_3$): 1.03 (t, 3H); 1.42 (s, 9H); 1.70 (bs, 2H); 2.40 (q, 2H); 2.95 and 3.07 (dAB, 2H); 3.70 (s, 3H); 6.81 (d, 1H); 6.95 (d,1H); 7.18 (d, 1H); 7.28 (d, 4H).

REFERENCE EXAMPLE 10

(L)-4-[(2'-methoxy-6'-dimethylamino)phenyl] phenylalanine, Tert-butyl Ester

Step A 2-methoxy-6-dimethylamino-phenylboronic acid.

To a solution of 5.3 g (35 mmol) of 3-dimethylamino-anisole in 25 mL of dry THF at −78° C. was added 19 mL (47 mmol) of a 2.5M solution of n-butyl lithium in hexanes. The reaction mixture was stirred for 1 hour before removing the ice bath and warming to room temperature for 90 minutes. The solution was cooled to −78° C., treated with 8.75 g (84 mmol) of trimethyl orthoborate, and then stirred for one hour before warming to room temperature for one hour. The reaction was quenched by the addition of 20 mL of water and sufficient acetic acid to neutralize the mixture. The reaction mixture was extracted with ethyl acetate (3×30 mL), and the combined organic extracts were extracted with 1N NaOH solution (4×15 mL). The combined aqueous extracts were acidified with acetic acid and extracted with EtOAc (3×20 mL). The organic phase was washed with brine, dried over anhydrous MgSO4, filtered and concentrated in vacuo to give 2-methoxy-6-dimethylamino-phenylboronic acid.

Step B

N-(CBZ)-(L)-4-(2'-methoxy-6'-dimethylamino-phenyl)-phenylalanine, tert-butyl ester.

2-Methoxy-6-dimethylamino-phenylboronic acid (0.18 g, 0.9 mmol), N-(CBZ)-(L)-4-(trifluomethylsulfonyloxy)-phenylalanine tert-butyl ester (0.36 g, 0.73 mmol), potassium carbonate (0.37 g, 2.7 mmol) and 15 mg of tetrakistriphenylphospine palladium(0) were suspended in 2 mL of toluene and 1 mL of ethanol. The mixture was heated at 90° C. for 3 hours, diluted with ethyl acetate, washed with water, dried over anhydrous MgSO4, filtered and concentrated in vacuo. The residue was purified by MPLC on silica gel eluted with a gradient of 10–90% EtOAc in hexanes to provide N-(CBZ)-(L)-4-[(2'-methoxy-6'-dimethylamino)phenyl]phenylalanine, tert-butyl ester as a colorless oil.

NMR (400 MHz, CDCl$_3$): 1.41 (d, 9H); 2.45 (s, 6H); 2.45 (s, 6H); 3.15 (d, 2H); 3.70 (s, 3H); 4.60 (m, 1h); 5.15 (m, 2H); 5.40 (bd, 1H); 5.65 (d, 1H); 5.72 (d, 1H); 7.18–7.40 (m, 10H).

Step C (L) 4-[(2'-methoxy-6'-dimethylamino)phenyl]phenylalanine, tert-butyl ester.

N-(CBZ)-(L)-4-[(2'-methoxy-6'-dimethylamino)phenyl]phenylalanine, tert-butyl ester was hydrogenolyzed as described in Reference Example 9 Step B to give the title compound. NMR (400 MHz, CDCl$_3$): 1.42 (s, 9H); 2.45 (s, 6H); 2.87 (m, 1H); 3.06 (m, 1H); 3.65 (m, 1H); 3.70 (s, 3H); 6.65 (d, 1H); 6.72 (d, 1H); 7.20–7.38 (m, 6H).

REFERENCE EXAMPLE 11

(L)-4-[(2'-Methoxy-6'-hydroxy)phenyl] phenylalanine, Tert-butyl Ester

The product of Reference Example 8, Step D, N-(CBZ)-(L)-4-[(2'-methoxy-6'-hydroxy)phenyl]phenylalanine, tert-butyl ester was hydrogenolyzed as described in Reference Example 9, Step B to give (L)-4-[(2'-methoxy-6'-hydroxy)-phenyl]phenylalanine, tert-butyl ester.

$^1$H-NMR (400 MHz, CDCl$_3$):1.44 (s, 9H); 2.88 and 3.05 (dAB, 2H); 3.62 (m, 1H); 3.72 (s, 3H); 6.55 9d, 1H); 6.65 (d, 1H); 7.20 (t, 1H); 7.32 (m, 4H).

REFERENCE EXAMPLE 12

(L)-4-(2',6'-dichlorobenzamido)phenylalanine, Methyl Ester Hydrochloride

Step A

N-(BOC)-(L)-4-(2',6'-dichlorobenzamido)phenylalanine, methyl ester.

N$_{(a)}$-(BOC)-(L)-4-(FMOC-amino)-phenylalanine, methyl ester (9.62 g, 18.6 mmol) was dissolved in 15 mL of DMF and treated with diethylamine(11.6 mL, 112 mmol). The reaction mixture was stirred at room temperature for two hours, then concentrated in vacuo to give an viscous oil. This residue was dissolved in CH$_2$Cl$_2$ (50 mL) then treated with diisopropylethylamine (5.16 mL, 27.9 mmol) and 2,6-dichlorobenzoyl chloride (2.93 mL, 20.4 mmol). The reaction mixture was stirred overnight at room temperature and then quenched with H$_2$O (40 mL). The layers were separated and the aqueous layer was extracted with CH$_2$Cl$_2$ (2×40 mL). The organic layers were combined and washed with brine (1×200 mL) then dried over anhydrous MgSO4. The mixture was filtered and concentrated in vacuo, then the residue was purified by flash column chromatography eluted with 50% EtOAc in hexane to give N-(BOC)-(L)-4-(2',6'-dichlorobenzamido)phenylalanine, methyl ester (7.3 g).

500 MHz $^1$H NMR (CDCl$_3$): 1.44 (s, 9H); 3.12 (m, 2H); 3.75 (s, 3H); 4.61 (m, 1H); 5.00 (d, 1H); 7.15 (d, 2H); 7.32 (m, 3H); 7.59 (d, 2H).

Step B (L)-4-(2',6'-dichlorobenzamido)phenylalanine, methyl ester hydrochloride.

N-(BOC)- (L)-4-(2',6'-dichlorobenzamido)phenylalanine, methyl ester (2.50 g, 5.35 mmol) was dissolved in dioxane (5 mL) and treated with HCl in EtOAc (18.4 mL of 2.9 N). The mixture was stirred overnight at room temperature, then concentrated in vacuo to give a quantitative yield of (L)-4-(2',6'-dichlorobenzamido)-phenylalanine, methyl ester hydrochloride.

500 MHz $^1$H NMR (CD$_3$OD): 3.17 (m, 1H); 3.28 (m, 1H); 3.84 (s, 3H); 4.33 (m, 1H); 7.28 (d, 2H); 7.46 (m, 3H); 7.68 (d, 2H).

REFERENCE EXAMPLE 13

N-(BOC)-(D,L)-3-Phenylsulfonyl-nipecotic Acid

Step A

N-(BOC)-(D,L)-Nipecotic acid, ethyl ester

To a solution of (D,L)-nipecotic acid, ethyl ester (Aldrich Chemical, 10 g, 63.6 mmol) in methylene chloride (50 mL) was added portionwise di-tert-butyl dicarbonate (13.9 g, 63.7 mmol). After stirring at room temperature for two hours, the solvent was removed under reduced pressure, and the residue was used directly in the subsequent step.

Step B

N-(BOC)-(D,L)-3-Phenylthio-nipecotic acid, ethyl ester

To a solution of potassium hexamethyldisilazide (46 mL, 0.5M in THF, 23 mmol) in THF (120 mL) at −78° C., was added a solution of N-(BOC)-(D,L)-nipecotic acid, ethyl ester (6 g, 23 mmol) in 30 mL of THF. After stirring at this temperature for 35 min, diphenyl disulfide (5.5 g, in 10 mL THF) was added dropwise. After 5 min, the mixture was allowed to warm to ambient temperature. The mixture was poured into saturated ammonium chloride solution (200 mL) and extracted with ethyl acetate (300 mL). After drying the organics over anhydrous magnesium sulfate and filtration, the solvent was removed under reduced pressure. The resulting residue was purified by flash column chromatography on silica gel eluted with 8% EtOAc in hexanes giving N-(BOC)-(D,L)-3-phenylthio-nipecotic acid, ethyl ester (9.7 g).

Step C

N-(BOC)-(D,L)-3-Phenylthio-nipecotic acid.

To a solution of 8.8 g (22 mmol) of N-(BOC)-(D,L)-3-phenylthio-nipecotic acid, ethyl ester in 75 mL of ethanol and 50 mL of water was added 2.2 g (55 mmol) of NaOH. The solution was heated at 80° C. for 3 hours and then at 50° C. overnight. The solution was diluted with 100 mL of water and extracted with ethyl acetate (3×50 mL). The aqueous phase was acidified with HCl and extracted with ethyl acetate (3×75 mL). The combined organic phases were washed with brine and dried over anhydrous MgSO4, filtered and concentrated in vacuo to give N-(BOC)-(D,L)-3-phenylthio-nipecotic acid.

Step D

N-(BOC)-(D,L)-3-Phenylsulfonyl-nipecotic acid.

To a solution of 6.9 g of N-(BOC)-(D,L)-3-phenylthio-nipecotic acid in 100 mL of acetic acid was added at 0° C. 32 mL of 30% hydrogen peroxide solution. The reaction mixture was allowed to gradually warm to room temperature. The progress of the reaction was monitored by HPLC. After stirring overnight, the reaction mixture was cooled in an ice bath and was treated with a saturated solution of $Na_2SO_3$ until KI/starch paper indicated that the hydrogen peroxide had been consumed. The pH was confirmed as 5.0 and the solution was extracted with ethyl acetate (4×75 mL). The combined organic phases were washed with brine and dried over anhydrous MgSO4, filtered and concentrated in vacuo to give N-(BOC)-(D,L)-3-phenylsulfonyl-nipecotic acid, which crystallized upon standing.

400 MHz $^1$H NMR (CD$_3$OD); δ 1.59 (s, 9H); 1.65–1.75 (m, 2H); 1.79 (m, 1H); 2.06 (dt, 1H); 2.40 (bd, 1H); 2.75 (bs, 1H); 3.85 (bd, 1H); 4.65 (d, 1H); 7.62 (t, 1H); 7.75 (t, 1H); 7.86 (d, 1H).

General Method 1: Amino acid coupling conditions.

In general, 1.0 eq of amino acid ester was coupled to 1.5 eq of (3-sulfonyl or sulfenyl)-N-(BOC)-cyclic amino acid by reaction in DMF with 1.5 eq HOBt or HOAt, 1.5 eq of HBTU or HATU followed by 4.5 eq of diisopropylethylamine. After stirring overnight, under nitrogen, the reaction mixture was diluted with ether or ethyl acetate and was washed with 1N HCl (2x), saturated NaHCO$_3$ (2x), and brine (1x) and was dried over anhydrous MgSO4. The reaction mixture was filtered and concentrated in vacuo and the residue was purified on silica gel eluted with ether/hexanes or ethyl acetate/hexanes mixtures to recover the desired product.

The following examples are provided to more fully illustrate the invention and are not to be construed as limiting the invention in any manner.

EXAMPLE 1

N-(3-Phenylthio-nipecotyl)-(L)-4-(2'-methoxyphenyl)phenylalanine (Isomer A)

Step A

N-(BOC)-3-(D,L)-phenylsulfonyl nipecotic acid, sodium salt

To a solution of N-(BOC)-(D,L)-3-phenylthio-nipecotic acid, ethyl ester (Reference Example 13, 3.2 g) in ethanol (15 mL) was added 5N sodium hydroxide solution (2.64 ml, 13.2 mmol). After stirring at 55° C. for 12 hours, the solvent removed under reduced pressure. The resulting residue was azeotroped three times with toluene to yield N-(BOC)-(D,L)-3-phenylthio-nipecotic acid, sodium salt (2.5 g) which was used directly in the subsequent step.

Step B

N-(BOC)-(3-Phenylthio-nipecotyl)-(L)-4-(2'-methoxyphenyl)-phenylalanine, tert-butyl ester To a solution of N-(BOC)-(D,L)-3-phenylthio-nipecotic acid, sodium salt (308 mg, 0.89 mmol) and (L)-4-2'-methoxyphenyl)-phenylalanine, tert-butyl ester (Reference Example 3, 332 mg, 0.91 mmol) in DMF (5 mL), was added sequentially diisopropylethylamine (400 μl, 2.3 mmol), HOAt (249 mg, 1.83 mmol) and HATU (416 mg, 1.09 mmol). After stirring at room temperature for 16 hours, the solvent was removed under reduced pressure. The resulting residue was purified by flash column chromatography on silica gel eluted with 15% EtOAc in hexanes to yield two diastereomers of product, a less polar compound, Isomer A and a more polar compound, Isomer B.

Step C

N-(3-Phenylthio-nipecotyl)-(L)-4-(2'-methoxyphenyl)phenylalanine (Isomer A)

To a solution of Isomer A from Step B (11.4 mg) in methylene chloride (500 μl) was added TFA (500 μl). After stirring for 3 hours at room temperature, the mixture was concentrated in vacuo. The residue was dissolved in approximately 3 mL of 30% CH$_3$CN/H$_2$O then lyophilized to provide N-(3-phenylthio-nipecotyl)-(L)4-(2'-methoxyphenyl)phenylalanine (Isomer A) (8.9 mg).

HPLC MS: 491 (M+H$^+$)

EXAMPLE 2

N-(3-Phenylthio-nipecotyl)-(L)-4-(2'-methoxyphenyl)phenylalanine (Isomer B)

Isomer B from Example 1, Step B (11.2 mg) was treated according to the method described in Example 1, Step C with TFA, to yield N-(3-phenylthio-nipecotyl)-(L)-4-(2'-methoxyphenyl)phenylalanine (Isomer B) (7.9 mg).

HPLC MS: 491 (M+H$^+$).

EXAMPLE 3

N-(3-Phenylthio-nipecotyl)-(L)-4-(2',6'-dimethoxyphenyl)phenylalanine (Isomer A)

Step A

N-(BOC)-(3-Phenylthio-nipecotyl)-(L)-4-(2',6'-dimethoxyphenyl)-phenylalanine, tert-butyl ester The procedure described in Example 1, Step B was performed with (L)-4-(2',6'-dimethoxyphenyl) phenylalanine, tert-butyl ester (Reference Example 4, 359 mg) in place of (L)-4-(2'-methoxyphenyl)phenylalanine, tert-butyl ester to give, after flash column chromatography on silica gel eluted with 20% EtOAc in hexanes, two diastereomers of product, the less polar Isomer A (220 mg) and the more polar compound, Isomer B (200 mg).

Step B

N-(3-Phenylthio-nipecotyl)-(L)-4-(2',6'-dimethoxyphenyl)phenylalanine (Isomer A)

Isomer A from Step A (10 mg) was treated according to the procedure described in Example 1, Step C with TFA, to yield N-(3-phenylthio-nipecotyl)-(L)-4-(2',6'-dimethoxyphenyl)phenylalanine (Isomer A) (8.2 mg).

HPLC MS: 521 (M+H$^+$).

EXAMPLE 4

N-(3-Phenylthio-nipecotyl)-(L)-4-(2',6'-dimethoxyphenyl)phenylalamine (Isomer B)

N-(BOC)-(3-Phenylthio-nipecotyl)-(L)-4-(2',6'-dimethoxyphenyl)-phenylalanine, tert-butyl ester (Isomer B) (Example 3, Step A) (10 mg) was treated according to the procedure described in Example 1, Step C with TFA, to yield N-(3-phenylthio-nipecotyl)-(L)-4-(2',6'-dimethoxyphenyl) phenylalanine (Isomer A) (8.8 mg).

HPLC MS: 521 (M+H$^+$).

EXAMPLE 5

N-(3-Phenylsulfonyl-nipecotyl)-(L)-4-(2'-methoxyphenyl)phenylalanine (Isomer A)

Step A

N-(N-(BOC)-3-Phenylsulfonyl-nipecotyl)-(L)-4-(2'-methoxyphenyl)-phenylalanine, tert-butyl ester (Isomer A)

To a solution of N-(N-(BOC)-3-phenylthio-nipecotyl)-(L)-4-(2'-methoxyphenyl)phenylalanine, tert-butyl ester (Isomer A) (Example 1, Step B) (172 mg, 0.27 mmol) in methylene chloride (3 mL) at 0° C., was added m-chloroperbenzoic acid (111 mg, 0.64 mmol). The cooling bath was removed immediately and the mixture allowed to stir for 15 minutes. It was then applied directly to a silica gel column and eluted with 25% EtOAc in hexanes to yield N-(N-(BOC)-3-phenylsulfonyl-nipecotyl)-(L)-4-(2'-methoxyphenyl)phenylalanine, tert-butyl ester (Isomer A) (167 mg).

Step B

N-(3-Phenylsulfonyl-nipecotyl)-(L)-4-(2'-methoxyphenyl)phenylalanine, tert-butyl ester (Isomer A)

To a solution of N-(N-(BOC)-3-phenylsulfonyl-nipecotyl)-(L)-4-(2'-methoxyphenyl)phenylalanine, tert-butyl ester (167 mg, 0.25 mmol) in tert-butyl acetate (6 mL) was added concentrated sulfuric acid (115 µ). After stirring for 3 hours, the mixture was poured into saturated ammonium chloride solution (25 mL) and extracted with ethyl acetate (100 mL). After drying of the organics over anhydrous magnesium sulfate and filtration, the solvent was removed under reduced pressure. The title compound (135 mg) was obtained and used without further purication.

Step C

N-(3-Phenylsulfonyl-nipecotyl)-(L)-4-(2'-methoxyphenyl)phenylalanine (Isomer A)

N-(3-Phenylsulfonyl-nipecotyl)-(L)-4-(2'-methoxyphenyl)phenylalanine, tert-butyl ester (Isomer A) from Step B (30 mg) was treated according to the method described in Example 1, Step C with TFA, to yield N-(3-phenylsulfonyl-nipecotyl)-(L)-4-(2'-methoxyphenyl) phenylalanine (Isomer A) (25.9 mg).

HPLC MS: 523 (M+H$^+$).

EXAMPLE 6

N-(3-Phenylsulfonyl-nipecotyl)-(L)-4-(2'-methoxyphenyl)phenylalanine (Isomer B)

N-(N-(BOC)-3-Phenylthio-nipecotyl)-(L)-4-(2'-methoxyphenyl)-phenylalanine, tert-butyl ester (Isomer B) (Example 1, Step B) (126 mg) was treated according to the procedure described for Example 5 to yield N-(3-phenylsulfonyl-nipecotyl)-(L)-4-(2'-methoxyphenyl) phenylalanine (Isomer B) (16.3 mg).

HPLC MS: 523 (M+H$^+$).

EXAMPLE 7

N-(1-Methyl-3-phenylsulfonyl-nipecotyl)-(L)-4-(2'-methoxyphenyl)phenylalanine (Isomer A)

Step A

N-(1-Methyl-3-phenylsulfonyl-nipecotyl)-(L)-4-(2'-methoxyphenyl)-phenylalanine, tert-butyl ester (Isomer A)

To a solution of N-(3-phenylsulfonyl-nipecotyl)-(L)-4-(2'-methoxyphenyl)phenylalanine, tert-butyl ester (Isomer A) (Example 5, Step B) (32 mg, 0.06 mmol) in acetonitrile (1 mL) was added aqueous formaldehyde (21 µl, 37%) then 10 minutes later, sodium cyanoborohydride (5.6 mg, 0.09 mmol). After stirring for 3 hours, 3 drops of glacial acetic acid were added, followed by water (3 mL). A solution of 1N sodium hydroxide was added until the mixture was neutral (pH=7), followed by extraction with ethyl acetate (100 mL). After drying of the organics over anhydrous magnesium sulfate and filtration, the solvent was removed under reduced pressure. N-(1-Methyl-3-phenylsulfonyl-nipecotyl)-(L)-4-(2'-methoxyphenyl)phenylalanine, tert-butyl ester (Isomer A) (18.4 mg) was obtained following flash column chromatography on silica gel eluted with 40% EtOAc in hexanes.

Step B

N-(1-Methyl-3-phenylsulfonyl-nipecotyl)-(L)-4-(2'-methoxyphenyl)-phenylalanine (Isomer A)

N-(1-Methyl-3-phenylsulfonyl-nipecotyl)-(L)-4-(2'-methoxyphenyl)-phenylalanine, tert-butyl ester (Isomer A) from Step A (18.4 mg) was treated according to the procedure described in Example 1, Step C with TFA, to yield N-(1-methyl-3-phenylsulfonyl-nipecotyl)-(L)-4-(2'-methoxyphenyl)phenylalanine (Isomer A) (15 mg).

HPLC MS: 537 (M+H$^+$).

EXAMPLE 8

N-(1-Methyl-3-phenylsulfonyl-nipecotyl)-(L)-4-(2'-methoxyphenyl)phenylalanine (Isomer B)

N-(3-Phenylsulfonyl-nipecotyl)-(L)-4-(2'-methoxyphenyl)phenylalanine, tert-butyl ester (Isomer B) (Example 5, Step B,) was treated according to the procedures described in Example 7 to give N-(1-methyl-3-phenylsulfonyl-nipecotyl)-(L)-4-(2'-methoxyphenyl) phenylalanine (Isomer B) (15.8 mg).

HPLC MS: 537 (M+H$^+$).

EXAMPLE 9

N-(3-phenylsulfonyl-nipecotyl)-(L)-4-(2',6'-dimethoxyphenyl)phenylalanine (Isomer A)

Step A.

N-(BOC)-(3-Phenylsulfonyl-nipecotyl)-(L)-4-(2',6'-dimethoxyphenyl)-phenylalanine, tert-butyl ester N-(N-(BOC)-3-Phenylthio-nipecotyl)-(L)-4-(2',6'-dimethoxyphenyl)-phenylalanine, tert-butyl ester (Isomer A) (Example 3, Step A) (200 mg) was treated according to the method described in Example 5, Step A to give N-(BOC)-(3-phenylsulfonyl-nipecotyl)-(L)-4-(2',6'-dimethoxyphenyl)phenylalanine, tert-butyl ester (142 mg).

Step B

N-(3-Phenylsulfonyl-nipecotyl)-(L)-4-(2',6'-dimethoxyphenyl)phenylalanine (Isomer A)

N-(BOC)-(3-Phenylsulfonyl-nipecotyl)-(L)-4-(2',6'-dimethoxyphenyl)-phenylalanine, tert-butyl ester (Isomer A) (53 mg) was treated according to the procedure described in Example 1, Step C with TFA, to yield N-(3- phenylsulfonyl-nipecotyl)-(L)-4-(2',6'-dimethoxyphenyl) phenylalanine (Isomer A) (48 mg).

HPLC MS: 553 (M+H$^+$).

EXAMPLE 10

N-(3-Phenylsulfonyl-nipecotyl)-(L)-4-(2',6'-dimethoxyphenyl)phenylalanine (Isomer B)

N-(N-(BOC)-3-Phenylthio-nipecotyl)-(L)-4-(2',6'-dimethoxyphenyl)-phenylalanine, tert-butyl ester (Isomer B) (Example 3, Step A) (200 mg) was treated according to the procedures described in Example 9 to give N-(3-phenylsulfonyl-nipecotyl)-(L)-4-(2',6'-dimethoxyphenyl)phenylalanine (Isomer B) (46 mg).

HPLC MS: 553 (M+H$^+$).

EXAMPLE 11

N-(N-(BOC)-3-Phenylsulfonyl-nipecotyl)-3(R)-amino-3-(4-(2',6'-dimethoxyphenyl)nhenyl)propionic Acid (Isomer A)

Step A

N-(N-(BOC)-3-Phenylthio-nipecotyl)-3(R)-amino-3-(4-(2',6'-dimethoxyphenyl)phenyl)propionic acid, ethyl ester (Isomer A)

N-(BOC)-(D,L)-3-Phenylthio-nipecotic acid, sodium salt (Example 1, Step A) (60 mg, 0.17 mmol) was reacted according to Example 1, Step B, with 3(R)-amino-3-(4-(2'-methoxyphenyl)phenyl)propionic acid, methyl ester (Reference Example 6 [the material was contaminated with 50% of the corresponding ethyl ester]) (50 mg, 0.14 mmol) to give, after flash column chromatography on silica gel eluted with 20% EtOAc in hexanes, four products. The ethyl ester of the least polar distereomer (Isomer A) and the methyl ester of the more polar distereomer (Isomer B) were separated from this mixture, leaving the other pair of compounds as a mixture.

Step B

N-(N-(BOC)-3-phenylsulfonyl-nipecotyl)-3(R)-amino-3-(4-(2',6'-dimethoxyphenyl)phenyl)propionic acid, ethyl ester (Isomer A)

N-(1- tert-butyloxycarbonyl-3-phenylthio-nipecotyl)-3 (R)-amino-3-(4-(2',6'-dimethoxyphenyl)phenyl)propionic acid, ethyl ester (Isomer A) (4.8 mg) was reacted according to the procedure described in Example 5, Step A to yield N-(N-(BOC)-3-phenylsulfonyl-nipecotyl)-3(R)-amino-3-(4-(2',6'-dimethoxyphenyl)phenyl)propionic acid, ethyl ester (Isomer A (2.8 mg).

Step C

N-(N-(BOC)-3-phenylsulfonyl-nipecotyl)-3(R)-amino-3-(4-(2',6'-dimethoxyphenyl)phenyl)propionic acid (Isomer A)

N-(N-(BOC)-3-phenylsulfonyl-nipecotyl)-3(R)-amino-3-(4-(2',6'-dimethoxyphenyl)phenyl)propionic acid, ethyl ester (2.8 mg) was dissolved in methanol (200 μl) and sodium hydroxide solution (10 μl, 1N) was added. After stirring for 3 hours, the mixture was poured into saturated ammonium chloride solution (10 mL) and extracted into ethyl acetate (30 mL). After drying of the organics over anhydrous magnesium sulfate and filtration, the solvent was removed under reduced pressure. The title compound was isolated by lyophilization (1.3 mg).

HPLC MS:675 (M+Na$^+$).

EXAMPLE 12

N-(N-(BOC)-3-Phenylsulfonyl-nipecotyl)-3(R)-amino-3-(4-(2',6'-dimethoxyphenyl)phenyl)propionic Acid (Isomer B)

N-(N-(BOC)-3-phenylthio-nipecotyl)-3(R)-amino-3-(4-(2',6'-dimethoxyphenyl)phenyl)propionic acid, methyl ester (Isomer B) (Example 11, Step A) was treated according to the procedures described in Steps B and C of Example 11 to yield N-(N-(BOC)-3-phenylsulfonyl-nipecotyl)-3(R)-amino-3-(4-(2',6'-dimethoxyphenyl)phenyl)propionic acid (Isomer B) (3.8 mg).

HPLC MS:675 (M+Na$^+$).

EXAMPLE 13

N-(3-Phenylsulfonyl-nipecotyl)-3(R)-amino-3-(4-(2',6'-dimethoxyphenyl)phenyl)propionic Acid N-(N-(BOC)-3-phenylsulfonyl-nipecotyl)-3(R)-amino-3-(4-(2',6'-dimethoxyphenyl)phenyl)propionic acid (Isomer A) (Example 11) was treated according to the procedure described in Example 1, Step C with TFA, to yield N-(3-phenylsulfonyl-nipecotyl)-3(R)-amino-3-(4-(2',6'-dimethoxyphenyl)phenyl)propionic acid (2.0 mg).

HPLC MS:553 (M+H$^+$).

EXAMPLE 14

N-(3-Phenylthio-nipecotyl)-(L)-phenylalanine (Isomer A)

Step A

N-(N-(BOC)-3-Phenylthio-nipecotyl)-(L)-phenylalanine, ethyl ester

The procedure described in Example 1, Step B was performed using (L)-phenylalanine, ethyl ester in place of (L)-4-(2'-methoxyphenyl)phenylalanine, tert-butyl ester to yield, after flash column chromatography on silica gel eluted with a gradient of 30–50% EtOAc in hexanes, two diastereomers of N-(N-(BOC)-3-phenylthio-nipecotyl)-(L)-phenylalanine, ethyl ester: a less polar Isomer A (61.3 mg) and a more polar compound, Isomer B (54.2 mg).

Step B

N-(N-(BOC)-3-Phenylthio-nipecotyl)-(L)-phenylalanine (Isomer A)

N-(N-(BOC)-3-phenylthio-nipecotyl)-(L)-phenylalanine, ethyl ester (Isomer A) from Step A was treated according to the procedure described in Example 11, Step C to yield N-(N-(BOC)-3-phenylthio-nipecotyl)-(L)-phenylalanine (Isomer A).

HPLC MS: 507 (M+Na$^+$).

Step C

N-(3-Phenylthio-nipecotyl)-(L)-phenylalanine (Isomer A)

N-(N-(BOC)-3-phenylthio-nipecotyl)-(L)-phenylalanine (Isomer A) from Step B was treated according to the procedure described in Example 1, Step C to yield N-(3-phenylthio-nipecotyl)-(L)-phenylalanine (Isomer A) (8.2 mg).

HPLC MS: 385 (M+H$^+$).

EXAMPLE 15

N-(3-Phenylthio-nipecotyl)-(L)-phenylalanine (Isomer B)

N-(N-(BOC)-3-Phenylthio-nipecotyl)-(L)-phenylalanine, ethyl ester (Isomer B) from Example 14, Step A was treated according to the procedures in Steps B and C of Example 14 to give N-(3-phenylthio-nipecotyl)-(L)-phenylalanine (Isomer B) (7.8 mg).

HPLC MS: 385 (M+H$^+$).

EXAMPLE 16

N-(3-Phenylthio-nipecotyl)-(L)-tyrosine (Isomer A)

Step A

N-(N-(BOC)-3-Phenylthio-nipecotyl)-(L)-tyrosine, tert-butyl ester (Isomer A)

The procedure described in Example 14, Step A was performed using (L)-tyrosine, tert-butyl ester in place of (L)-4-2'-methoxyphenyl)phenylalanine, tert-butyl ester to give, after flash column chromatography eluting with a gradient of 30–50% EtOAc in hexanes, two diastereomers of N-(N-(BOC)-3-phenylthio-nipecotyl)-(L)-tyrosine, tert-butyl ester: the less polar Isomer A (112 mg) and the more polar compound, Isomer B (95 mg).

Step B

N-(3-Phenylthio-nipecotyl)-(L)-tyrosine (Isomer A)

N-(N-(BOC)-3-phenylthio-nipecotyl)-(L)-tyrosine, tert-butyl ester (Isomer A) from Step A was treated according to the procedure described in Example 11, Step C to yield N-(3-phenylthio-nipecotyl)-(L)-tyrosine (Isomer A).

HPLC MS: 401 (M+H$^+$).

EXAMPLE 17

N-(3-Phenylthio-nipecotyl)-(L)-tyrosine (Isomer B)

N-(N-(BOC)-3-Phenylthio-nipecotyl)-(L)-tyrosine, tert-butyl ester (Isomer B) from Example 16, Step A was treated according to the procedure described in Example 1, Step C to yield N-(3-phenylthio-nipecotyl)-(L)-tyrosine (Isomer B).

HPLC MS: 401 (M+H$^+$).

EXAMPLE 18

N-(3-Phenylsulfonyl-nipecotyl)-(L)-tyrosine (Isomer A)

Step A

N-(N-(BOC)-3-Phenylsulfonyl-nipecotyl)-(L)-tyrosine, tert-butyl ester (Isomer A)

N-(N-(BOC)-3-phenylthio-nipecotyl)-(L)-tyrosine, tert-butyl ester (Isomer A) from Example 16, Step A was treated according to the procedure described in Example 5, Step A to yield N-(N-(BOC)-phenylsulfonyl-nipecotyl)-(L)-tyrosine, tert-butyl ester (Isomer A).

Step B

N-(N-(BOC)-3-Phenylsulfonyl-nipecotyl)-(L)-tyrosine (Isomer A)

N-(N-(BOC)-Phenylsulfonyl-nipecotyl)-(L)-tyrosine, tert-butyl ester (Isomer A) from Step A was treated according to the procedures described in Example 1, Step C to give N-(N-(BOC)-3-phenylsulfonyl-nipecotyl)-(L)-tyrosine (Isomer A).

HPLC MS: 433 (M+H$^+$).

EXAMPLE 19

N-(3-Phenylsulfonyl-nipecotyl)-(L)-tyrosine (Isomer B)

Step A

N-(N-(BOC)-3-Phenylsulfonyl-nipecotyl)-(L)-tyrosine, tert-butyl ester (Isomer B)

N-(N-(BOC)-3-phenylthio-nipecotyl)-(L)-tyrosine, tert-butyl ester (Isomer B) from Example 16, Step A was treated according to the procedure described in Example 5, Step A to yield N-(N-(BOC)-phenylsulfonyl-nipecotyl)-(L)-tyrosine, tert-butyl ester (Isomer B).

Step B

N-(N-(BOC)-3-Phenylsulfonyl-nipecotyl)-(L)-tyrosine (Isomer B)

N-(N-(BOC)-Phenylsulfonyl-nipecotyl)-(L)-tyrosine, tert-butyl ester (Isomer B) from Step A was treated according to the procedures described in Example 1, Step C to give N-(N-(BOC)-3-phenylsulfonyl-nipecotyl)-(L)-tyrosine (Isomer B).

HPLC MS: 433 (M+H$^+$).

EXAMPLE 20

N-(3-(4'-Bromophenylsulfonyl)-nipecotyl)-(L)-4-(2', 6'-dimethoxyphenyl)-phenylalanine (Isomer A)

Step A

4-Bromophenylsulfonyl fluoride.

To a solution of 4-bromophenylsulfonyl chloride (2 g, 7.83 mmol) in acetonitrile (10 mL), was added fluoride on Amberlyst A-26 (Aldrich Chemical Company, 7.5 g, 21.6 mmol F$^-$). After agitation for 5 hours at room temperature, the mixture was filtered. The solvent was removed under reduced pressure to give 4-bromophenylsulfonyl fluoride (1.5 g) (confirmed by IR spectroscopy).

Step B

N-(BOC)-(D,L)-3-(4'-Bromophenyl)sulfonyl-nipecotic acid, ethyl ester

To a solution of potassium hexamethyldisilazide (3.6 mL, 0.5 M in toluene, 1.8 mmol) in THF (5 mL) at −78° C., was added a solution of N-(BOC)-(D,L)-nipecotic acid, ethyl ester (308 mg, 1.2 mmol), dissolved in 2 mL of THF. After stirring at this temperature for 45 min, 4-bromophenylsulfonyl fluoride (516 mg, 2.2 mmol, in 2 mL THF) was added dropwise. After 5 min, the mixture was allowed to warm to ambient temperature. After 4 hours, the mixture was poured into saturated ammonium chloride solution (20 mL) and extracted with ethyl acetate (30 mL). After drying the organics over anhydrous magnesium sulfate and filtration, the solvent was removed under reduced pressure. The resulting residue was purified by flash column chromatography on silica gel eluted with 15% ethyl acetate in hexanes to give N-(BOC)-(D,L)-3-(4'-bromophenyl)sulfonyl-nipecotic acid, ethyl ester (425 mg).

Step C

N-(BOC)-(D,L)-3-(4'-Bromophenyl)sulfonyl-nipecotic acid

N-(BOC)-(D,L)-3-(4'-Bromophenyl)sulfonyl-nipecotic acid, ethyl ester from Step B (91 mg, 0.19 mmol) was dissolved in methanol:water (3:1, 2 mL) and lithium hydroxide (8.8 mg, 0.21 mmol) was added. After stirring for 4 hours the mixture was poured into saturated ammonium chloride solution (10 mL) and extracted with ethyl acetate (15 mL). After drying the organics over anhydrous magnesium sulfate and filtration, the solvent was removed under reduced pressure to give N-(BOC)-(D,L)-3-(4'-bromophenyl)sulfonyl-nipecotic acid (81 mg, 0.18 mmol).

Step D

N-(N-(BOC)-3-(4'-Bromophenyl)sulfonyl-nipecotyl)-(L)-4-(2',6'-dimethoxyphenyl)-phenylalanine, tert-butyl ester N-(BOC)-(D,L)-3-(4'-Bromophenyl)sulfonyl-nipecotic acid from Step C was coupled to (L)-4-f2'-methoxyphenyl) phenylalanine, tert-butyl ester (332 mg, 0.91 mmol) according the procedure described in Example 1, Step B to give N-(N-(BOC)-3-(4'-bromophenyl)sulfonyl-nipecotyl)-(L)-4-(2',6'-dimethoxyphenyl)-phenylalanine, tert-butyl ester as two separable diastereomers: a less polar isomer (Isomer A) (35 mg), and a more polar isomer (Isomer B) (30 mg).

Step E

N-3-(4'-Bromophenyl)sulfonyl-nipecotyl-(L)-4-(2',6'-dimethoxyphenyl)phenyalanine (Isomer A)

N-(N-(BOC)-3-(4'-bromophenyl)sulfonyl-nipecotyl)-(L)-4-(2',6'-dimethoxyphenyl)-phenylalanine, tert-butyl ester (Isomer A) from Step D was treated with TFA according to the procedure described in Example 1, Step C to give N-3-(4'-bromophenyl)sulfonyl-nipecotyl-(L)-4-(2',6'-dimethoxyphenyl)phenylalanine (Isomer A). HPLC MS: 631 (M+H$^+$).

EXAMPLE 21

N-(3-(4'-Bromophenylsulfonyl)-nipecotyl)-(L)-4-(2',6'-dimethoxyphenyl)-phenylalanine (Isomer B)

N-(N-(BOC)-3-(4'-Bromophenyl)sulfonyl-nipecotyl)-(L)-4-(2',6'-dimethoxyphenyl)-phenylalanine, tert-butyl ester (Isomer B) from Example 20, Step D was treated with TFA according to the procedure described in Example 1, Step C to give N-3-(4'-bromophenyl)sulfonyl-nipecotyl-(L)-4-(2',6'-dimethoxyphenyl)-phenylalanine (Isomer A). RPLC MS: 631 (M+H$^+$).

EXAMPLES 22 AND 23

N-(3-(3'-bromophenyl)sulfonyl-nipecotyl)-(L)-4-(2',6'-dimethoxyphenyl)-phenylalanine (Isomer A and Isomer B)

The procedures described in Examples 20, Steps A to E were performed with 3-bromophenylsulfonyl chloride in place of 4-bromophenylsulfonyl chloride to give the two diastereomers of N-(3-(3'-bromophenyl)sulfonyl-nipecotyl)-(L)-4-(2',6'-dimethoxyphenyl)phenylalanine (Isomer A and Isomer B). HPLC MS: 631 (M+H$^+$).

EXAMPLES 24 AND 25

N-(3-(2'-bromophenyl)sulfonyl-nipecotyl)-(L)-4-(2',6'-dimethoxyphenyl)phenylalanine (Isomers A and B)

The procedures described in Examples 20, Steps A to E were performed with 2-bromophenylsulfonyl chloride in place of 4-bromophenylsulfonyl chloride to give the two diastereomers of N-(3-(2'-bromophenyl)sulfonyl-nipecotyl)-(L)-4-(2',6'-dimethoxyphenyl)phenylalanine (Isomer A and Isomer B). HPLC MS: 631 (M+H$^+$).

EXAMPLE 26 AND 27

N-(3-(1-Methylimidazole-4-sulfonyl)-nipecotyl)-(L)-4-(2',6'-dimethoxyphenyl)-phenylalanine (Isomers A and B)

The procedures described in Example 20, Steps A to E were performed with 1-methylimidazole-4-sulfonyl chloride in place of 4-bromophenylsulfonyl chloride and methanol in place of acetonitrile in Step A to give two separable diastereomers of N-(3-(1-methylimidazole-4-sulfonyl)-nipecotyl)-(L)-4-(2',6'-dimethoxyphenyl)phenylalanine: a less polar Isomer A and a more polar Isomer B. HPLC MS: 557 (M+H$^+$).

EXAMPLE 28

N-(3-(1-Methylimidazole-5-sulfonyl)-nipecotyl)-(L)-4-(2',6'-dimethoxyphenyl)-phenylalanine From Example 27, an additional isomer was isolated that was generated from 1-methylimidazole-5-sulfonyl chloride which was an impurity in the starting material in Step A. This isomer was determined to be N-(3-(1-methylimidazole-5-sulfonyl)-nipecotyl)-(L)-4-(2',6'-dimethoxyphenyl)phenylalanine.

HPLC MS: 557 (M+H$^+$).

EXAMPLE 29

N-(3-Methylsulfonyl-nipecotyl)-(L)-4-(2',6'-dimethoxyphenyl)phenylalanine (Isomers A and B)

The procedures described in Examples 20, Steps B to E were performed with methylsulfonyl fluoride in place of 4-bromophenylsulfonyl fluoride to give two separable diastereomers of N-(3-methylsuifonyl-nipecotyl)-(L)-4-(2',6'-dimethoxyphenyl)phenylalanine (Isomer A and Isomer B).

HPLC MS: 491 (M+H$^+$).

EXAMPLE 30

N-(3-(4'-benzylaminophenyl)sulfonyl-nipecotyl)-(L)-4-(2',6'-dimethoxyphenyl)-phenylalanine (Isomer A)

Step A

N-(N-(BOC)-3-(4'-Benzylaminophenyl)sulfonyl-nipecotyl)-(L)-4-(2',6'-dimethoxyphenyl)phenylalanine, tert-butyl ester.

N-(N-(BOC)-3-(4'-Bromophenyl)sulfonyl-nipecotyl)-(L)-4-(2',6'-dimethoxyphenyl)-phenylalanine, tert-butyl ester (Isomer A) from Example 20, Step D (27 mg, 0.03 mmol) was dissolved in toluene (1 mL) then racemic bis (diphenylphosphino)-1,1'-binaphthyl (2.1 mg, 0.003 mmol), sodium tert-butoxide (4 mg, 0.04 mmol) and benzylamine (5 $\mu$l, 0.05 mmol) were sequentially added. After degassing of this mixture, tris(dibenzylideneacetone)-dipalladium(0) (1.6 mg, 0.002 mmol) was added and the mixture warmed to 90° C. for 5 hours. The mixture was then poured into pH=7 buffer solution (1 mL) and extracted with ethyl acetate (3×3 mL). After drying the combined organic layers over anhydrous magnesium sulfate and filtration, the solvent was removed under reduced pressure. The resulting residue was purified by flash column chromatography on silica gel eluted with a gradient of 5–50% ethyl acetate in hexanes) to give a single isomer (Isomer A) of N-(N-(BOC)-3-(4'-benzylaminophenyl)sulfonyl-nipecotyl)-(L)-4-(2',6'-dimethoxyphenyl)phenylalanine, tert-butyl ester (14 mg).

Step B

N-(3-(4'-Benzylaminophenyl)sulfonyl-nipecotyl)-(L)-4-(2',6'-dimethoxyphenyl)phenylalanine (Isomer A)

The product from Step A was separately treated with TFA according to the procedure described in Example 1, Step C to give N-(3-(4'-benzylaminophenyl)sulfonyl-nipecotyl)-(L)-4-(2',6'-dimethoxyphenyl)phenylalanine (Isomer A).

HPLC MS: 657 (M+H$^+$).

EXAMPLE 31

N-(3-(4'-Benzylaminophenyl)sulfonyl-nipecotyl)-4-(2',6'-dimethoxyphenyl)phenylalanine (Isomers B and C)

N-(N-(BOC)-3-(4'-Bromophenyl)sulfonyl-nipecotyl)-(L)-4-(2',6'-dimethoxyphenyl)-phenylalanine, tert-butyl ester (Isomer B) from Example 20, Step D was treated according to the procedure described in Example 30, Step A to give a pair of isomers of N-(3-(4'-benzylaminophenyl) sulfonyl-nipecotyl)-4-(2',6'-dimethoxyphenyl) phenylalanine (Isomers B and C). N-(3-(4'- benzylaminophenyl)sulfonyl-nipecotyl)-4-(2',6'-dimethoxyphenyl)phenylalanine (Isomers B and C) were treated according to the procedure described in Example 1, Step C to afford N-(3-(4'-benzylaminophenyl)sulfonyl-nipecotyl)-4-(2',6'-dimethoxyphenyl)phenylalanine (Isomers B and C).

HPLC MS: 657 (M+H$^+$).

EXAMPLE 32

N-(3-(3'-Benzylaminophenyl)sulfonyl-nipecotyl)-4-(2',6'-dimethoxyphenyl)phenylalanine (Isomer A)

N-(N-(BOC)-3-(3'-Bromophenyl)sulfonyl-nipecotyl)-(L)-4-(2',6'-dimethoxyphenyl)phenylalanine, tert-butyl ester (Isomer A) from Example 22 was treated according to the procedures described in Example 30, Step A and B to give N-(3-(3'-benzylaminophenyl)sulfonyl-nipecotyl)-4-(2',6'-dimethoxyphenyl)phenylalanine (Isomer A) as a single isomer.

HPLC MS: 657 (M+H$^+$).

EXAMPLE 33

N-(3-(3'-Benzylaminophenyl)sulfonyl-nipecotyl)-4-(2',6'-dimethoxyphenyl)-phenylalanine (Isomers B-C)

N-(N-(BOC)-3-(3'-Bromophenyl)sulfonyl-nipecotyl)-(L)-4-(2',6'-dimethoxyphenyl)phenylalanine, tert-butyl ester (Isomer B) from Example 23 was treated according to the procedure described in Example 30, Step A to give a pair of isomers of N-(N-(BOC)-3-(3'-benzylaminophenyl)sulfonyl-nipecotyl)-4-(2',6'-dimethoxyphenyl)phenylalanine, tert-butyl ester (Isomers B and C). N-(N-(BOC)-3-(3'-benzylaminophenyl)sulfonyl-nipecotyl)-4-(2',6'-dimethoxyphenyl)phenylalanine, tert-butyl ester (Isomers B and C) was treated according to the procedure described in Example 1, Step C to afford N-(3-(3'-benzylaminophenyl)sulfonyl-nipecotyl)-4-(2',6'-dimethoxyphenyl)phenylalanine (Isomers B and C).

HPLC MS: 657 (M+H$^+$).

EXAMPLE 34

N-(3-(4'-Pyrrolidinophenyl)sulfonyl-nipecotyl)-(L)-4-(2',6'-dimethoxyphenyl)-phenylalanine (Isomer A)

N-(N-(BOC)-3-(4'-Bromophenyl)sulfonyl-nipecotyl)-(L)-4-(2',6'-dimethoxyphenyl)-phenylalanine, tert-butyl ester (Isomer A) from Example 20, Step D was treated according to the procedures described in Example 30 using pyrrolidine in place of benzylamine to give N-(3-(4'-pyrrolidinophenyl)sulfonyl-nipecotyl)-(L)-4-(2',6'-dimethoxyphenyl)phenylalanine (Isomer A).

HPLC MS: 622 (M+H$^+$).

EXAMPLE 35

N-(3-(4'-Pyrrolidinophenyl)sulfonyl-nipecotyl)-(L)-4-(2',6'-dimethoxyphenyl)phenylalanine (Isomer B)

N-(N-(BOC)-3-(4'-Bromophenyl)sulfonyl-nipecotyl)-(L)-4-(2',6'-dimethoxyphenyl)phenylalanine, tert-butyl ester (Isomer B) from Example 20, Step D was treated according to the procedures described in Example 30 using pyrrolidine in place of benzylamine to give N-(3-(4'-pyrrolidinophenyl)sulfonyl-nipecotyl)-(L)-4-(2',6'-dimethoxyphenyl)phenylalanine (Isomer B).

HPLC MS: 622 (M+H$^+$).

EXAMPLE 36

N-(3-(3'-Pyrrolidinophenyl)sulfonyl-nipecotyl)-(L)-4-(2',6'-dimethoxyphenyl)phenylalanine (Isomer A)

N-(N-(BOC)-3-(3'-Bromophenyl)sulfonyl-nipecotyl)-(L)-4-(2',6'-dimethoxyphenyl)-phenylalanine, tert-butyl ester (Isomer A) from Example 22 was treated according to the procedures described in Example 30 using pyrrolidine in place of benzylamine to give N-(3-(3'-pyrrolidinophenyl)sulfonyl-nipecotyl)-(L)-4-(2',6'-dimethoxyphenyl)phenylalanine (Isomer A).

HPLC MS: 622 (M+H$^+$).

EXAMPLE 37

N-(3-(3'-Pyrrolidinophenyl)sulfonyl-nipecotyl)-(L)-4-(2',6'-dimethoxyphenyl)-phenylalanine (Isomer B)

N-(N-(BOC)-3-(3'-Bromophenyl)sulfonyl-nipecotyl)-(L)-4-(2',6'-dimethoxyphenyl)phenylalanine, tert-butyl ester (Isomer B) from Example 23 was treated according to the procedures described in Example 30 using pyrrolidine in place of benzylamine to give N-(3-(3'-pyrrolidinophenyl)sulfonyl-nipecotyl)-(L)-4-(2',6'-dimethoxyphenyl)phenylalanine (Isomer B).

HPLC MS: 622 (M+H$^+$).

EXAMPLE 38

N-(3-(2-(Piperidinyl)ethyl)sulfonyl-nipecotyl)-(L)-4-(2',6'-dimethoxyphenyl)-phenylalanine Step A di(tert-butyldimethylsiloxyethyl) disulfide.

To a solution of 3.78 g (24.5 mmol) of di(hydroxyethyl) disulfide and 8.1 g (54 mmol) of TBSCl in 100 ml of CH$_2$Cl$_2$ at 0° C. was added 5.0 g (73.6 mmol) of imidazole. The reaction mixture was allowed to warm to room temperature overnight after which time it was concentrated to ¼ volume and diluted with EtOAc and quenched with 1M HCl. The layers were separated and the organic layer was washed with 1M HCl (3×100 mL), saturated NaHCO$_3$ (2×50 mL), brine (1×50 mL), and dried over anhydrous MgSO$_4$, and concentrated. The crude residue was purified by flash column chromatography on silica gel eluted with a gradient of 50–100% Et$_2$O in hexanes to give di(tert-butyldimethylsiloxyethyl) disulfide as a colorless oil. Residual tert-butyldimethylsiloxide was was removed by azeotroping with toluene.

500 MHz $^1$H NMR (CDCl$_3$): δ 3.85 (t, 4H); 2.82 (t, 4H); 0.93 (s, 18H); 0.05 (s, 12H).

Step B

N-(BOC)-3-(2-(tert-butyldimethylsitoxy)ethylthio)-nipecotic acid, benzyl ester.

N-(BOC)-3-(2-(tert-butyldimethylsiloxy)ethylthio)-nipecotic acid, benzyl ester was prepared by the procedures described in Reference Example 13 substituting (D,L)-nipecotic acid, benzyl ester for the ethyl ester and di(tert-butyldimethylsiloxyethyl) disulfide for diphenyl disulfide. The product was purified by flash column chromatography on silica gel eluted with a gradient of 25–50% Et$_2$O in hexanes.

500 MHz $^1$H NMR (CDCl$_3$): δ 7.40–7.30 (m, 5H); 5.20 (AB q, 2H); 4.0 (d, 1H); 3.62 (t, 2H); 3.50–3.40 (br s, 2H);

3.4 (m, 1H); 2.80–2.60 (m, 2H); 2.20 (br m, 1H); 1.84–1.78 (m, 2H); 1.60–1.45 (br m, 1H); 1.42 (s, 9H); 0.90 (s, 9H); 0.02 (s, 6H).

Step C

N-(BOC)-3-(2-(tert-butyldimethylsiloxy)ethylsulfonyl)-nipecotic acid, benzyl ester.

To a solution of 1.5 g (2.90 mmol) of N-(BOC)-3-(2-tert-butyl-dimethylsiloxy)ethylthio)-nipecotic acid, benzyl ester in 20 ml of $CH_2Cl_2$ at 0° C. was added 1.60 g (6.4 mmol, 70%) of m-CPBA. The reaction mixture was allowed to warm to room temperature and after 3 hours, the starting material had been consumed. The reaction mixture was diluted with EtOAc and was successively washed with 1M NaOH (4×50 mL), $NaHSO_3$ (1×50 mL), brine (1×50 mL), dried over anhydrous $MgSO_4$ and concentrated under reduced pressure. The residue was purified by flash column chromatography on silica gel eluted with a gradient of 25–50% $Et_2O$ in hexanes to give N-(BOC)-3-tert-butyldimethylsiloxyethylsulfonyl-nipecotic acid, benzyl ester as a colorless oil.

Step D

N-(BOC)-3-(2-(tert-butyldimethylsiloxy)ethylsulfonyl)-nipecotic acid.

A solution of 1.5 g (2.77 mmol) of N-(BOC)-3-(2-tert-butyldimethylsiloxy)ethylsulfonyl)-nipecotic acid, benzyl ester in 15 ml of EtOAc was stirred with Pd/C under 1 atm hydrogen for 3 hours. The reaction mixture was filtered through a pad of celite (EtOAc) and concentrated to give a colorless oil which crystallized. The crude N-(BOC)-3-(2-(tert-butyldimethylsiloxy)ethylsulfonyl)-nipecotic acid was used without further purification.

Step E

N-(N-(BOC)-3-(2-(tert-butyldimethylsiloxy)ethylsulfonyl)-nipecotyl)-(L)-4-(2',6'-dimethoxyphenyl)-phenylalanine, tert-butyl ester.

The title compound was prepared following the procedures described in General Method 1, using the following amounts: N-(BOC)-3-(2-(tert-butyl-dimethylsiloxy)ethylsulfonyl)-nipecotic acid (0.52 g, 1.14 mmol) from Step D, (L)-4-(2',6'-dimethoxyphenyl)phenylalanine, tert-butyl ester (0.45 g, 1.26 mmol) from Reference Example 4, HATU (0.45 g, 1.26 mmol), HOAt (0.23 g, 1.72 mmol), and DIPEA (0.30 g, 2.3 mmol).

Step F

N-(N-(BOC)-3-(2-hydroxyethylsulfonyl)-nipecotyl)-(L)-4-(2',6'-dimethoxyphenyl)-phenylalanine, tert-butyl ester.

To a solution of 0.80 g (24.5 mmol) of N-(N-(BOC)-3-(2-(tert-butyldimethylsiloxy)ethylsulfonyl)-nipecotyl)-(L)-4-(2',6'-dimethoxyphenyl)-phenylalanine, tert-butyl ester from Step E and 0.37 g (6.1 mmol) of acetic acid in 6.0 ml of THF at 0° C. was added 4.0 mL (4.0 mmol, 1M in THF) of TBAF. When the starting material was judged consumed by TLC (~5 h), the reaction mixture was diluted with EtOAc and aqueous $NaHCO_3$. The layers were separated and the organic layer was washed with saturated $NaHCO_3$ (4×50 mL), brine (1×50 mL), dried ($MgSO_4$), and concentrated. The crude residue was purified by silica gel chromatography (3:1 hexanes-$Et_2O$ then 3:1 $Et_2O$-hexanes then $Et_2O$ then EtOAc) to give the desired product as a colorless oil.

Step G

N-(N-(BOC)-3-(Vinylsulfonyl)-nipecotyl)-(L)-4-(2',6'-dimethoxyphenyl)phenylalanine, tert-butyl ester.

To a solution of 0.11 g (0.16 mmol) of N-(N-(BOC)-3-(2-hydroxy-ethylsulfonyl)-nipecotyl)-(L)-4-(2',6'-dimethoxyphenyl)phenylalanine, tert-butyl ester from Step F and 0.10 g (0.97 mmol) of TEA in 2.0 ml of $CH_2Cl_2$ at 0° C. was added 0.06 g (0.49 mmol) of MsCl. When the starting material was judged consumed by TLC (~1 h), the reaction mixture was diluted with EtOAc and 1M HCl. The layers were separated and the organic layer was washed with 1M HCl (2×10 mL), saturated $NaHCO_3$ (4×50 mL), brine (1×50 mL), dried ($MgSO_4$), and concentrated. The crude residue could be used directly in the next step as a mixture of diastereomers or the diastereomers could be separated by preparative layer TLC (1:1 hexanes-$Et_2O$ twice, then 3:1 $Et_2O$-hexanes twice) to give both diastereomers as colorless oils.

Step H

N-(N-(BOC)-3-(2-(Piperidinyl)ethylsulfonyl)-nipecotyl)-(L)-4-(2',6'-dimethoxyphenyl)phenylalanine, tert-butyl ester.

To a solution of 64 mg (0.10 mmol) of N-(N-(BOC)-3-(vinylsulfonyl)-nipecotyl)-(L)-4-(2',6'-dimethoxyphenyl) phenylalanine, tert-butyl ester from Step G in $CH_2Cl_2$ (or $CH_3CN$) (2 mL) at room temperature was added 30 µL (0.30 mmol) of piperidine. When the starting material was consumed as judged by TLC, the reaction mixture was concentrated and used without further purification. HPLC:MS 744.4 (M+).

Step I

N-(3-(2-(Piperidinyl)ethylsulfonyl)-nipecotyl)-(L)-4-(2',6'-dimethoxyphenyl)phenylalanine.

N-(N-(BOC)-3-(2-(Piperidinyl)ethylsulfonyl)-nipecotyl)-(L)-4-(2',6'-dimethoxyphenyl)phenylalanine, tert-butyl ester (47 mg, 0.063 mmol) from Step H (a mixture of diastereomers) was treated with TFA according to Example 1, Step C to give N-(3-(2-(piperidinyl)ethylsulfonyl)-nipecotyl)-(L)-4-(2',6'-dimethoxyphenyl) phenylalanine as a white solid. HPLC:MS 588.3 (M+).

EXAMPLE 39

N-(3-(2-(Morpholinyl)ethylsulfonyl)-nipecotyl)-(L)-4-(2',6'-dimethoxyphenyl)phenylalanine N-(3-(2-(Morpholinyl)ethylsulfonyl)-nipecotyl)-(L)-4-(2',6'-dimethoxyphenyl)phenylalanine was prepared by the procedures described in Example 38, substituting morpholine in place of piperidine in Step H.

HPLC:MS 590.3 (M+).

EXAMPLE 40

N-(3-(2-(3-Dimethylaminopropyl)amino) ethylsulfonyl)-nipecotyl)-(L)-4-(2',6'-dimethoxyphenyl)-phenylalanine N-(3-(2-(3-Dimethylaminopropyl)amino)ethylsulfonyl) nipecotyl)-(L)-4-(2',6'-dimethoxyphenyl)phenylalanine was prepared by the procedures described in Example 38, substituting 3-dimethylaminopropylamine in place of piperidine in Step H.

HPLC:MS 605.3 (M+).

EXAMPLE 41

N-(3-(3-Nitropropylsulfonyl)-nipecotyl)-(L)-4-(2',6'-dimethoxyphenyl)-phenylalanine Step A N-(N-(BOC)-3-(3-Nitropropylsulfonyl)-nipecotyl)-(L)-4-(2',6'-dimethoxyphenyl)phenylalanine, tert-butyl ester.

To a solution of N-(N-(BOC)-3-(vinylsulfonyl)-nipecotyl)-(L)-4-(2',6'-dimethoxyphenyl)phenylalanine, tert-butyl ester. (0.20 g, 0.30 mmol) from Example 38, Step G in 2 mL of $CH_3NO_2$ was added DBU (1 drop). After 44 h at room temperature, the reaction mixture was concentrated and the crude residue purified by flash column chromatography on silica gel eluted with a gradient of 25–75–100 Et$_2$O in hexanes to give the desired product as a colorless oil.

Step B

N-(3-(3-Nitropropylsulfonyl)-nipecotyl)-(L)-4-(2',6'-dimethoxyphenyl)phenylalanine.

N-(N-(BOC)-3-(3-Nitropropylsulfonyl)-nipecotyl)-(L)-4-(2',6'-dimethoxyphenyl)phenylalanine, tert-butyl ester (18 mg, 0.025 mmol) was treated with TFA according to the procedure described in Example 1, Step C to give N-(3-(3-nitropropylsulfonyl)-nipecotyl)-(L)-4-(2',6'-dimethoxyphenyl)phenylalanine (a mixture of diastereomers) as a white solid.

HPLC:MS 564.3 (M+).

EXAMPLE 42

N-(3-(2-(1-Imidazolyl)ethylsulfonyl)-nilpecotyl)-(L)-4-(2',6'-dimethoxyphenyl)phenylalanine Step A N-(N-(BOC)-3-(2-(1-Imidazolyl)ethylsulfonyl)-nipecotyl)-(L)-4-(2',6'-dimethoxyphenyl)phenylalanine, tert-butyl ester.

To a solution of N-(N-(BOC)-3-(vinylsulfonyl)-nipecotyl)-(L)-4-(2',6'-dimethoxyphenyl)-phenylalanine, tert-butyl ester (50 mg, 0.076 mmol) from Example 38, Step G and 15 mg (0.23 mmol) of imidazole in 1 mL of CH$_3$CN was added DBU (1 drop). After 23 h at room temperature, the reaction mixture was concentrated, and the crude residue purified by preparative TLC on silica gel eluted with EtOAc to give N-(N-(BOC)-3-(2-(1-imidazolyl)ethylsulfonyl)-nipecotyl)-(L)-4-(2',6'-dimethoxyphenyl)phenylalanine, tert-butyl ester as a colorless oil.

Step B

N-(3-Imidazolylethylsulfonyl-nipecotyl)-(L)-4-(2',6'-dimethoxyphenyl )phenylalanine.

N-(N-(BOC)-3-(2-(1-Imidazolyl)ethylsulfonyl)-nipecotyl)-(L)-4-(2',6'-dimethoxyphenyl)phenylalanine, tert-butyl ester (40 mg, 0.055 mmol) was treated with TFA according to the procedure described in Example 1, Step C to give N-(3-imidazolylethylsulfonyl-nipecotyl)-(L)-4-(2', 6'-dimethoxyphenyl)-phenylalanine (a mixture of diastereomers) as a white solid.

HPLC:MS 571.3 (M+).

EXAMPLE 43

N-(3-(2-Hydroxyethylsulfonyl)-nipecotyl)-(L)-4-(2', 6'-dimethoxyphenyl)-phenylalanine N-(N-(BOC)-3-(2-(tert-butyldimethylsiloxy) ethylsulfonyl)-nipecotyl)-(L)-4-(2',6'-dimethoxyphenyl) phenylalanine, tert-butyl ester (33 mg, 0.049 mmol) from Example 38, Step E was treated with TFA according to the procedure described in Example 1, Step C to give N-(3-(2-hydroxyethylsulfonyl)-nipecotyl)-(L)-4-(2',6'-dimethoxyphenyl)-phenylalanine as a white solid.

HPLC:MS 521.2 (M+H).

EXAMPLE 44

N-(3-Phenylsulfonyl-nipecotyl)-(L)-4-(2'-cyanophenyl)phenylalanine (Isomer A and Isomer B)

Step A

N-(3-Phenylsulfonyl-nipecotyl)-(L)-4-(2'-cyanophenyl) phenylalanine, methyl ester (Isomer A and Isomer B)

The two diastereomers of N-(3-phenylsulfonyl-nipecotyl)-(L)-4-(2'-cyanophenyl)phenylalanine, methyl ester (Isomer A and Isomer B) were prepared by the procedures described in Example 1 by coupling (L)-4-(2'-cyanophenyl)phenylalanine, methyl ester (Reference Example 1) with N-(BOC)-(D,L)-3-phenylsulfonyl-nipecotic acid (Ref. Example 13).

HPLC MS: 532 (M+H$^+$).

Step B

N-(3-Phenylsulfonyl-nipecotyl)-(L)-4-(2'-cyanophenyl) phenylalanine, (Isomer A and Isomer B)

The two diastereomers of N-(3-phenylsulfonyl-nipecotyl)-(L)-4-(2'-cyanophenyl)phenylalanine, methyl ester (Isomer A and Isomer B) were separately treated with sodium hydroxide according to the procedures described in Example 11, Step C to give N-(3-phenylsulfonyl-nipecotyl)-(L)-4-(2'-cyanophenyl)phenylalanine (Isomer A and Isomer B).

HPLC MS: 540 (M+Na$^+$).

EXAMPLE 45

N-(3-Phenylsulfonyl-nipecotyl)-(L)-4-(2',6'-dichloro-benzamido)phenylalanine (Isomers A and B)

Step A.

N-(N-(BOC)-3-phenylsulfonyl-nipecotyl)-(L)-4-(2',6'-dichloro-benzamido)phenylalanine, methyl ester.

N-(BOC)-(D,L)-3-phenylsulfonylnipecotic acid (129 mg, 0.35 mmol) from Reference Example 13 was coupled to (L)-4-(2',6'-dichlorobenzamido)-phenylalanine, methyl ester (127 mg, 0.35 mmol from Reference Example 12) according to the procedure described in Example 1, Step B to give an inseparable mixture of two isomers of N-(N-(BOC)-3-phenylsulfonyl-nipecotyl)-(L)-4-(2',6'-dichloro-benzamido)phenylalanine, methyl ester (44 mg).

Step B

N-(N-(BOC)-3-phenylsulfonyl-nipecotyl)-(L)-4-(2',6'-dichloro-benzamido)phenylalanine.

N-(N-(BOC)-3-Phenylsulfonyl-nipecotyl)-(L)-4-(2',6'-dichloro-benzamido)phenylalanine, methyl ester was treated with sodium hydroxide according the procedure described in Example 11, Step C to give N-(N-(BOC)-3-phenyl-sulfonyl-nipecotyl)-(L)-4-(2',6'-dichloro-benzamido)phenylalanine.

Step C

N-(3-Phenylsulfonyl-nipecotyl)-(L)-4-(2',6'-dichloro-benzamido)phenylalanine

N-(N-(BOC)-3-Phenylsulfonyl-nipecotyl)-(L)-4-(2',6'-dichloro-benzamido)phenylalanine was treated with TFA according the procedure described in Example 1, Step C to give N-(3-phenylsulfonyl-nipecotyl)-(L)-4-(2',6'-dichloro-benzamido)phenylalanine.

HPLC MS: 604 (M+H$^+$).

EXAMPLE 46

N-(3-Phenylsulfonyl-nipecotyl)-(L)-4-(1-pyrrolidino-carbonyloxy)phenylalanine (Isomer A)

Step A

N-(N-(BOC)-3-Phenylsulfonyl-nipecotyl)-(L)-4-(1-pyrrolidino-carbonyloxy)phenylalanine, tert-butyl ester (Isomer A)

N-(N-(BOC)-3-Phenylsulfonyl-nipecotyl)-(L)-tyrosine, tert-butyl ester (Isomer A) from Example 18, Step A (35 mg, 0.06 mmol) was dissolved in 1 mL of THF, then 71 μL (0.07 mmol) of a 1M solution of sodium hexamethyidisilazide in THF was added. The solution was warmed to 40° C. and stirred for 3 hours. Pyrrolidine carbamoyl chloride (25 mL, 0.18 mmol) was added, then the mixture was was stirred for a further 12 hours. The solution was diluted with 20 mL of ethyl acetate, washed with $H_2O$ (10 mL), and brine (1×75 mL), and dried over anhydrous $MgSO_4$. Purification by flash column chromatography on silica gel eluted with 20% EtOAc in hexanes gave N-(N-(BOC)-3-phenylsulfonyl-nipecotyl)-(L)-4-(1-pyrrolidino-carbonyloxy)phenylalanine, tert-butyl ester (Isomer A) (26 mg).

Step B.

N-(3-phenylsulfonyl-nipecotyl)-(L)-4-(1-pyrrolidino-carbonyloxy)-phenylalanine (Isomer A)

N-(N-(BOC)-3-Phenylsulfonyl-nipecotyl)-(L)-4-(1-pyrrolidino-carbonyloxy)phenylalanine, tert-butyl ester (Isomer A) (26 mg, 0.04 mmol) was treated with HCl (1 mL, 4M in dioxane) with warming to 40° C. After 3 days the solvents were removed under reduced pressure. The residue passed through a short plug of silica gel, eluted with 5% methanol in methylene chloride to yield N-(3-phenylsulfonyl-nipecotyl)-(L)-4-(1-pyrrolidino-carbonyloxy)phenylalanine (Isomer A) (5 mg).

HPLC MS: 530 (M+H$^+$).

EXAMPLE 47

N-(3-Phenylsulfonyl-nipecotyl)-(L)-4-(1-pyrrolidino-carbonyloxy)phenylalanine (Isomer B)

N-(N-(BOC)-3-Phenylsulfonyl-nipecotyl)-(L)-tyrosine, tert-butyl ester (Isomer B) from Example 19, Step A was treated according to the procedures described in Example 46 to give N-(3-phenylsulfonyl-nipecotyl)-(L)-4-(1-pyrrolidino-carbonyloxy)phenylalanine (Isomer B) (39 mg).

HPLC MS: 530 (M+H$^+$).

EXAMPLE 48

N-(3-Phenylsulfonyl-nipecotyl)-4-(2',6'-dimethoxyphenyl)-2-hydroxyphenylalanine

Step A

2-Benzyloxy-4-chlorobenzoic acid, benzyl ester.

To a solution of 7.0 g (40.6 mmol) 2-hydroxy-4-chlorobenzoic acid in 150 ml of dry DMF was added 16.8 g (122 mmol) of $K_2CO_3$ followed by the dropwise addition of 15.2 g (89.2 mmol) of benzyl bromide. The reaction mixture was warmed to 50° C. and stirred overnight. After 16h, the reaction mixture was diluted with $Et_2O$ and $H_2O$ and the layers were separated. The aqueous layer was extracted with $Et_2O$ (2×) and the combined organic layers were successively washed with 1N HCl (3×100 ml), saturated $NaHCO_3$ solution (2×50 ml) and brine (1×50 ml). The solution was dried over anhydrous $MgSO_4$ and concentrated to give 2-benzyloxy-4-chlorobenzoic acid, benzyl ester as a pale yellow solid which was used without further purification.

500 MHz $^1$H NMR (CDCl$_3$): 7.80 (d, 1H); 7.50–7.30 (m, 10H); 7.05 (s, 1H); 7.0 (d, 1H); 5.38 (s, 2H); 5.18 (s, 2H).

Step B 4-(2',6'-Dimethoxyphenyl)-2-benzyloxy-benzoic acid, benzyl ester.

A mixture of of 2-benzyloxy-4-chlorobenzoic acid, benzyl ester (1.0)g, 2.83 mmol), 2,6-dimethoxybenzene boronic acid (0.62 g, 3.4 mmol), Pd$_2$dba$_3$ (0.26 g, 0.28 mmol), Cs$_2$CO$_3$ (1.38 g, 4.2 mmol), and t-Bu$_3$P (0.12 g, 0.57 mmol) was dissolved in 8.0 mL of THF and warmed to reflux for 24 h. The reaction mixture was cooled, diluted with Et$_2$O and H$_2$O and the layers were separated. The organic layer was successively washed with 1N HCl (2×100 ml), saturated NaHCO$_3$ solution (2×50 ml), brine (1×50 ml), dried over anhydrous MgSO$_4$ and concentrated. The residue was purified by flash column chromatography on silica gel eluted with a gradient of 25–50% Et$_2$O in hexanes to give 4-(2',6'-dimethoxyphenyl)-2-benzyloxy-benzoic acid, benzyl ester as a pale yellow oil.

500 MHz $^1$H NMR (CDCl$_3$): δ 7.95 (d, 1H); 7.50–7.30 (m, 11H); 7.05 (s, 1H); 7.0 (d, 1H); 6.63 (d, 2H); 5.40 (s, 2H); 5.18 (s, 2H); 3.65 (s, 6H).

Step C 4-(2',6'-dimethoxyphenyl)-2-benzyloxy-benzyl alcohol.

To a solution of 4-(2',6'-dimethoxyphenyl)-2-benzyloxy-benzoic acid, benzyl ester (0.72 g, 1.58 mmol) in 7.0 ml of CH$_2$Cl$_2$ at −78° C. was added 3.50 mL (3.5 mmol, 1M in toluene) of DIBAL-H. The reaction mixture was allowed to slowly warm to room temperature overnight. After 18 h, the reaction was quenched with saturated Rochelle's solution, diluted with EtOAc and the layers were separated. The organic layer was successively washed with 1N HCl (2×100 ml), saturated NaHCO$_3$ solution (2×50 ml), brine (1×50 ml), dried (MgSO$_4$) and concentrated. The residue was purified by silica gel chromatography eluted with 25% Et$_2$O in hexanes and gave 4-(2',6'-dimethoxyphenyl)-2-benzyloxy-benzyl alcohol as a white solid.

500 MHz $^1$H NMR (CDCl$_3$): δ 7.50–7.30 (m, 7H); 7.0 (m, 2H); 6.62 (d, 2H); 5.15 (s, 2H); 4.80 (s, 2H); 3.72 (s, 6H).

Step D 4-(2',6'-Dimethoxyphenyl)-2-benzyloxyphenylalanine, tert-butyl ester, benzophenone imine.

To a solution of 4-(2',6'-dimethoxyphenyl)-2-benzyloxy-benzyl alcohol (0.40 g, 1.14 mmol) and Ph$_3$P (0.45 g, 1.71 mmol) in CH$_2$Cl$_2$ (6 mL) at 0° C. was added NBS (0.26 g, 48 mmol). After 1 h at 0° C., TLC eluted with 25% Et$_2$O in hexanes indicated that the starting material had been consumed. The reaction mixture was concentrated under reduced pressure and the crude unstable benzyl bromide was used directly in the next reaction.

To a mixture of glycine, tert-butyl ester, benzophenone imine (0.50 g, 1.71 mmol) and BnNEt$_3$Cl (0.10 g) in toluene/50% aq NaOH (1:1 v/v, 10 ml) was added the crude benzyl bromide in toluene (5 mL). The reaction mixture was stirred vigorously at room temperature for 6 h and then diluted with toluene and H$_2$0. The aqueous layer was extracted with toluene (2×) and the combined organic extracts were successively washed with saturated NaHCO$_3$ solution (2×100 ml), brine (1×50 ml), dried over anhydrous MgSO$_4$ and concentrated. The residue was purified by flash column chromatography on silica gel eluted with a gradient of 25–50% Et$_2$O in hexanes and gave 4-(2',6'-dimethoxyphenyl)-2-benzyloxyphenylalanine, tert-butyl ester, benzophenone imine as a pale yellow oil.

Step E 4-(2',6'-Dimethoxyphenyl)-2-benzyloxyphenylalanine, tert-butyl ester.

To a solution of 4-(2',6'-dimethoxyphenyl)-2-benzyloxyphenylalanine, tert-butyl ester, benzophenone imine (0.50 g, 0.78 mmol) in THF (8 mL) was added 1M HCl (6 mL). The reaction mixture was stirred at room temperature until the starting material was consumed as judged by TLC analysis. The reaction mixture was diluted with EtOAc and the aqueous phase was adjusted to pH~9 with 1M NaOH. The layers were separated and the organic layer was dried over anhydrous $MgSO_4$ and concentrated. The crude 4-(2',6'-dimethoxyphenyl)-2-benzyloxyphenylalanine, tert-butyl ester was used without further purification.

Step F

N-(N-(BOC)-3-Phenylsulfonyl-nipecotyl)-4-(2',6'-dimethoxyphenyl)-2-benzyloxyphenylalanine, tert-butyl ester.

Following the procedure described in Example 1, Step B, 4-(2',6'-dimethoxyphenyl)-2-benzyloxyphenylalanine, tert-butyl ester (200 mg, 0.43 mmol) was coupled to N-(BOC)-(D,L)-3-phenylsulfonyl-nipecotic acid (238 mg, 0.65 mmol) in the presence of HATU (233 mg, 0.65 mmol), HOAt (117 mg, 0.86 mmol), and DIEA (167 mg, 1.3 mmol). The crude product was purified by flash column chromatography on silica gel eluted with a gradient of 25–50% $Et_2O$ in hexanes to give N-(N-(BOC)-3-phenylsulfonyl-nipecotyl)-4-(2',6'-dimethoxyphenyl)-2-benzyloxyphenylalanine, tert-butyl ester as a colorless oil.

HPLC:MS 815.4 (M+H).

Step G

N-(3-Phenylsulfonyl-nipecotyl)-4-(2',6'-dimethoxyphenyl)-2-benzyloxyphenylalanine.

N-(N-(BOC)-3-phenylsulfonyl-nipecotyl)-4-(2',6'-dimethoxyphenyl)-2-benzyloxyphenylalanine, tert-butyl ester (74 mg, 0.091 mmol) was treated with TFA according to procedure described in Example 1, Step C to yield N-(3-phenylsulfonyl-nipecotyl)-4-(2',6'-dimethoxyphenyl)-2-benzyloxyphenylalanine.

HPLC:MS 659.2 (M+H).

Step H

N-(3-Phenylsulfonyl-nipecotyl)-4-(2',6'-dimethoxyphenyl)-2-hydroxyphenylalanine.

A mixture of N-(3-phenylsulfonyl-nipecotyl)-4-(2',6'-dimethoxyphenyl)-2-benzyloxyphenylalanine (36 mg, 0.055 mmol) and 10% Pd/C (10 mg) were stirred vigorously under 1 atm of $H_2$ until the starting material was consumed as judged by reverse phase HPLC analysis. The mixture was filtered through a pad of celite which was washed with MeOH and concentrated. The filtrate was triturated with $Et_2O$ to afford N-(3-phenylsulfonyl-nipecotyl)-4-(2',6'-dimethoxyphenyl)-2-hydroxyphenylalanine as a solid.

HPLC:MS 569.2 (M+H).

EXAMPLE 49

N-(3-Phenylsulfonyl-nipecotyl)-(L)-4-(2',6'-dimethoxyphenyl)-2-nitrophenylalanine Step A 4-(2',6'-Dimethoxyphenyl)-2-nitrobenzyl alcohol.

A mixture of 5.0 g (26.7 mmol) of 2-nitro-4-chlorobenzyl alcohol, 6.33 g (34.8 mmol) of 2,6-dimethoxybenzene boronic acid, 0.73 g (0.80 mmol) of $Pd_2dba_3$, 11.3 g (34.8 mmol) of $Cs_2CO_3$, and 0.45 g (1.60 mmol) of $Cy_3P$ was dissolved in 100 mL of dioxane and warmed to reflux for 18 h. The reaction mixture was cooled, filtered through a pad of silica gel which was washed with $Et_2O$ and concentrated. The residue was purified by flash column chromatography on silica gel eluted with a gradient of 25–50% $Et_2O$ in hexanes and gave 4-(2',6'-dimethoxyphenyl)-2-nitrobenzyl alcohol as a pale yellow solid.

Step B 4-(2',6'-Dimethoxyphenyl)-2-nitrobenzyl bromide.

To a solution of 1.8 g (6.23 mmol) of 4-(2',6'-dimethoxyphenyl)-2-nitrobenzyl alcohol and 2.3 g (8.72 mmol) of $Ph_3P$ in $CH_2Cl_2$ (20 mL) at 0° C. was added 1.32 g (7.5 mmol) of NBS. The reaction mixture was stirred at 0° C. for 30 min at which time TLC analysis (eluted with 25% $Et_2O$ in hexanes) indicated that the starting material had been consumed. The reaction mixture was concentrated and the crude residue was purified by flash column chromatography on silica gel eluted with 50% $Et_2O$ in hexanes to give 4-(2',6'-dimethoxyphenyl)-2-nitrobenzyl bromide as a pale yellow solid. Trituration with hexanes gave the product as a white solid.

Step C (L)-4-(2',6'-dimethoxyphenyl)-2-nitrophenylalanine, tert-butyl ester, benzophenone imine.

To a mixture of 0.55 g (1.85 mmol) of glycine, tert-butyl ester, benzophenone imine, 0.11 g (0.19 mmol) of Corey's catalyst (O-allyl-N-(9-anthracenylmethyl)cinchonidinium bromide), and 3.10 g (18.5 mmol) of CsOH in $CH_2Cl_2$ (10 ml) at −78° C. was added a solution of 0.78 g (2.2 mmol) of 4-(2',6'-dimethoxyphenyl)-2-nitrobenzyl bromide in $CH_2Cl_2$ (5 mL). The reaction mixture was allowed to slowly warm to −20° C. overnight and was then diluted with EtOAc and $H_2O$ and warmed to room temperature. The layers were separated and the aqueous layer was extracted with EtOAc (2×). The combined organic layers were successively washed with brine (1×50 ml), dried over anhydrous $MgSO_4$ and concentrated. The residue was purified by flash column chromatography on silica gel eluted with a gradient of 25–75% Et2O in hexanes to give (L)-4-(2',6'-dimethoxyphenyl)-2-nitro-phenylalanine, tert-butyl ester, benzophenone imine as a pale yellow oil.

Step D (L)-4-(2',6'-dimethoxyphenyl)-2-nitrophenylalanine, tert-butyl ester.

To a solution of 1.5 g (2.65 mmol) of (L)-4-(2',6'-dimethoxyphenyl)-2-nitrophenylalanine, tert-butyl ester, benzophenone imine in THF (20 mL) was added 1M HCl (20 mL). The reaction mixture was stirred at room temperature until the starting material was consumed as judged by TLC analysis. The reaction mixture was diluted with EtOAc and the aqueous phase was adjusted to pH~9 with 1M NaOH. The layers were separated and the organic layer was dried ($MgSO_4$) and concentrated. The crude (L)-4-(2',6'-dimethoxyphenyl)-2-nitrophenylalanine, tert-butyl ester was used in the subsequent reaction without further purification.

Step E

N-(N-(BOC)-3-Phenylsulfonyl-nipecotyl)-(L)-4-(2',6'-dimethoxyphenyl)-2-nitrophenylalanine, tert-butyl ester.

Following the procedure described in Example 1, Step B, (L)-4-(2',6'-dimethoxyphenyl)-2-nitrophenylalanine, tert-butyl ester (100 mg, 0.25 mmol) was coupled to N-(BOC)-(D,L)-3-phenylsulfonyl-nipecotic acid (100 mg, 0.27 mmol) in the presence of HATU (98 mg, 0.27 mmol), HOAt (51 mg, 0.37 mmol), and i-$Pr_2NEt$ (80 mg, 0.62 mmol). The crude product was purified by flash column chromatography on silica gel eluted with a gradient of 50–75% $Et_2O$ in hexanes to give N-(N-(BOC)-3-phenylsulfonyl-nipecotyl)-(L)-4-(2',6'-dimethoxyphenyl)-2-nitrophenylalanine, tert-butyl ester as a colorless oil.

Step F
N-(3-Phenylsulfonyl-nipecotyl)-(L)-4-(2',6'-dimethoxyphenyl)-2-nitrophenylalanine.

N-(N-(BOC)-3-Phenylsulfonyl-nipecotyl)-(L)-4-(2',6'-dimethoxyphenyl)-2-nitrophenylalanine, tert-butyl ester (50 mg, 0.0.66 mmol) was treated with TFA according to procedure described in Example 1, Step C to yield N-(3-phenylsulfonyl-nipecotyl)-(L)-4-(2',6'-dimethoxyphenyl)-2-nitrophenylalanine.

HPLC:MS 598.3 (M+).

EXAMPLE 50

N-(3-Phenylsulfonyl-nipecotyl)-(L)-4-(2'-methoxy-6'-cyano-phenyl)-phenylalanine (Isomer A)

Step A
N-(N-(BOC)-3-Phenylsulfonyl-nipecotyl)-(L)-4-(2'-methoxy-6'-cyano-phenyl)-phenylalanine, tert-butyl ester (Isomer A and Isomer B).

N-(BOC)-(D,L)-3-phenylsulfonylnipecotic acid (0.65 g, 1.8 mmol) (Reference Example 13) was coupled to (L)-4-(2'-methoxy-6'-cyano-phenyl)phenylalanine, tert-butyl ester (0.41 g, 1.2 mmol) (Reference Example 8) according to the procedure described in Example 1, Step B to give, following flash column chromatography on silica gel eluted with 25% EtOAc in hexanes, two diastereomers Isomer A (less polar) and Isomer B (more polar). Isomer B was further purified by HPLC (YMC Pro Pack C18 100×20 mm 5 μm, 120 Å column, 20 ml/min, 10–100% $CH_3CN/H_2O$ 0.1% TFA).

Step B
N-(3-Phenylsulfonyl-nipecotyl)-(L)-4-(2'-methoxy-6'-cyano-phenyl)-phenylalanine (Isomer A).

N-(N-(BOC)-3-Phenylsulfonyl-nipecotyl)-(L)-4-(2'-methoxy-6'-cyano-phenyl)phenylalanine, tert-butyl ester (Isomer A) was treated with TFA by the procedure described in Example 1, Step C to provide N-(N-(BOC)-3-phenylsulfonyl-nipecotyl)-(L)-4-(2'-methoxy-6'-cyano-phenyl)phenylalanine (Isomer A). The product was further purified by HPLC (YMC Pro Pack C18 100×20 mm 5 μm, 120 Å column, 20 mL/min, 10–100% $CH_3CN/H_2O$ 0.1% TFA).

$^1$H-NMR (400 MHz, $CD_3OD$): 0.90 (m, 1H); 1.80 (m, 1H); 2.25–2.43 (m, 2H); 2.85 (dt, 1H); 3.09–3.26 (m, 2h); 3.41 (m, 2H); 3.76 (s, 3H); 4.92 (m, 1h); 7.32–7.42 (m, 6H); 7.45 (t, 1H); 7.60 (t, 2H); 7.80 (t, 1H); 8.01 (d, 2H). FABMS: 549 observed (M$^+$+1).

EXAMPLE 51

N-(3-Phenylsulfonyl-nipecotyl)-(L)-4-(2'-methoxy-6'-cyano-phenyl)-phenylalanine (Isomer B)

N-(N-(BOC)-3-Phenylsulfonyl-nipecotyl)-(L)-4-(2'-methoxy-6'-cyano-phenyl)-phenylalanine, tert-butyl ester (Isomer A) was treated with TFA by the procedure described in Example 1, Step C to provide N-(N-(BOC)-3-phenylsulfonyl-nipecotyl)-(L)-4-(2'-methoxy-6'-cyano-phenyl)-phenylalanine (Isomer B). The product was further purified by HPLC (YMC Pro Pack C18 100×20 mm 5 μm, 120 Å column, 20 mL/min, 10–100% $CH_3CN/H_2O$ 0.1% TFA).

$^1$H-NMR (400 MHz, $CD_3OD$): 2.05 (m, 2H); 2.35 (m, 1H); 3.00 (m, 2H); 3.25 (m, 4H); 3.45 (m, 1H); 3.42 (s, 3H); 4.56 (dd, 1H); 7.18 (d, 2H); 7.28–7.55 (m, 7H); 7.61 (m, 3H). FABMS: 549 observed (M$^+$+1).

EXAMPLE 52

N-(3-Phenylsulfinyl-nipecotyl)-(L)-4-(2',6'-dimethoxyphenyl)phenylalanine

N-(N-(BOC)-3-Phenylthio-nipecotyl)-(L)-4-(2',6'-dimethoxyphenyl)-phenylalanine, tert-butyl ester (Isomer B) (0.09 g, 0.13 mmol) from Example 3, Step A was dissolved in 2 mL of methylene chloride at 0° C. and was treated with m-chloro-peroxybenzoic acid (22 mg, 0.13 mmol). After 45 minutes the reaction mixture was diluted with methylene chloride, washed with saturated $NaHCO_3$ solution and brine, and then dried over anhydrous $MgSO_4$. The mixture was filtered and the filtrate was concentrated in vacuo. The residue was purified by MPLC on silica gel eluted 10–90% EtOAc in hexanes to give 60 mg of N-(3-phenylsulfinyl-nipecotyl)-(L)-4-(2',6'-dimethoxyphenyl) phenylalanine as a mixture of diastereomeric sulfoxides. The product was treated with TFA as described in Example 1, Step C and purified by HPLC.

FABMS: 537 observed (M$^+$+1).

EXAMPLE 53

N-(3-Phenylsulfonyl-nipecotyl)-(L)-4-(2'-methoxy-6'-dimethylaminophenyl)-phenylalanine N-(BOC)-(D,L)-3-Phenylsulfonylnipecotic acid (0.13 g, 0.36 mmol) from Reference Example 13 was coupled with (L)-4-(2'-methoxy-6'-dimethylaminophenyl)phenylalanine, tert-butyl ester (0.09 g (0.24 mmol) from Reference Example 10 by the procedure described in Example 1, Step B to give N-(3-phenylsulfonyl-nipecotyl)-(L)-4-(2'-methoxy-6'-dimethylaminophenyl)-phenylalanine, tert-butyl ester which was subsequently treated with TFA according to the procedure described in Example 1, Step C to yield N-(3-phenylsulfonyl-nipecotyl)-(L)-4-(2'-methoxy-6'-dimethylaminophenyl)-phenylalanine. The final product, N-(3-phenylsulfonyl-nipecotyl)-(L)-4-(2'-methoxy-6'-dimethylaminophenyl)phenylalanine, was purified by HPLC.

FABMS: 566 observed (M$^+$+1).

EXAMPLE 54

N-(3-Phenylsulfonyl-nipecotyl)-(L)-4-(2'-methoxy-6'-hydroxyphenyl)-phenylalanine N-(BOC)-(D,L)-3-phenylsulfonylnipecotic acid (0.17 g, 0.48 mmol) from Reference Example 13 was coupled with (L)-4-(2'-methoxy-6'-hydroxyphenyl)-phenylalanine, tert-butyl ester (0.11 g, 0.33 mmol) from Reference Example 11 by the procedure described in Example 1, Step B to give, after purification by MPLC on silica gel eluted with 10–90% EtOAc in hexanes, N-(N-(BOC)-3-phenylsulfonyl-nipecotyl)-(L)-4-(2'-methoxy-6'-hydroxyphenyl)-phenylalanine, tert-butyl ester (103 mg) as a mixture of diastereomers which was subsequently treated with TFA according to the procedure described in Example 1, Step C and purified by HPLC to afford N-(3-phenylsulfonyl-nipecotyl)-(L)-4-(2'-methoxy-6'-hydroxyphenyl) phenylalanine.

FABMS: 539 observed (M$^+$+1).

EXAMPLE 55

N-(3-Phenylsulfonyl-nipecotyl)-(L)-4-(2'-(methoxy-6'-ethylphenyl)-phenylalanine

N-(BOC)-(D,L)-3-phenylsulfonylnipecotic acid (0.05 g, 0.14 mmol) from Reference Example 13 was coupled with (L)-4-(2'-(methoxy-6'-ethylphenyl)-phenylalanine, tert-butyl ester (0.033 g (0.09 mmol) from Reference Example 9 by the procedure described in Example 1, Step B to give, after purification by MPLC on silica gel eluted with 10–90% EtOAc in hexanes, N-(3-phenylsulfonyl-nipecotyl)-(L)-4-

(2'-(methoxy-6'-ethylphenyl)-phenylalanine, tert-butyl ester (35 mg) as a mixture of diastereomers which was subsequently treated with TFA according to the procedure described in Example 1, Step C and purified by HPLC to afford N-(3-phenylsulfonyl-nipecotyl)-(L)-4-(2'-methoxy-6'-ethylphenyl)-phenylalanine.

FABMS: 551 observed ($M^+ + 1$).

EXAMPLE 56

N-(3-Benzylsulfonyl-nipecotyl)-(L)-4-(2',6'-dimethoxyphenyl)-phenylalanine

Step A

N-(BOC)-3-Benzylthio-nipecotic acid, ethyl ester.

N-(BOC)-3-Benzylsulfonyl-nipecotic acid, ethyl ester was prepared by the procedure described in ReferenceExamrple 13, Step B with lithium hexamethyldisilazide used in place of potassium hexamethyldisilazide and dibenzyl disulfide used in place of diphenyl disulfide. The product (2.1 g) was isolated by flash column chromatography on silica gel eluted with 10% EtOAc in hexanes.

Step B

N-(BOC)-3-Benzylthio-nipecotic acid.

N-(BOC)-3-Benzylsulfonyl-nipecotic acid, ethyl ester (0.57 g, 1.5 mmol) was saponified by dissolution in 3 mL of ethanol and 3 mL of water to which 5 equivalent of lithium hydroxide was added. The solution was heated at 60° C. for 4 hours, acidified with 1N HCl and extracted with ethyl acetate. The organic phase was dried over anhydrous MgSO4, filtered and was concentrated in vacuo to give N-(BOC)3-benzylthio-nipecotic acid (0.52 g).

Step C

N-(N-BOC-3-Benzylthio-nipecotyl)-(L)-4-(2',6'-dimethoxyphenyl)-phenylalanine, tert-butyl ester.

N-(BOC)-3-Benzylthio-nipecotic acid (0.52 g, 1.4 mmol) was coupled with (L)-4-(2',6'-dimethoxyphenyl) phenylalanine, tert-butyl ester (0.63 g, 1.7 mmol) from Reference Example 4 according to the procedure described in Example 1, Step B to afford, after purification by MPLC on silica gel eluted with 10–90% EtOAc in hexanes, N-(N-BOC-3-benzylthio-nipecotyl)-(L)-4-(2',6'-dimethoxyphenyl)-phenylalanine, tert-butyl ester (0.66 g).

Step D

N-(N-(BOC)-3-Benzylsulfonyl-nipecotyl)-(L)-4-(2',6'-dimethoxyphenyl)-phenylalanine, tert-butyl ester.

N-(N-(BOC)-3-Benzylthio-nipecotyl)-(L)-4-(2',6'-dimethoxyphenyl)-phenylalanine, tert-butyl ester was oxidized according to the procedure described in Reference Example 13, Step D to afford, after purification by MPLC on silica gel eluted with 10–90% EtOAc in hexanes, N-(N-(BOC)-3-benzylsulfonyl-nipecotyl)-(L)-4-(2',6'-dimethoxyphenyl)-phenylalanine, tert-butyl ester (0.23 g).

Step E

N-(3-Benzylsulfonyl-nipecotyl)-(L)-4-(2',6'-dimethoxyphenyl)-phenylalanine.

N-(N-(BOC)-3-Benzylsulfonyl-nipecotyl)-(L)-4-(2',6'-dimethoxyphenyl)-phenylalanine, tert-butyl ester was treated with TFA by the procedure described in Example 1, Step C to provide N-(3-benzylsulfonyl-nipecotyl)-(L)-4-(2',6'-dimethoxyphenyl)phenylalanine.

FABMS: 567 observed ($M^+ + 1$).

EXAMPLE 57

N-(3-Phenylsulfonyl-nipecotyl)-(L)-4-(1-piperazinylcarbonyl)-phenylalanine (Isomer A)

Step A

N-(FMOC)-(L)-4-tert-butyloxycarbonyl-phenylalanine, methyl ester.

To a solution of N-(FMOC)-(L)-4-tert-butyloxycarbonyl-phenylalanine (4.6 g, 9.4 mmol) in methylene chloride and methanol (50 mL each) at 0° C. was added TMSCHN$_2$ until a yellow color persisted (2 M, 15 mL, 14 mmol). After stirring at room temperature for 30 min, the mixture was concentrated under reduced pressure to give N-(FMOC)-(L)-4-tert-butyloxycarbonyl-phenylalanine, methyl ester (5.0 g) and was used without further purification.

Step B

N-(FMOC)-(L)-4-carboxyphenylalanine, ($C_\alpha$)-methyl ester.

To a solution of N-(FMOC)-(L)-4-tert-butyloxycarbonyl-phenylalanine, methyl ester (5.0 g, 10 mmol) in 100 mL of methylene chloride was added TFA (38 mL, 0.50 mol) mL at 0° C. After stirring at room temperature overnight, the mixture was concentrated under reduced pressure to give N-(FMOC)-(L)-4-carboxy-phenylalanine, ($C_\alpha$)-methyl ester (4.4 g) and was used without further purification.

HPLC-MS: m/e 446 ($M+H^+$).

Step C

N-(FMOC)-(L)-4-(4-(BOC)-1-Piperazinylcarbonyl)-phenylalanine, methyl ester

To a solution of N-(FMOC)-(L)-4-carboxyphenylalanine, ($C_\alpha$)-methyl ester (3.4 g, 7.6 mmol) and N-(BOC)-piperazine (1.4 g, 7.6 mmol) in 50 mL of methylene chloride at 0° C. was added DIEA (2.7 mL, 15 mmol) and PyBOP (4.2 mg, 8.0 mmol). After stirring at room temperature for 2 h, TLC indicated complete consumption of the starting material. The reaction mixture was then concentrated under reduced pressure, and the residue was purified by flash column chromatography on silica gel eluted with 20% acetone in hexane to give N-(FMOC)- (L)-4-(4-(BOC)-1-piperazinylcarbonyl)phenylalanine, methyl ester (4.0 g, 84%).

HPLC-MS: m/e 614 ($M+H^+$).

Step D (L)-4-(4-(BOC)-1-piperazinylcarbonyl)-phenylalanine, methyl ester.

To a solution of N-(FMOC)-(L)-4-(4-(BOC)-1-piperazinylcarbonyl)-phenylalanine, methyl ester (4.0 g, 6.5 mmol) in methylene chloride (40 mL) was added diethylamine (13 mL, 0.13 mol). After stirring at room temperature overnight, the reaction mixture was concentrated, and the residue was purified on a silica gel column eluting with methylene chloride to 1:20 methanol/methylene chloride to give (L)-4-(4-(BOC)-1-piperazinylcarbonyl)-phenylalanine, methyl ester (2.2 g, 89%).

HPLC-MS: m/e 392 ($M+H^+$).

Step E

N-(3-Phenylthio-nipecotyl)-(L)-4-(4-(BOC)-1-Piperazinylcarbonyl)-phenylalanine, methyl ester.

N-(BOC)-(D,L)-3-Phenylthio-nipecotic acid, sodium salt from Example 1, Step A was coupled with (L)-4-(4-(BOC)-1-piperazinylcarbonyl)-phenylalanine, methyl ester (0.05 g) according to the procedure described in Example 1, Step B to afford, after purification by flash column chromatography on silica gel eluted with 50% EtOAc in hexanes, the two diastereomers of N-(3-phenylthio-nipecotyl)-(L)-4-(4-(BOC)-1-piperazinylcarbonyl)-phenylalanine, methyl ester (Isomer A, less polar, 45 mg and Isomer B, more polar, 33 mg).

Step F
N-(3-Phenylsulfonyl-nipecotyl)-(L)-4-(4-(BOC)-1-piperazinylcarbonyl)phenylalanine, methyl ester (Isomer A).

N-(3-Phenylthio-nipecotyl)-(L)-4-(4-(BOC)-1-piperazinylcarbonyl)-phenylalanine, methyl ester was oxidized according to the procedure described in Example 5, Step A to afford N-(3-phenylsulfonyl-nipecotyl)-(L)-4-(4-(BOC)-1-piperazinylcarbonyl)-phenylalanine, methyl ester (Isomer A).

Step G
N-(3-Phenylsulfonyl-nipecotyl)-(L)-4-(4-(BOC)-1-piperazinylcarbonyl)-phenylalanine (Isomer A).

N-(3-Phenylsulfonyl-nipecotyl)-(L)-4-(4-(BOC)-1-piperazinylcarbonyl)-phenylalanine, methyl ester (Isomer A) was saponified by the procedure described in Example 11, Step C to afford N-(3-phenylsulfonyl-nipecotyl)-(L)-4-(4-(BOC)-1-piperazinylcarbonyl)-phenylalanine (Isomer A) (24 mg).

Step H
N-(3-Phenylsulfonyl-nipecotyl)-(L)-4-(1-piperazinylcarbonyl)-phenylalanine (Isomer A).

N-(3-phenylsulfonyl-nipecotyl)-(L)-4-(4-(BOC)-1-piperazinyl-carbonyl)-phenylalanine (Isomer A) was treated with TFA by the procedure described in Example 1, Step C to provide N-(3-phenylsulfonyl-nipecotyl)-(L)-4-(1-piperazinylcarbonyl)-phenylalanine (Isomer A).

FABMS: 529 observed (M$^+$+1).

EXAMPLE 58

N-(3-Phenylsulfonyl-nipecotyl)-(L)-4-(1-piperazinylcarbonyl)-phenylalanine (Isomer B)

N-(3-Phenylthionipecotyl)-(L)-4-(4-(BOC)-1-piperazinylcarbonyl)-phenylalanine, methyl ester (Isomer B) from Example 57, Step E was reacted according to the procedures described in Example 57, Steps F–H in place of Isomer A to afford N-(3-phenylsulfonyl-nipecotyl)-(L)-4-(1-piperazinylcarbonyl)-phenylalanine (Isomer B).

FABMS: 529 observed (M$^+$+1).

EXAMPLES 59 AND 60

N-(3-Phenylsulfonyl)-nipecotyl)-(L)-4-(2-ethyl-4-thiazolyl)phenylalanine (Isomer A and Isomer B)

Step A
N-FMOC-(L)-(4-carboxyl)phenylalanine, methyl ester

N-FMOC-(L)-4-(tert-Butyloxycarbonyl)-phenylalanine, methyl ester (3.1 g, 6.18 mmol) was dissolved in 20 mL of CH$_2$Cl$_2$ and treated with 5.8 mL (11.6 mmol) of TFA. The reaction mixture was stirred overnight. The mixture was concentrated in vacuo to give a quantitative yield of N-FMOC-(L)-4-(carboxy)phenylalanine, methyl ester.

HPLC MS (ES): 446.3 (M+H)$^+$.

Step B
N-FMOC-(L)-4-(Chloromethyl carbonyl)-phenylalanine, methyl ester

A solution of N-FMOC-(L)-4-(carboxy)phenylalanine, methyl ester (500 mg, 1.12 mmol) in 7 mL of EtOAc was cooled to −20° C., then 190 μL of isobutyl chlorofomate and 173 μL of 4-methylmorpholine were added. This solution was stirred between −20° C. to −10° C. for one and a half hour. The mixed anhydride solution was filtered and the salt was washed with 5 mL of EtOAc. The filtrate was cooled in 0° C. bath and CH$_2$N$_2$ solution was added. The bath was removed and the solution was stirred overnight. The reaction mixture was concentrated in vacuo to 5 mL (without heat) and diluted with 5 mL of Et$_2$O. A solution of 1 N HCl in Et$_2$O (2.0 mL) was added slowly to the reaction. After ten minutes the reaction was quenched with saturated NaHCO$_3$, and extracted with Et$_2$O. The ether layer was washed with brine, dried over anhydrous MgSO$_4$, filtered and concentrated in vacuo. The residue was purified by flash column chromatography eluted with 10–30% EtOAc in hexanes to give N-FMOC-(L)-4-(chloromethyl carbonyl) phenylalanine, methyl ester (246 mg).

HPLC MS (ES): 478.1 (M+H)$^+$.

Step C
N-FMOC-(L)-4-(2-ethyl-4-thiazolyl)phenylalanine, methyl ester.

To a solution of N-FMOC-(L)-4-(chloromethyl carbonyl) phenylalanine, methyl ester (135 mg, 0.282 mmol) in 3 mL of acetone was added thiopropionamide (25 mg, 0.282 mmol). The mixture was stirred overnight and then was concentrated in vacuo to give N-FMOC-(L)-4-(2-ethyl-4-thiazolyl)-phenylalanine, methyl ester (143 mg).

HPLC MS (ES): 513.09 (M+H)$^+$.

Step D
N-(N-(BOC)-3-Phenylsulfonyl)-nipecotyl)-(L)-4-(2-ethyl-4-thiazolyl)-phenylalanine, methyl ester.

To a solution of N-FMOC-(L)-4-(2-ethyl-4-thiazolyl) phenylalanine, methyl ester (143 mg, 0.279 mmol) in 2.5 mL of DMF was added diethylamine (173 μL, 1.67 mmol). The reaction mixture was stirred for two hours then concentrated in vacuo to give an oily residue. This residue was coupled with N-(BOC)-3-phenylsulfonyl)-nipecotic acid according to the procedure described in Example 1, Step B to afford, after purification by preparative TLC on silica gel eluted with 50% EtOAc in hexane, N-(N-(BOC)-3-phenylsulfonyl)-nipecotyl)-(L)-4-(2-ethyl-4-thiazolyl)-phenylalanine, methyl ester (60 mg).

HPLC MS (ES): 642.26 (M+H)$^+$.

Step E
N-(N-(BOC)-3-Phenylsulfonyl)-nipecotyl)-(L)-4-(2-ethyl-4-thiazolyl)phenylalanine.

N-(N-(BOC)-3-Phenylsulfonyl)-nipecotyl)-(L)-4-(2-ethyl-4-thiazolyl)-phenylalanine, methyl ester (60 mg, 0.0925 mmol) was dissolved in 2.5 mL of MeOH and treated with 280 μL of 0.5 N NaOH. The reaction mixture was stirred overnight, acidified to pH=2–3 with 1.2 N HCl, and concentrated under vacuo to give a white solid. This solid was purified by preparative TLC on silica gel eluted with CH$_2$Cl$_2$:MeOH:AcOH (v/v/v 95:5:0.5) to afford N-(N-(BOC)-3-phenylsulfonyl)-nipecotyl)-(L)-4-(2-ethyl-4-thiazolyl)phenylalanine (34.9 mg).

HPLC MS (ES): 629.11 (M+H)$^+$.

Step F
N-(3-Phenylsulfonyl)-nipecotyl)-(L)-4-(2-ethyl-4-thiazolyl)-phenylalanine (Isomer A and Isomer B)

N-(N-(BOC)-3-Phenylsulfonyl)-nipecotyl)-(L)-4-(2-ethyl-4-thiazolyl)-phenylalanine (30 mg) was treated with a saturated solution of HCl(g) in EtOAc and was stirred overnight. The mixture was concentrated in vacuo to give a white solid. This solid was purified by preparative TLC on silica gel eluted with CH$_2$Cl$_2$:MeOH:NH$_4$OH (v/v/v 80:20:1). The plate was developed twice to give the two diastereomers of N-(3-phenylsulfonyl)-nipecotyl)-(L)-4-(2-ethyl-4-thiazolyl)phenylalanine: Isomer A (less polar, 12.3 mg) and Isomer B (more polar, 10.1 mg).

Isomer A: HPLC MS (ES): 528.06 (M+H)$^+$; 500 MHz $^1$H NMR (CD$_3$OD): 1.41 (t, 3H); 1.76 (d, 1H); 2.13 (m, 1H); 2.23 (m, 1H); 2.92 (m, 1H); 3.07 (m, 4H); 3.16 (d, 1H); 3.36 (m, 3H); 3.99 (d, 1H); 4.54 (d, 1H); 7.43 (m, 4H); 7.63 (m, 4H); 7.87 (d, 2H).

Isomer B: HPLC MS (ES): 528.08 (M+H)+; 500 MHz $^1$H NMR (CD$_3$OD): 1.39 (t, 3H); 2.04 (m, 3H); 2.31 (m, 1H); 2.95 (m, 2H); 3.06 (m, 3H); 3.19 (d, 2H); 3.41 (m, 3H); 4.48 (m, 1H); 7.04 (m, 2H); 7.28 (m, 2H); 7.56 (m, 3H); 7.62 (m, 1H); 7.96 (d, 2H).

EXAMPLE 61

Inhibition of VLA-4 Dependent Adhesion to BSA-CS-1 Conjugate

Step A.

Preparation of CS-1 Coated Plates.

Untreated 96 well polystyrene flat bottom plates were coated with bovine serum albumin (BSA; 20 mg/ml) for 2 hours at room temperature and washed twice with phosphate buffered saline (PBS). The albumin coating was next derivatized with 10 mg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 mg/ml and allowed to react for 2 hours at room temperature. The plates were washed twice with PBS and stored at 4° C.

Step B.

Preparation of Fluorescently Labeled Jurkat Cells.

Jurkat cells, clone E6-1, obtained from the American Type Culture Collection (Rockville, Md.; cat #ATCC TIB-152) were grown and maintained in RPMI-1640 culture medium containing 10% fetal calf serum (FCS), 50 units/ml penicillin, 50 mg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of 2×10$^6$ cells/ml in PBS containing a 1 mM concentration of a fluorogenic esterase substrate (2',7'-bis-(2-carboxyethyl)-5-(and -6)-carboxyfluorescein, acetoxymethyl ester; BCECF-AM; Molecular Probes Inc., Eugene, Oregon; catalog #B-1150) for 30–60 minutes at 37° C. in a 5% CO$_2$/air incubator. The fluorescently labeled Jurkat cells were washed two times in PBS and resuspended in RPMI containing 0.25% BSA at a final concentration of 2.0×10$^6$ cells/ml.

Step C.

Assay Procedure.

Compounds of this invention were prepared in DMSO at 100× the desired final assay concentration. Final concentrations were selected from a range between 0.001 nM–100 mM. Three mL of diluted compound, or vehicle alone, were premixed with 300 mL of cell suspension in 96-well polystyrene plates with round bottom wells. 100 mL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the IC$_{50}$ was determined from a ten point titration using a validated four parameter fit algorithm.

EXAMPLE 62

Antagonism of VLA-4 Dependent Binding to VCAM-Ig Fusion Protein

Step A.

Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences: 3'-PCR primer: 5'-AATTATAAMfTGATCAACTTAC CTGTCAATTCTTACAGCCTGCC-3'; 5'-PCR primer: 5'-ATAGGAATTCCAGCTGCCACCATGCCTGGGAAG-ATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:
MPGKMVVILGASNILWIMFAASQAFKI-ETTPESRYLAQIGDSVSLTCSTTGCES PFFSWRTQID-SPLNGKVTNEGTTSTLTMNPVSFGNEH-SYLCTATCESRKLEKGI QVEIYSFPKDPEIHLSGPLEAGK-PITVKCSVADVYPFDRLEIDLLKGDHLMKSQ EFLEDADRKSLETKSLEVTFT-PVIEDIGKVLVCRAKLHIDEMDSVPTVRQAVK EL.
The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRi and NotI and ligated to pCI-neo (Promega, Madison, Wis.) digested with EcoRi and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 mg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B.

Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat #NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C.

VCAM-Ig Binding Assay.

Compounds of this invention were prepared in DMSO at 100× the desired final assay concentration. Final concentrations were selected from a range between 0.001 nM–100 μM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat#MHVBN4550, Millipore Corp., Mass.) by making the following additions to duplicate wells: (i) 200 μL of binding buffer containing 1 mM $MnCl_2$; (ii) 20 μL of $^{125}$I-VCAM-Ig in binding buffer containing 1 mM $MnCl_2$ (final assay concentration ~100 pM); (iii) 2.5 μL of compound solution or DMSO; (iv) and 0.5×10⁶ cells in a volume of 30 mL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Contol wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 63

Antagonism of $\alpha_4\beta_7$ Dependent Binding to VCAM-Ig Fusion Protein

Step A.

$\alpha_4\beta_7$ Cell line.

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/100 μg streptomycin/2 mM L-glutamine at 37° C., 5 % carbon dioxide. The cells were pelleted at 1000 rpm for 5 minutes and then washed twice and resuspended in binding buffer (25 mM Hepes, 150 mM NaCl, 0.1% BSA, 3 mM KCl, 2 mM Glucose, pH 7.4).

Step B.

VCAM-Ig Binding Assay.

Compounds of this invention were prepared in DMSO at 100× the desired final assay concentration. Final concentrations were selected from a range between 0.001 nM–100 μM. Compounds were assayed in Millipore MHVB multiscreen plates (Cat# MHVBN4550) by making the following sequential additions to duplicate wells: (i) 100 ml/well of binding buffer containing 1.5 mM $MnCl_2$; (ii) 10 ml/well $^{125}$I-VCAM-Ig in binding buffer (final assay concentration <500 pM); (iii) 1.5 ml/well test compound or DMSO alone;

(iv) 38 ml/well RPMI-8866 cell suspension (1.25×10⁶ cells/well). The plates were incubated at room temperature for 45 minutes on a plate shaker at 200 rpm, filtered on a vacuum box, and washed on the same apparatus by the addition of 100 mL of binding buffer containing 1 mM $MnCl_2$. After insertion of the multiscreen plates into adapter plates (Packard, Meriden, Conn., cat# 6005178), 100 mL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{50}$ was determined from a ten point titration using a validated four parameter fit algorithm.

What is claimed is:

1. A compound of formula I:

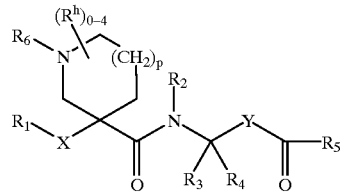

or a pharmaceutically acceptable salt thereof wherein:

X is
  1) —S—,
  2) —S(O)m—,

Y is
  1) a bond, or
  2) —C(R⁷)(R⁸)— m is an integer from 1 to 2;

n is an integer from 1 to 10;

p is a number chosen from 0, 1, 2, or 3;

R¹ is
  1) hydrogen, provided X is S,
  2) $C_{1-10}$alkyl,
  3) $C_{2-10}$alkenyl,
  4) $C_{2-10}$alkynyl,
  5) Cy, or
  9) —NR$^d$R$^e$,
    wherein alkyl, alkenyl and alkynyl are optionally substituted with one to four substituents selected from R$^a$, and Cy is optionally substituted with one to four substituents independently selected from R$^b$;

R² is
  1) hydrogen,
  2) $C_{1-10}$alkyl,
  3) $C_{2-10}$alkenyl, and
  4) $C_{2-10}$alkynyl,
    wherein alkyl, alkenyl and alkynyl are optionally substituted with one to four substituents independently selected from R$^a$;

R³ is
  1) $C_{1-10}$alkyl,
  2) Ar¹,
  3) Ar¹-$C_{1-10}$alkyl,
  4) Ar¹—Ar²,
  5) Ar¹—Ar²-$C_{1-10}$alkyl, wherein the alkyl group is optionally substituted with one to four substituents selected from $R^a$, and $Ar^1$ and $Ar^2$ are optionally substituted with one to four substituents independently selected from $R^b$, $R^4$ is
1) hydrogen,
2) $C_{1-10}$alkyl,
3) $C_{2-10}$alkenyl,
4) $C_{2-10}$alkynyl,
   wherein alkyl, alkenyl and alkynyl are optionally substituted with one to four substituents independently selected from $R^a$;

$R^5$ is
1) hydroxy,
2) $C_{1-10}$alkoxy,
3) $C_{2-10}$alkenyloxy,
4) $C_{2-10}$alkynyloxy,
5) Cy—O—,
6) Cy-$C_{1-10}$alkoxy,
7) amino,
8) $C_{1-10}$alkylamino,
9) di($C_{1-10}$alkyl)amino,
10) Cy-$C_{1-10}$alkylamino,
    wherein alkyl, alkenyl and alkynyl are optionally substituted with one to four substituents selected from $R^a$, and Cy is optionally substituted with one to four substituents independently selected from $R^b$;

$R^6$ is
1) hydrogen,
2) $C_{1-10}$alkyl,
3) $C_{2-10}$alkenyl,
4) $C_{2-10}$alkynyl,
5) Cy
6) —S(O)$_m$R$^d$,
7) —S(O)$_m$NR$^d$R$^e$,
8) —C(O)R$^d$,
9) —CO$_2$R$^d$,
10) —CO$_2$(CR$^f$R$^g$)$_n$CONR$^d$R$^e$, or
11) —C(O)NR$^d$R$^e$,
    wherein alkyl, alkenyl and alkynyl are optionally substituted with one to four substituents independently selected from $R^a$, and Cy is optionally substituted with one to four substituents independently selected from $R^b$; or $R^6$ and an Rh attached to the carbon atom adjacent to the ring nitrogen together complete a 4–8 membered ring optionally containing one other heteroatom chosen from nitrogen, oxygen and sulfur;

$R^7$ is
1) hydrogen,
2) $C_{1-10}$ alkyl,
3) $C_{2-10}$ alkenyl,
4) $C_{2-10}$ alkynyl,
5) $Ar^1$,
6) $Ar^1$-$C_{1-10}$alkyl,
7) —OR$^d$,
8) —O(CR$^f$R$^g$)$_n$NR$^d$R$^e$,
9) —OC(O)R$^d$,
10) —OC(O)NR$^d$R$^e$,
11) halogen,
12) —SR$^d$,
13) —S(O)$_m$R$^d$,
14) —S(O)$_2$OR$^d$,
15) —S(O)$_m$NR$^d$R$^e$,
16) —NO$_2$,
17) —NR$^d$R$^e$,
18) —NR$^d$C(O)R$^e$,
19) —NR$^d$S(O)$_m$R$^e$,
20) —NR$^d$C(O)OR$^e$, or
21) —NR$^d$C(O)NR$^d$R$^e$,
    wherein alkyl, alkenyl, alkynyl and $Ar^1$ are optionally substituted with one to four substituents selected from a group independently selected from $R^c$;

$R^8$ is
1) hydrogen,
2) $C_{1-10}$ alkyl,
3) $C_{2-10}$ alkenyl,
4) $C_{2-10}$ alkynyl,
5) Cy, or
6) $Ar^1$-$C_{1-10}$alkyl,
   wherein alkyl, alkenyl, alkynyl, Cy and $Ar^1$ are optionally substituted with one to four substituents selected from a group independently selected from $R^c$;

$R^a$ is
1) halogen,
2) —OR$^d$,
3) —OC(O)R$^d$,
4) —OC(O)NR$^d$R$^e$,
5) —O(CR$^f$R$^g$)$_n$NR$^d$R$^e$,
6) —SR$^d$,
7) —S(O)$_m$R$^d$,
8) —S(O)$_2$OR$^d$,
9) —S(O)$_m$NR$^d$R$^e$,
10) —NR$^d$R$^e$,
11) —NR$^d$C(O)R$^e$,
12) —NR$^d$C(O)OR$^e$,
13) —NR$^d$C(O)NR$^d$R$^e$,
14) —C(O)R$^d$,
15) —CO$_2$R$^d$,
16) —C(O)NR$^d$R$^e$,
17) —CO$_2$(CR$^f$R$^g$)$_n$CONR$^d$R$^e$,
18) —CN,
19) —CR$^d$(N—OR$^e$),
20) —NO$_2$,
21) CF$_3$,
22) —OCF$_3$, or
23) Cy optionally substituted with one to four substituents independently selected from $R^c$;

$R^b$ is
1) a group selected from $R^a$,
2) $C_{1-10}$ alkyl,
3) $C_{2-10}$ alkenyl,
4) $C_{2-10}$ alkynyl, or
8) $Ar^1$-$C_{1-10}$alkyl,
   wherein alkyl, alkenyl, alkynyl and $Ar^1$ are optionally substituted with one to four substituents selected from a group independently selected from $R^c$;

$R^c$ is
1) halogen,
2) amino,
3) $C_{1-4}$alkylamino,
4) di($C_{1-4}$alkyl)amino,
5) carboxy,
6) cyano,
7) $C_{1-4}$alkyl,
8) aryl$C_{1-4}$alkyl,
9) $Ar^1$,
10) hydroxy,
11) $C_{1-4}$alkoxy, 12) aryloxy, or
13) $CF_3$;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atoms to which they are attached form a heterocyclic ring of 4 to 7 members containing 0–2 additional heteroatoms independently selected from oxygen, sulfur and nitrogen;

$R^f$ and $R^g$ are independently selected from hydrogen, $C_{1-10}$alkyl, Cy and Cy-$C_{1-10}$alkyl; or $R^f$ and $R^g$ together with the carbon to which they are attached form a ring of 4 to 7 members containing 0–2 heteroatoms independently selected from oxygen, sulfur and nitrogen;

$R^h$ is
1) a group selected from $R^a$,
2) $C_{1-10}$ alkyl,
3) $C_{2-10}$ alkenyl,
4) $C_{2-10}$ alkynyl,
5) Cy,
6) oxo,
   wherein alkyl alkenyl, alkynyl, and Cy are optionally substituted with one to four substituents selected from a group independently selected from $R^c$; or two $R^h$ groups attached to adjacent ring atoms together complete 4–8 membered aromatic or non-aromatic ring containing 0–2 heteroatom selected from oxygen, sulfur and nitrogen; or two $R^h$ groups attached to the same ring atom together complete a 4–8 membered ring containing 0–2 heteroatom selected from oxygen, sulfur and nitrogen; with the proviso that when $R^h$ is chosen from
1) —$OR^d$,
2) —$OC(O)R^d$,
3) —$OC(O)NR^dR^e$,
4) —$O(CR^fR^g)_nNR^dR^e$,
5) —$SR^d$,
6) —$S(O)_mR^d$,
7) —$S(O)_2OR^d$,
8) —$S(O)_mNR^dR^e$,
9) —$NR^dR^e$,
10) —$NR^dC(O)R^e$,
11) —$NR^dC(O)OR^e$,
12) —$NR^dC(O)NR^dR^e$, or
13) —$NO_2$,
14) halogen,
15) —CN, and
16) —$CR^d(N$—$OR^e)$,
it is not attached to an atom adjacent to the ring nitrogen;

Cy is cycloalkyl, heterocyclyl, aryl or heteroaryl;

$Ar^1$ and $Ar^2$ are independently selected from aryl and heteroaryl.

2. A compound of claim 1 wherein X is S or $SO_2$.

3. A compound of claim 1 wherein Y is a bond.

4. A compound of claim 1 wherein $R^1$ is $C_{1-10}$ alkyl optionally substituted with one to four substituents selected from $R^a$, or Cy optionally substituted with one to four substituents selected from $R^b$.

5. A compound of claim 1 whrein $R^1$ is $C_{1-5}$alkyl optionally substituted with a group selected from $NR^dR^e$, $NO_2$, phenyl, hydroxy and 1-imidazolyl.

6. A compound of claim 1 wherein $R^1$ is aryl or heteroaryl each optionally substituted with one to two substituents selected from $R^b$.

7. A compound of claim 1 wherein $R^1$ is phenyl optionally substituted with one or two substituents selected from halogen and $NR^dR^e$.

8. A compound of claim 1 wherein $R^2$ and $R^4$ are each hydrogen, $R^5$ is OH, and $R^3$ is $Ar^1$-$C_{1-3}$alkyl or $Ar^1$-$Ar^2$-$C_{1-3}$alkyl wherein $Ar^1$ and $Ar^2$ are each optionally substituted with one to four groups independently selected from $R^b$.

9. A compound of claim 8 wherein $R^3$ is optionally substituted benzyl or optionally substituted $Ar^2$-benzyl, where $Ar^2$ is optionally substituted phenyl, or optionally substituted 5- or 6-membered heteroaryl.

10. A compound of claim 8 wherein $R^3$ is benzyl, benzyl substituted with a group selected from hydroxy, $C_{1-5}$alkoxy, $NHC(O)R^e$, $OC(O)NR^dR^e$, and $C(O)NR^dR^e$, or 4-($Ar^2$)-benzyl wherein $Ar^2$ is phenyl substituted with one to two groups selected from $C_{1-5}$alkyl, hydroxy, $C_{1-5}$alkoxy and $NR^dR^e$, or $Ar^2$ is 2-ethyl-4-thiazolyl.

11. A compound of claim 1 having the formula Ia:

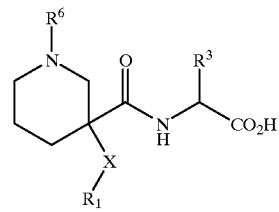

Ia wherein

X is
1) S or
2) $SO_2$;

$R^1$ is
1) $C_{11-5}$alkyl optionally substituted with one to two substituents selected from $R^a$;
2) aryl or heteroaryl each optionally substituted with one to two substituents selected from $R^b$;

$R^3$ is 1) $Ar^1$-$C_{1-3}$alkyl, or
2) $Ar^1$-$Ar^2$-$C_{1-3}$alkyl;

$R^6$ is
1) hydrogen or
2) $C_{1-5}$alkyl;

$R^a$, $R^b$, $Ar^1$ and $Ar^2$ are as defined in claim 1.

12. A compound of claim 11 wherein $R^1$ is $C_{1-15}$alkyl optionally substituted with a group selected from $NR^dR^e$, $NO_2$, phenyl, hydroxy and 1-imidazolyl.

13. A compound of claim 11 wherein $R^1$ is phenyl optionally substituted with one or two substituents selected from halogen and $NR^dR^e$.

14. A compound of claim 11 wherein $R^3$ is benzyl, benzyl substituted with a group selected from hydroxy, $C_{1-5}$alkoxy, $NHC(O)R^e$, $OC(O)NR^dR^e$, and $C(O)NR^dR^e$, or 4-($Ar^2$)-benzyl wherein $Ar^2$ is phenyl substituted with one to two groups selected from $C_{1-5}$alkyl, hydroxy, $C_{1-5}$alkoxy and $NR^dR^e$, or $Ar^2$ is 2-ethyl-4-thiazolyl.

15. A compound of claim 1 having the formula Ib:

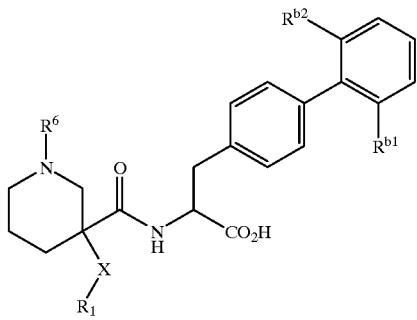

wherein
X is
  1) S or
  2) $SO_2$;
$R^1$ is
  1) $C_{1-5}$alkyl optionally substituted with a group selected from $NR^dR^e$, $NO_2$, phenyl, hydroxy and 1-imidazolyl;
  2) phenyl optionally substituted with one or two substituents selected from halogen and $NR^dR^e$;
$R^6$ is
  1) hydrogen or
  2) $C_{1-5}$alkyl;
$R^{b1}$ and $R^{b2}$ are independently selected from
  1) hydrogen,
  2) $C_{1-5}$alkyl,
  3) hydroxy,
  4) $C_{1-5}$alkoxy and
  5) $NR^dR^e$;
$R^d$ and $R^e$ are as defined in claim 1.

16. A compound of claim 1 having formula Ic:

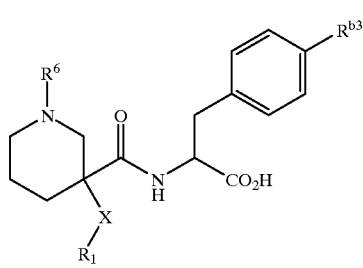

wherein
X is
  1) S or
  2) $SO_2$;
$R^1$ is
  1) $C_{1-5}$alkyl optionally substituted with a group selected from $NR^dR^e$, $NO_2$, phenyl, hydroxy and 1-imidazolyl;
  2) phenyl optionally substituted with one or two substituents selected from halogen and $NR^dR^e$;
$R^6$ is
  1) hydrogen or
  2) $C_{1-5}$alkyl;

$R^{b3}$ is
  1) hydrogen,
  2) hydroxy,
  3) $C_{1-5}$alkoxy,
  4) $NHC(O)R^e$,
  5) $OC(O)NR^dR^e$, or
  6) $C(O)NR^dR^e$,
$R^d$ and $R^e$ are as defined above for formula I.

17. A compound of claim 1 selected from the group consisting of:

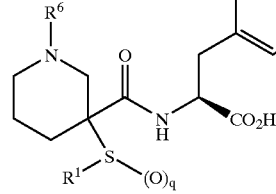

| q | $R^1$ | $R^6$ | $R^{b1}/R^{b2}$ |
|---|-------|-------|-----------------|
| 0 | Ph | H | H/$OCH_3$ |
| 0 | Ph | H | $OCH_3$/$OCH_3$ |
| 2 | Ph | H | H/$OCH_3$ |
| 2 | Ph | $CH_3$ | H/$OCH_3$ |
| 2 | Ph | H | $OCH_3$/$OCH_3$ |
| 2 | 4-Br-Ph | H | $OCH_3$/$OCH_3$ |
| 2 | 3-Br-Ph | H | $OCH_3$/$OCH_3$ |
| 2 | 2-Br-Ph | H | $OCH_3$/$OCH_3$ |
| 2 | 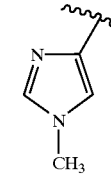 | H | $OCH_3$/$OCH_3$ |
| 2 | 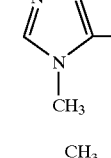 | H | $OCH_3$/$OCH_3$ |
| 2 | $CH_3$ | H | $OCH_3$/$OCH_3$ |
| 2 | 4-(PhCH$_2$NH)Ph | H | $OCH_3$/$OCH_3$ |
| 2 | 3-(PhCH$_2$NH)Ph | H | $OCH_3$/$OCH_3$ |
| 2 | 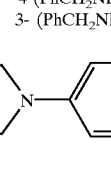 | H | $OCH_3$/$OCH_3$ |
| 2 | 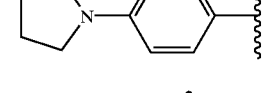 | H | $OCH_3$/$OCH_3$ |
| 2 | 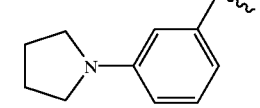 | H | $OCH_3$/$OCH_3$ |

-continued

| 2 | 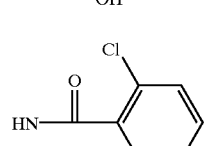 | H | OCH$_3$/OCH$_3$ |
| --- | --- | --- | --- |
| 2 | (CH$_3$)$_2$N(CH$_2$)$_3$NH(CH$_2$)$_2$ | H | OCH$_3$/OCH$_3$ |
| 2 | NO$_2$(CH$_2$)$_3$ | H | OCH$_3$/OCH$_3$ |
| 2 | 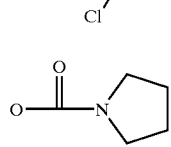 | H | OCH$_3$/OCH$_3$ |
| 2 | HOCH$_2$CH$_2$ | H | OCH$_3$/OCH$_3$ |
| 2 | Ph | H | H/CN |
| 2 | Ph | H | OCH$_3$/CN |
| 1 | Ph | H | OCH$_3$/OCH$_3$ |
| 2 | Ph | H | OCH$_3$/N(CH$_3$)$_2$ |
| 2 | Ph | H | OCH$_3$/OH |
| 2 | Ph | H | OCH$_3$/CH$_2$CH$_3$ |
| 2 | PhCH$_2$ | H | OCH$_3$/OCH$_3$ |

R = OH or NO$_2$

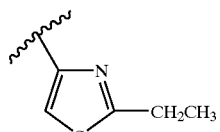

| q | R$^1$ | R$^6$ | R$^{b3}$ |
| --- | --- | --- | --- |
| 0 | Ph | H | H |
| 0 | Ph | H | OH |
| 2 | Ph | H | OH |
| 2 | Ph | H | 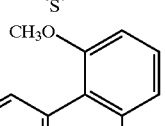 |
| 2 | Ph | H | 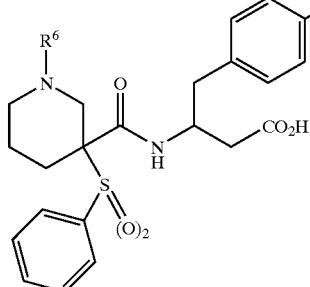 |

-continued

| 2 | Ph | H | (piperazine-formyl structure) |
| --- | --- | --- | --- |
| 2 | Ph | H | (thiazole-ethyl structure) |

(large structure with R$^6$, biphenyl dimethoxy, piperidine, sulfone)

R$^6$ = t-BOC or H

18. A method for inhibiting cell adhesion in a mammal which comprises administering to said mammal an effective amount of a compound of claim 1.

19. A method for the treatment of diseases, disorders, conditions or symptoms mediated by cell adhesion in a mammal which comprises administering to said mammal an effective amount of a compound of claim 1.

20. A method for the treatment of asthma in a mammal which comprises administering to said mammal a therapeutically effective amount of a compound of claim 1.

21. A method for the treatment of allergic rhinitis in a mammal which comprises administering to said mammal a therapeutically effective amount of a compound of claim 1.

22. A method for the treatment of multiple sclerosis in a mammal which comprises administering to said mammal a therapeutically effective amount of a compound of claim 1.

23. A method for the treatment of atherosclerosis in a mammal which comprises administering to said mammal a therapeutically effective amount of a compound of claim 1.

24. A method for the treatment of inflammation in a mammal which comprises administering to said mammal an effective amount of a compound of claim 1.

25. A method for the treatment of inflammatory bowel disease in a mammal which comprises administering to said mammal a therapeutically effective amount of a compound of claim 1.

26. A pharmaceutical composition which comprises a compound of claim 1 and a pharmaceutically acceptable carrier thereof.

* * * * *